US012575945B2

(12) United States Patent
Greenhalgh et al.

(10) Patent No.: US 12,575,945 B2
(45) Date of Patent: Mar. 17, 2026

(54) METHODS, SYSTEMS, AND APPARATUSES FOR SPINAL FUSION

(71) Applicant: SurGenTec, LLC, Boca Raton, FL (US)

(72) Inventors: Travis Greenhalgh, Boca Raton, FL (US); Andrew Shoup, Boca Raton, FL (US); Bryan Hellriegel, Boynton Beach, FL (US)

(73) Assignee: SurGenTec, LLC, Boca Raton, FL (US)

( * ) Notice: Subject to any disclaimer, the term of this patent is extended or adjusted under 35 U.S.C. 154(b) by 808 days.

(21) Appl. No.: 17/882,337

(22) Filed: Aug. 5, 2022

(65) Prior Publication Data

US 2023/0039837 A1    Feb. 9, 2023

Related U.S. Application Data

(60) Provisional application No. 63/229,956, filed on Aug. 5, 2021.

(51) Int. Cl.
*A61F 2/46*          (2006.01)
(52) U.S. Cl.
CPC ..... *A61F 2/4611* (2013.01); *A61F 2002/4629* (2013.01); *A61F 2002/4677* (2013.01); *A61F 2002/4687* (2013.01)
(58) Field of Classification Search
CPC .................. A61F 2/4405; A61F 2/4611; A61F 2002/4629; A61F 2002/4677; A61F 2002/4687; A61B 17/7064
See application file for complete search history.

(56) References Cited

U.S. PATENT DOCUMENTS

| | | | |
|---|---|---|---|
| 4,877,020 | A | 10/1989 | Vich |
| 6,517,542 | B1 | 2/2003 | Papay |
| 6,770,074 | B2 | 8/2004 | Michelson |
| 7,648,509 | B2 | 1/2010 | Stark |
| 7,837,713 | B2 | 11/2010 | Petersen |
| D629,905 | S | 12/2010 | Horton et al. |
| 7,938,832 | B2 | 5/2011 | Culbert et al. |
| 8,043,334 | B2 | 10/2011 | Fisher et al. |
| 8,062,270 | B2 | 11/2011 | Sweeney |
| 8,267,966 | B2 | 9/2012 | McCormack et al. |
| 8,361,152 | B2 | 1/2013 | McCormack et al. |
| 8,425,558 | B2 | 4/2013 | McCormack et al. |
| 8,512,347 | B2 | 8/2013 | McCormack et al. |
| 8,623,054 | B2 | 1/2014 | McCormack et al. |
| 8,696,708 | B2 | 4/2014 | Lechmann et al. |

(Continued)

FOREIGN PATENT DOCUMENTS

| | | | |
|---|---|---|---|
| WO | WO-0062684 A1 * | 10/2000 | ............ A61F 2/4611 |
| WO | WO 04/043278 | 5/2004 | |

*Primary Examiner* — Nicholas J Plionis
(74) *Attorney, Agent, or Firm* — Knobbe Martens Olson & Bear, LLP

(57) ABSTRACT

A method for implanting an intrafacet implant includes making an incision, advancing an instrument assembly through the incision and to a facet joint. The instrument assembly includes a guide having a lumen extending therethrough. The method includes anchoring the guide at the facet joint, advancing an intrafacet implant to the facet joint through the guide using an inserter, and countersinking the intrafacet implant within the facet joint using the inserter.

20 Claims, 46 Drawing Sheets

400a

(56) References Cited

U.S. PATENT DOCUMENTS

| | | | |
|---|---|---|---|
| 8,753,347 B2 | 6/2014 | McCormack et al. | |
| 8,753,377 B2 | 6/2014 | McCormack et al. | |
| 8,821,506 B2 | 9/2014 | Mitchell | |
| 8,828,062 B2 | 9/2014 | McCormack et al. | |
| 8,834,472 B2 | 9/2014 | McCormack et al. | |
| 8,870,836 B2 | 10/2014 | Sweeney | |
| 9,011,492 B2 | 4/2015 | McCormack et al. | |
| 9,119,678 B2 | 9/2015 | Duggal et al. | |
| 9,333,086 B2 | 5/2016 | McCormack et al. | |
| 9,381,049 B2 | 7/2016 | McCormack et al. | |
| 9,492,284 B2 | 11/2016 | Ginn et al. | |
| 9,603,644 B2 | 3/2017 | Sweeney | |
| 9,615,856 B2 | 4/2017 | Arnett et al. | |
| 9,622,791 B2 | 4/2017 | McCormack et al. | |
| 9,622,874 B2 | 4/2017 | McCormack et al. | |
| 9,629,665 B2 | 4/2017 | McCormack et al. | |
| 9,668,781 B2 | 6/2017 | Stark | |
| 9,943,342 B2 | 4/2018 | Tanaka et al. | |
| 10,039,649 B2 | 8/2018 | McCormack et al. | |
| 10,149,673 B2 | 12/2018 | McCormack et al. | |
| 10,172,721 B2 | 1/2019 | McCormack et al. | |
| 10,226,285 B2 | 3/2019 | McCormack et al. | |
| 10,238,501 B2 | 3/2019 | McCormack et al. | |
| 10,456,175 B2 | 10/2019 | McCormack et al. | |
| 10,568,666 B2 | 2/2020 | McCormack et al. | |
| 10,588,672 B2 | 3/2020 | McCormack et al. | |
| 10,596,003 B2 | 3/2020 | Donner et al. | |
| 10,646,236 B2 | 5/2020 | Donner et al. | |
| 10,653,458 B2 | 5/2020 | Tanaka et al. | |
| 10,653,535 B2 | 5/2020 | McCormack et al. | |
| 10,682,243 B2 | 6/2020 | Phan et al. | |
| 10,687,877 B2 | 6/2020 | Lavigne et al. | |
| 10,856,922 B2 | 12/2020 | Loke | |
| 10,874,447 B2 | 12/2020 | Tanaka et al. | |
| 11,045,231 B2 | 6/2021 | Stark | |
| 11,058,553 B2 | 7/2021 | McCormack et al. | |
| 11,065,039 B2 | 7/2021 | McCormack et al. | |
| 11,141,144 B2 | 10/2021 | McCormack et al. | |
| 11,147,675 B2 | 10/2021 | Ginn et al. | |
| 11,224,521 B2 | 1/2022 | McCormack et al. | |
| 11,272,964 B2 | 3/2022 | McCormack et al. | |
| 11,344,339 B2 | 5/2022 | McCormack et al. | |
| 11,571,245 B2 | 2/2023 | Stuart | |
| 11,648,128 B2 | 5/2023 | Tanaka et al. | |
| 11,813,172 B2 | 11/2023 | Tanaka et al. | |
| 11,890,038 B2 | 2/2024 | McCormack et al. | |
| 11,951,010 B2 | 4/2024 | Greenhalgh | |
| 12,004,781 B2 | 6/2024 | McCormack et al. | |
| 12,186,195 B2 | 1/2025 | Greenhalgh | |
| 2001/0031968 A1* | 10/2001 | Dorchak | A61F 2/4455 |
| | | | 606/90 |
| 2002/0055783 A1 | 5/2002 | Tallarida et al. | |
| 2002/0072805 A1* | 6/2002 | Sullivan | A61F 2/40 |
| | | | 623/23.42 |
| 2003/0018391 A1 | 1/2003 | Evans | |
| 2004/0225292 A1 | 11/2004 | Sasso | |
| 2006/0036323 A1 | 2/2006 | Carl et al. | |
| 2008/0234758 A1* | 9/2008 | Fisher | A61B 17/7064 |
| | | | 606/301 |
| 2008/0255622 A1 | 10/2008 | Mickiewicz et al. | |
| 2009/0076551 A1 | 3/2009 | Petersen | |
| 2009/0131986 A1 | 5/2009 | Lee et al. | |
| 2009/0138053 A1* | 5/2009 | Assell | A61F 2/4611 |
| | | | 606/301 |
| 2009/0192551 A1 | 7/2009 | Cianfrani | |
| 2009/0275993 A1 | 11/2009 | Phan et al. | |
| 2010/0030135 A1 | 2/2010 | Mitchell | |
| 2011/0313462 A1 | 12/2011 | Alleyne | |
| 2012/0116454 A1* | 5/2012 | Edidin | A61B 17/1757 |
| | | | 606/279 |
| 2013/0013070 A1 | 1/2013 | McCormack et al. | |
| 2013/0144353 A1 | 6/2013 | Arnett | |
| 2014/0046381 A1 | 2/2014 | Asfora | |
| 2016/0100870 A1 | 4/2016 | Lavigne et al. | |
| 2016/0310188 A1 | 10/2016 | Marino | |
| 2016/0361096 A1 | 12/2016 | van der Pol | |
| 2017/0224393 A1 | 8/2017 | Lavigne et al. | |
| 2018/0280067 A1* | 10/2018 | Bjork | A61B 17/888 |
| 2018/0325570 A1 | 11/2018 | Kuntz | |
| 2019/0083271 A1 | 3/2019 | Donner et al. | |
| 2020/0121373 A1 | 4/2020 | Biedermann | |
| 2020/0268518 A1 | 8/2020 | Suh et al. | |
| 2023/0038914 A1 | 2/2023 | Muller | |
| 2023/0173146 A1 | 6/2023 | Brubaker et al. | |
| 2023/0181322 A1 | 6/2023 | Greenhalgh | |

* cited by examiner

100

134

116

122

104

110

138

108

106

102

112

120

136

124

114

108

120

120

136

100

100

108

108

310

300

400a

108

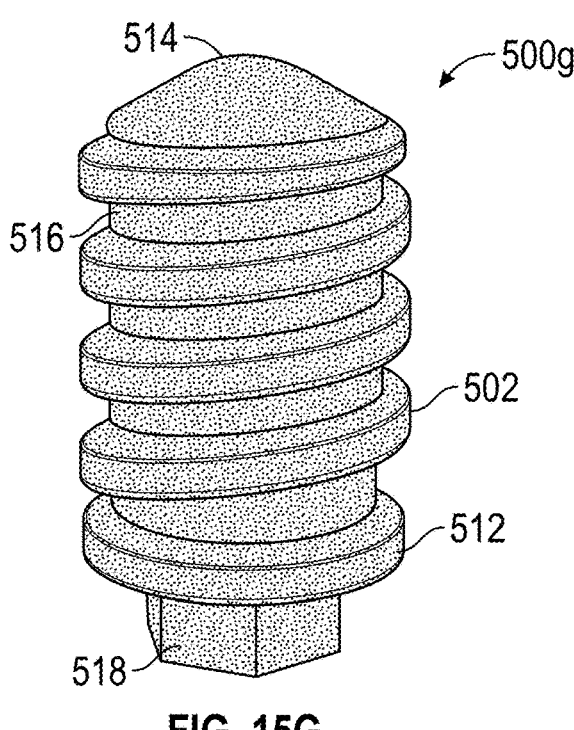
FIG. 15G
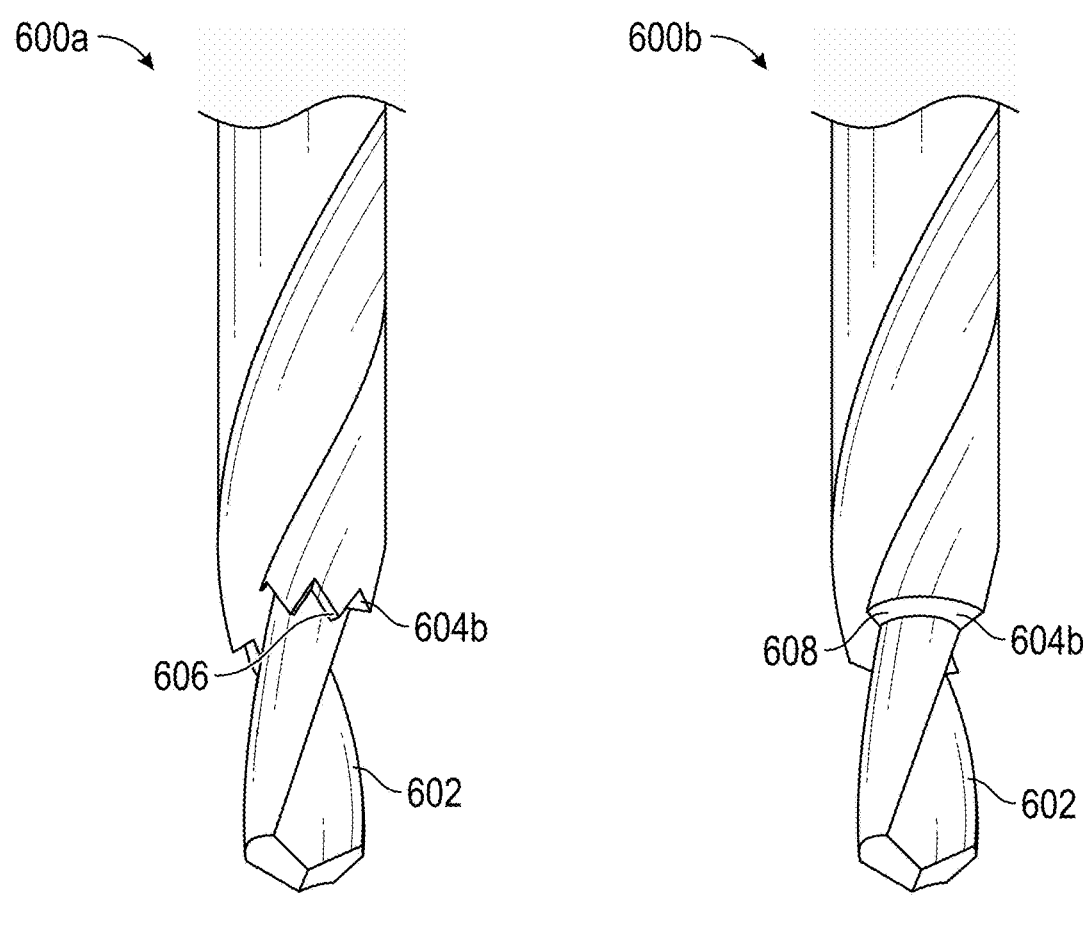
FIG. 16A                        FIG. 16B

700b 708
714
704
710a
706
716a
716b

700b 708
714
704
706
705
716a
716b

1000

1050

METHODS, SYSTEMS, AND APPARATUSES FOR SPINAL FUSION

CROSS-REFERENCE TO RELATED APPLICATIONS

The present application claims priority benefit of U.S. Provisional Application Ser. No. 63/229,956, entitled "METHODS, SYSTEMS, AND APPARATUSES FOR SPINAL FUSION," filed Aug. 5, 2021, the entire contents of which are incorporated by reference herein in their entirety and for all purposes.

BACKGROUND

Field

The present application relates to orthopedic surgery in general, and more particularly, to methods, systems, and apparatuses for spinal fusion.

Description of the Related Art

In a bone grafting procedure, a surgeon places bone or a bone substitute into an area in a patient's body to provide a type of scaffold for bone growth and repair. Bone grafts can be used to help treat various orthopedic problems, for example, to fuse a joint or repair a fracture. Bone graft material can be, for example, autogenous (harvested from the patient's own body), allogeneic (harvested from another person, usually a cadaver), or synthetic. Many bone grafting procedures are performed via open surgery implantation. However, these procedures can also be performed minimally invasively, for example, by using a needle to inject the bone graft material into the target location without requiring a surgical incision.

In some cases decortication of the bony area receiving the graft is performed prior to delivery of the bone graft material. Decortication removes superficial cortical bone and exposes the underlying cancellous bone, which can help accelerate the integration of the bone graft with the native bone.

BRIEF DESCRIPTION OF THE DRAWINGS

FIG. 15G illustrates a perspective view of an embodiment of an implant.

FIG. 16A illustrates a perspective view of a distal end of an embodiment of a drill bit.

FIG. 16B illustrates a perspective view of a distal end of an embodiment of a drill bit.

FIG. 26B illustrates an enlarged side view of a distal end of the removal system of FIG. 26A and an implant.

SUMMARY

Figure 1A:
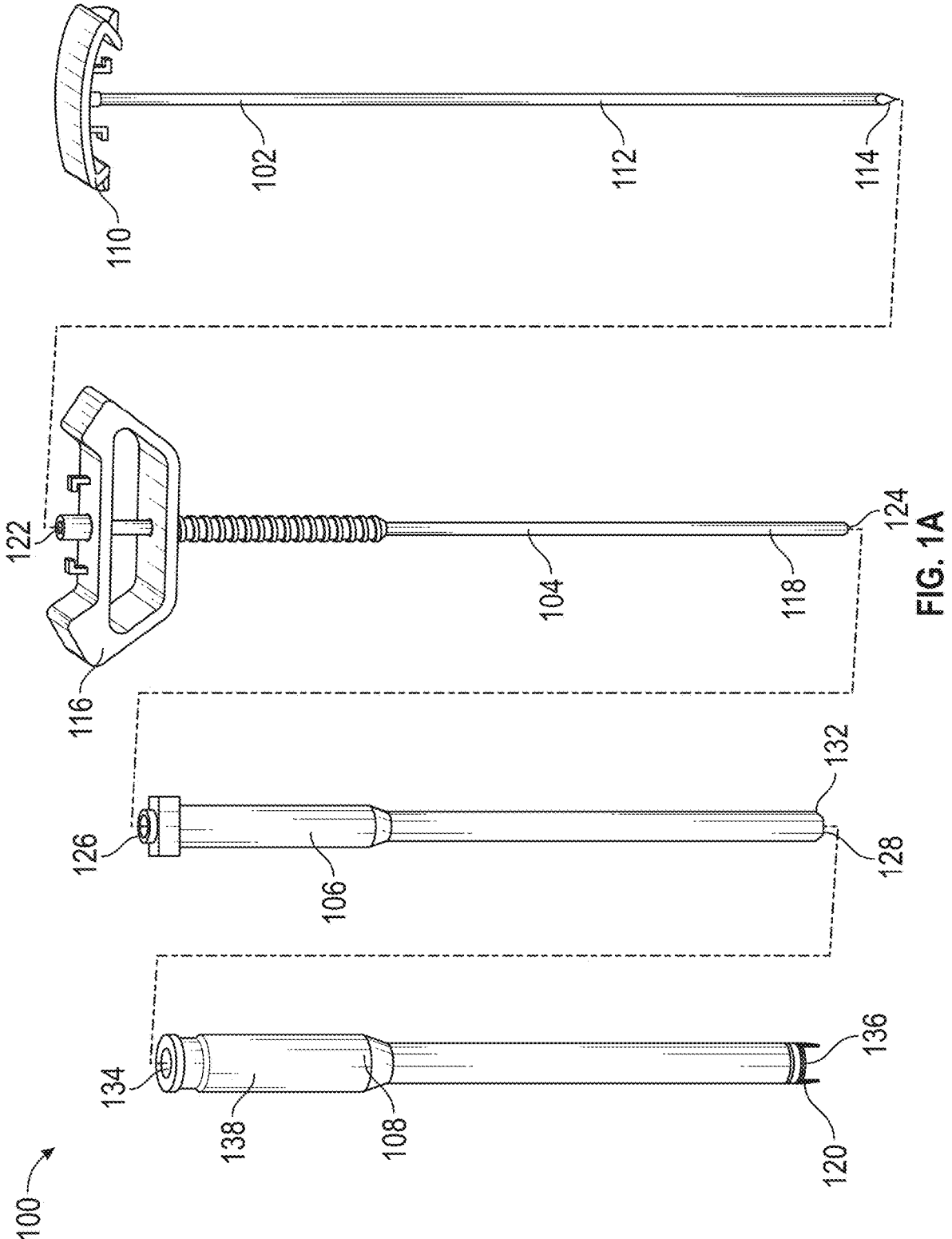
FIG. 1A illustrates a perspective view of an embodiment of a needle assembly.

Embodiments of the present application are directed to needle assemblies, intrafacet implants, implant inserters, rasps, drill bits, navigation systems and related systems, devices, and methods.

In some embodiments, a method for implanting an intrafacet implant is provided. The method includes making an incision, advancing an instrument assembly through the incision and to a facet joint, the instrument assembly including a guide having a lumen extending therethrough, anchoring the guide at the facet joint, advancing an intrafacet implant to the facet joint through the guide using an inserter, and countersinking the intrafacet implant within the facet joint using the inserter.

The method can further include advancing a drill bit through the guide to the facet joint and forming a pilot hole for the intrafacet implant using the drill bit. The drill bit can include a distal section of the drill bit configured to form a distal section of the pilot hole and a proximal section of the drill bit configured to form a proximal section of the pilot hole such that a cross-sectional area of the proximal section of the pilot hole is larger than a cross-sectional area of the distal section of the pilot hole. The proximal section of the drill bit can include a plurality of saw teeth, and the distal section of the drill bit can include a flute drill bit section or twist drill bit section. The proximal section of the drill bit can include a tapered blade, and the distal section of the drill bit can include a flute drill bit section or twist drill bit section. The inserter comprises a distal tip configured to couple with the intrafacet implant and a split extending proximally through the distal tip from a distal end of the inserter to a relief. The instrument assembly can include a stylet including a distal tip, wherein the stylet is positioned within the guide of the instrument assembly while advancing the instrument assembly through the incision and to the facet joint. The method can further include penetrating tissue with the distal tip of the stylet. The method can include removing the stylet prior to advancing the intrafacet implant to the facet joint. Anchoring the guide at the facet joint can include anchoring a plurality of prongs of the guide at the facet joint. The method can include rasping the facet joint using a rasp after countersinking the intrafacet implant within the facet joint. The intrafacet implant can include a body extending from a proximal end to a distal end of the intrafacet implant and a plurality of threads extending form the body from the proximal end to the distal end. The body of the intrafacet implant can have a uniform cross-sectional area. The method can include advancing a rasp into the facet joint and decorticating bone of the facet joint with the rasp and advancing a drill bit to the facet joint and forming a pilot hole for the intrafacet implant after decorticating bone of the facet joint with the rasp. The rasping surface of the rasp can be wider than a width of the drill bit. The rasping surface of the rasp can be a first rasping surface, and the rasp can include a second rasping surface positioned on an opposite side of the first rasping surface.

In some embodiments, a method of removing an intra-facet implant from a facet joint is provided. The method includes advancing a removal system to the intrafacet implant. The removal system includes an inserter including an engagement tip configured to engage an engagement recess of the intrafacet implant, and a removal sleeve positioned over at least a portion of the inserter, the removal sleeve including a tip configured to fit over and capture the intrafacet implant. The method includes engaging the engagement tip of the inserter with the engagement recess of the intrafacet implant. The method includes driving the inserter to draw the intrafacet implant out of the facet joint and into the tip of the removal sleeve, and removing the removal system and the intrafacet implant from a body of a patient while the intrafacet implant is secured within the removal sleeve.

The inserter can include a guide tip extending distally beyond the engagement tip, the guide tip having a smaller cross-sectional area than the engagement tip. The method can include advancing the guide tip into an interior of the intrafacet implant to align the engagement tip with the engagement recess. The method can include advancing a guidewire into an interior of the intrafacet implant, and advancing the inserter over the guidewire into alignment with the engagement recess of the intrafacet implant. The intrafacet implant can include a plurality of threads, and the tip of the removal sleeve can include a complementary plurality of threads. Driving the inserter to draw the intra-facet implant out of the facet joint and into the tip of the removal sleeve can include rotating the inserter to thread the plurality of threads of the intrafacet implant with the plu-rality of threads of the removal sleeve. The intrafacet implant can be countersunk within the facet joint prior to engaging the engagement tip of the inserter with the engage-ment recess of the intrafacet implant.

DETAILED DESCRIPTION

In certain embodiments, an instrument assembly can include one or more instruments for preparing a surgical location (such as a facet joint) for implantation and/or for delivering an implant to the surgical location. For example, an instrument assembly may include a guide that can be positioned (e.g., anchored) at a surgical location and used to guide other instruments to the surgical location. In certain embodiments, an instrument assembly may also include one or more dilators that can be positioned within an inner lumen of the guide and advanced with the guide to the surgical location. Such dilators may prevent tissue from entering and/or obstructing the guide while the guide is advanced to the surgical location. In some embodiments, the instrument assembly can include a needle instrument (e.g., a stylet having a sharp tip) that can be used to penetrate tissue and/or bone. For example, the needle instrument may be positioned within a guide and/or dilator such that a sharp tip extends distally beyond the other instruments of the instrument assembly. The instrument assembly can then be advanced to a surgical location, and the sharp tip can penetrate tissue to form a path for the instrument assembly to the surgical location. The sharp tip may also be used to form a pilot hole in bone at the surgical location.

FIG. 1A illustrates an exploded view of an embodiment of an instrument assembly or needle assembly 100. The needle assembly 100, can be used for a variety of procedures, for example, for bone marrow biopsies, delivering bone graft and/or other materials to a target location, or to access a target location and form a pilot hole, for example to access a pedicle or facet joint for delivery of an implant, such as an intrafacet implant, facet screw, facet dowel, pedicle screw, or any other suitable implant.

As shown in FIG. 1A, the needle assembly 100 can include a stylet 102 and a cannula 104. As shown in FIG. 1A, the stylet 102 can include a stylet handle 110 and a stylet shaft 112 having a sharp distal tip 114. The tip 114 can be configured to penetrate tissue and/or bone.

The cannula 104 can include a cannula handle 116 and a cannula shaft 118. The stylet shaft 112 can be received within a lumen of the cannula shaft 118. The lumen of the cannula shaft 118 can extend between an opening 122 at a proximal end of the cannula shaft 118 and an opening 124 at a distal end of the cannula shaft 118. The stylet shaft 112 can be received through an opening 122. The tip 114 can be configured to extend beyond a distal end of the cannula shaft 118 through the opening 124 when the stylet 102 is inserted into the cannula 104.

In some embodiments, the cannula handle 116 and stylet handle 110 can be configured to couple to one another to secure the stylet 102 within the cannula 104.

In some embodiments, the needle assembly 100 can include a dilator 106. In some embodiments, the dilator 106 can be used dilate muscle and/or tissue to create a channel within the body for access to a surgical location. For example, the dilator 106 can be configured to dilate tissue to the facet joint. For example, the dilator 106 can include a tip 132 shaped, dimensioned, or otherwise configured to dilate muscle and/or tissue to create a channel within the body for access to a surgical location. In some embodiments, the tip 132 can have a tapered shape.

In some embodiments, the dilator 106 can include a lumen configured to receive the cannula shaft 118. The lumen of the dilator 106 can extend between an opening 126 at a proximal end of the dilator 106 and an opening 128 at a distal end of the dilator 106. The cannula shaft 118 can be received through the opening 126. In some embodiments, the dilator 106 can be secured to the cannula 104, for example, via a threaded connection. The dilator 106 can include internal threads configured to couple with external threads of the cannula 104. In alternative embodiments, as shown for example in FIG. 1B, the dilator 106 can be integrally formed with the cannula 104 as a single piece, for example, via injection molding. In certain embodiments, at least the tip 114 of the stylet shaft 112 can be configured to extend beyond the distal end of the dilator 106 through the opening 128.

Figures 1B, 1C:
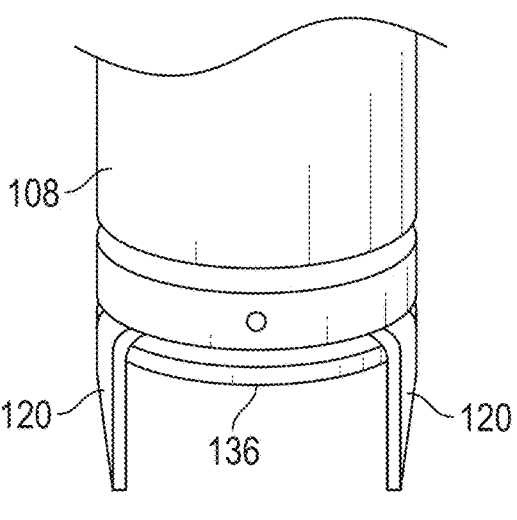
FIG. 1B illustrates a perspective view of an alternative embodiment of the needle assembly of FIG. 1A.
FIG. 1C illustrates an enlarged perspective view showing a distal end of the needle assembly of FIG. 1B.

In some embodiments, the needle assembly 100 can include a guide 108. The guide 108 can include one or more anchors 120 at a distal end for anchoring into tissue and/or bone at a surgical location. For example, the one or more distal anchors 120 can be configured to anchor into a facet joint. As shown in FIGS. 1A and 1B, in certain embodi-ments, the anchors 120 can include one or more prongs, teeth, etc., for example, two prongs, three prongs, four prongs, or any other suitable number of prongs. FIG. 1C is an enlarged view showing the distal anchors 120. In some embodiments, a force can be applied to the needle assembly, for example to a proximal end of the needle assembly 100 or to an impact handle, such as impact handle 130 shown in FIG. 3, for example via a mallet, to drive the anchors 120 into a surgical location, such as a facet joint.

The guide 108 can include a lumen configured to receive one or more instruments and/or implants for advancing the instruments and/or implants to a surgical location. The lumen can extend between an opening 134 at a proximal end of the guide 108 and an opening 136 at a distal end of the guide 108. In some embodiments, the guide 108 can receive the dilator 106 within the lumen of the guide 108. In some embodiments, the needle assembly 100 can be advanced to the surgical location while the dilator is positioned within the guide 108. The dilator 106 can be configured to prevent tissue from getting caught within the guide 108. In some embodiments, the guide 108 may include a handle or a knurled or smooth portion 138 for gripping by a user. In some embodiments, the knurled or smooth portion 138 may have a circumference greater than a distal section of the guide 108. Alternatively, the knurled or smooth portion 138 may have the same circumference as a distal section of the guide 108.

In some embodiments, the guide 108 can couple to the dilator 106 and/or stylet 112 through one or more threads, notches, bumps, or any other suitable connection mechanism. In other embodiments, the guide 108 can have a loose fitting with the dilator 106 and/or stylet 112 to allow the guide 108 to easily slide on and off of the dilator 106 and/or stylet 112 so the guide 108 can be used with other instruments, such as a drill bit or an implant.

Figure 5A:
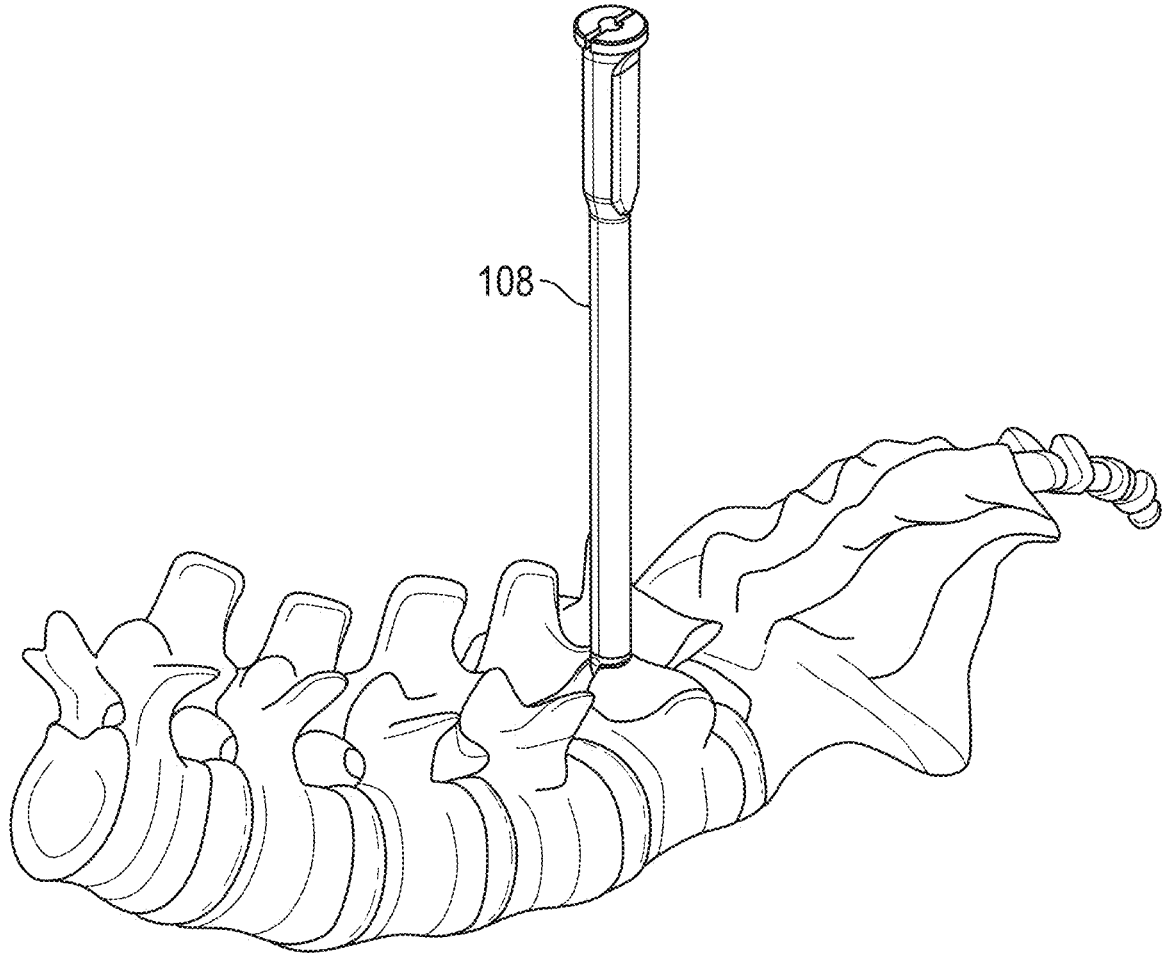
FIG. 5A illustrates a perspective view of an embodiment of a guide of a needle assembly positioned within a facet joint.
Figure 5B:
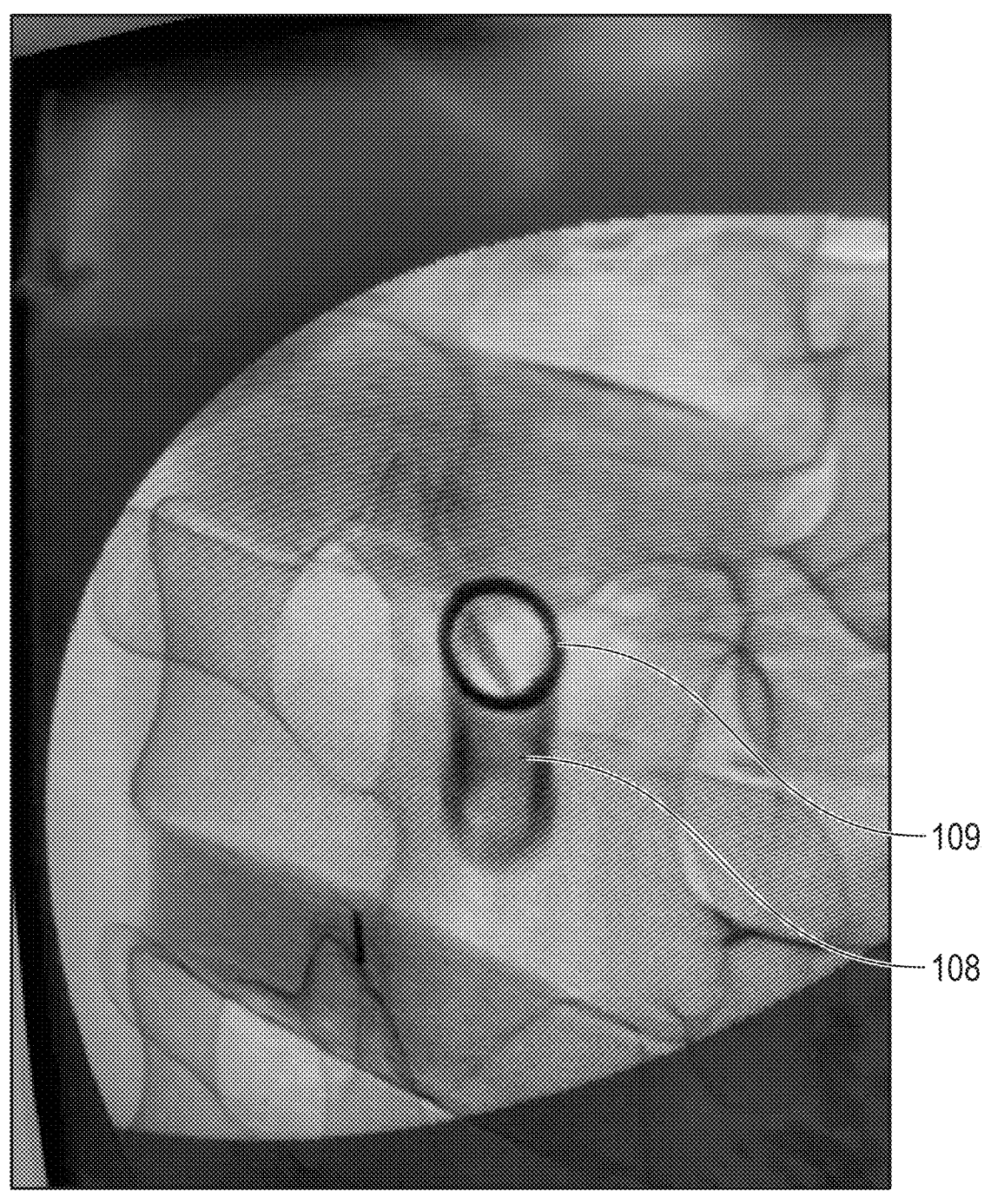
FIG. 5B illustrates an example of an x-ray of a guide of a needle assembly.

In some embodiments, the cannula shaft 118 and stylet shaft 112 may be metallic. In some embodiments, the needle assembly 100 can be used for neuromonitoring, for example, when the needle assembly 100 is positioned within the facet joint. In some embodiments, a cable or wire can be attached to the assembly 100 such that a current from a neuromonitoring device can be transmitted through the cannula shaft 118 and/or stylet shaft 112. The neuromonitoring device can provide data to a user, such as proximity of a portion of the needle assembly 100, such as the distal tip 114, to a nerve. If the portion of the needle assembly 100 is too close to the nerve, the user can adjust the position of the needle assembly 100. Other components of the needle assembly 100, such as the stylet handle 110, the cannula handle 116, the dilator 106, and/or the guide 108, may be formed of a non-metallic material that does not conduct electricity. Use of non-metallic and non-conductive material for the components outside of the cannula shaft 118 and stylet shaft 112 can allow for neuromonitoring. For example, the non-metallic and non-conductive materials can prevent current from shunting and prevent false readings. Use of a non-metallic guide 108 can also prevent image distortion when the guide 108 is positioned over the facet joint. A radiopaque guide 108 may prevent imaging of the facet joint. In some embodiments, the guide 108 can be radiolucent. In some embodiments, the guide 108 can be partially radiolucent and partially opaque. For example, FIG. 5B depicts an example of an X-ray of a guide 108 having a radiolucent body and a radiopaque distal end 109. The radiopaque distal end 109 can form a halo or bullseye on an X-ray image that can be positioned over the facet joint when the guide 108 is properly aligned. The halo or bullseye can allow the user to ensure proper alignment before drilling or reaming the facet joint and placing an implant to prevent implant malposition. In some embodiments, the radiopaque end 109 can be in the form of a plurality of teeth.

Additional details regarding needle assemblies and components and accessories thereof that may be used in the embodiments described herein are described in U.S. Pat. No. 9,681,889, which is incorporated by reference herein in its entirety and for all purposes, and in U.S. Pat. No. 9,968,373, which is incorporated by reference herein in its entirety and for all purposes.

Although a needle assembly 100 is described herein, in certain embodiments, an instrument assembly having only some of the features of the needle assembly may be used to implant an implant as described herein. For example, the instrument assembly may include only a guide 108, only a guide 108 and a dilator 106, or any other combination of instruments of the needle assembly 100.

FIGS. 2-8 illustrate the use of the needle assembly 100 in a procedure for implanting an implant within surgical location, such as a facet joint.

In a procedure for implanting an implant, the needle assembly 100 can be advanced to the surgical location, such as a facet joint, in an assembled configuration with each of the stylet 102, cannula 104, dilator 106, and guide 108 assembled together. In certain embodiments, the needle assembly 100 can be assembled prior to introduction into the body so that the stylet 102, cannula 104, dilator 106, and guide 108 can be placed within the body assembled together. In other embodiments, one or more of the stylet 102, cannula 104, dilator 106, and guide 108 can be advanced to the surgical location individually. In certain embodiments, the anchors 120 of the guide 108 can be anchored into tissue or bone at the surgical location, such as the facet joint (e.g., to secure the position of the needle assembly 100 relative to the surgical location). The tip 114 of the stylet 102 can be driven to penetrate tissue and/or bone at the surgical location.

Figure 2:
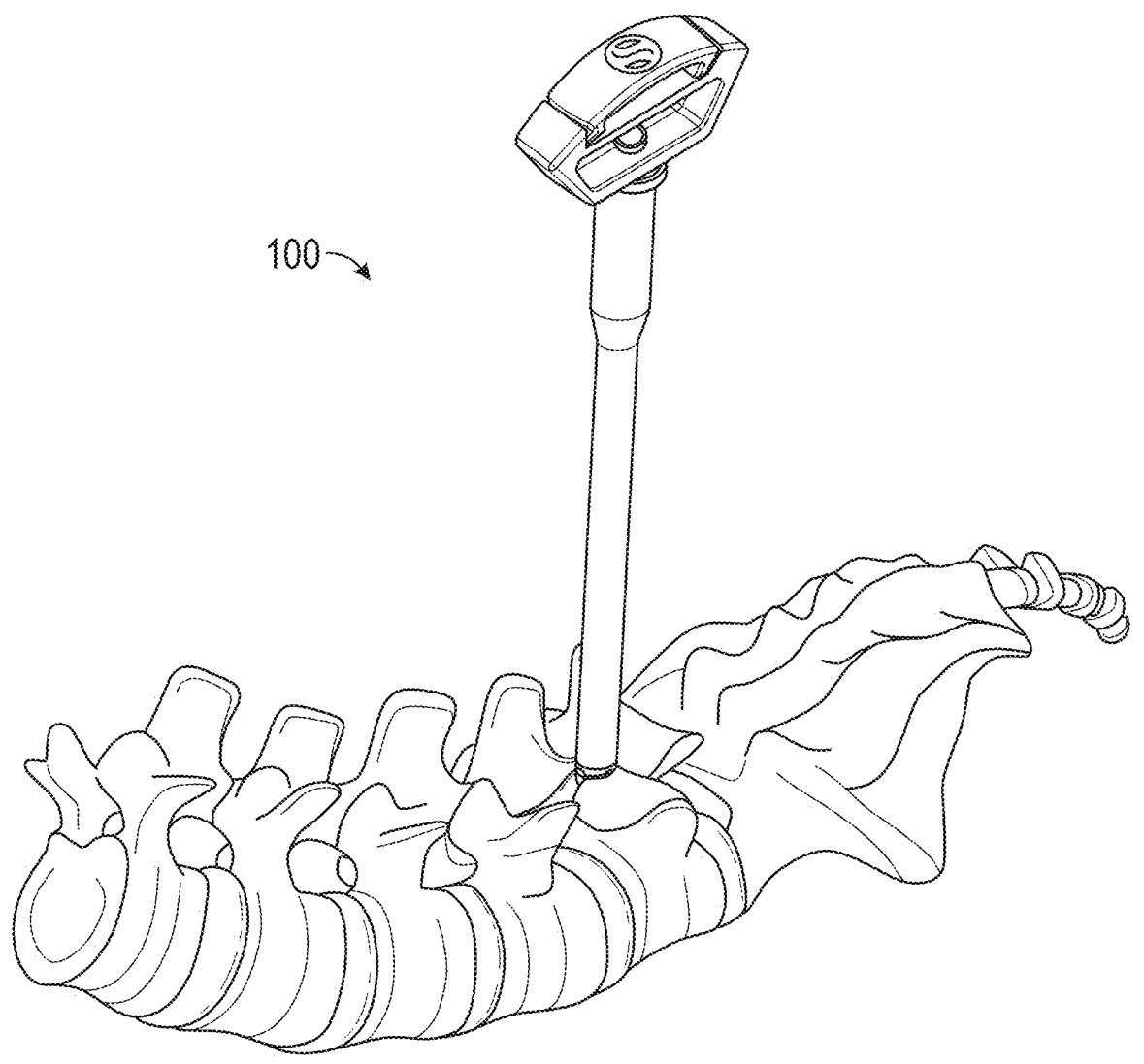
FIG. 2 illustrates a perspective view of an embodiment of a needle assembly positioned in a facet joint.

FIG. 2 shows the needle assembly 100 with a distal end of the needle assembly 100 positioned within the facet joint.

Figure 3:
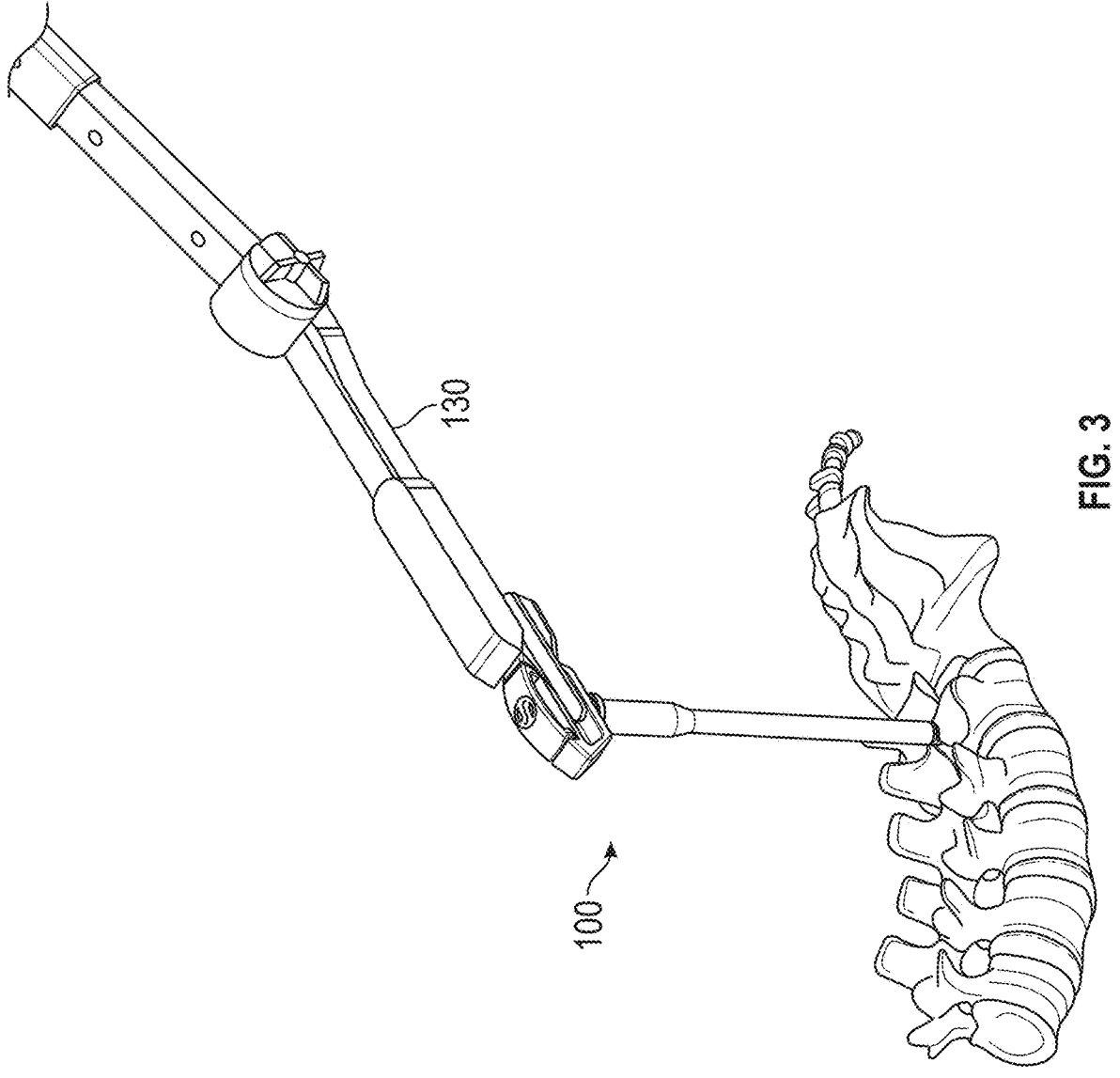
FIG. 3 illustrates a perspective view of an embodiment of a needle assembly positioned in a facet joint and an impact handle.

As shown in FIG. 3, in certain embodiments, an impact handle 130 can be coupled to the needle assembly 100. In some embodiments, the impact handle 130 can be coupled to the cannula 104, for example, to the cannula handle 116, and/or to the stylet 102, for example to the stylet handle 110. The impact handle 130 can allow a user to, for example, maneuver, control the direction of, hold, and/or mallet the needle assembly 100 more easily and/or while keeping his or her hands away from the radiation and out of the way of imaging and/or other equipment. The impact handle 130 can also allow the user to maneuver or manipulate the needle assembly 100 as needed during the surgical procedure. In certain embodiments, the impact handle 130 can be malleted to drive the tip 114 into tissue and/or bone at the surgical location, such as the facet joint. In certain embodiments, the tip 114 can form a pilot hole. The tip 114 can penetrate tissue while advancing the assembly 100 to the surgical location.

Figure 4:
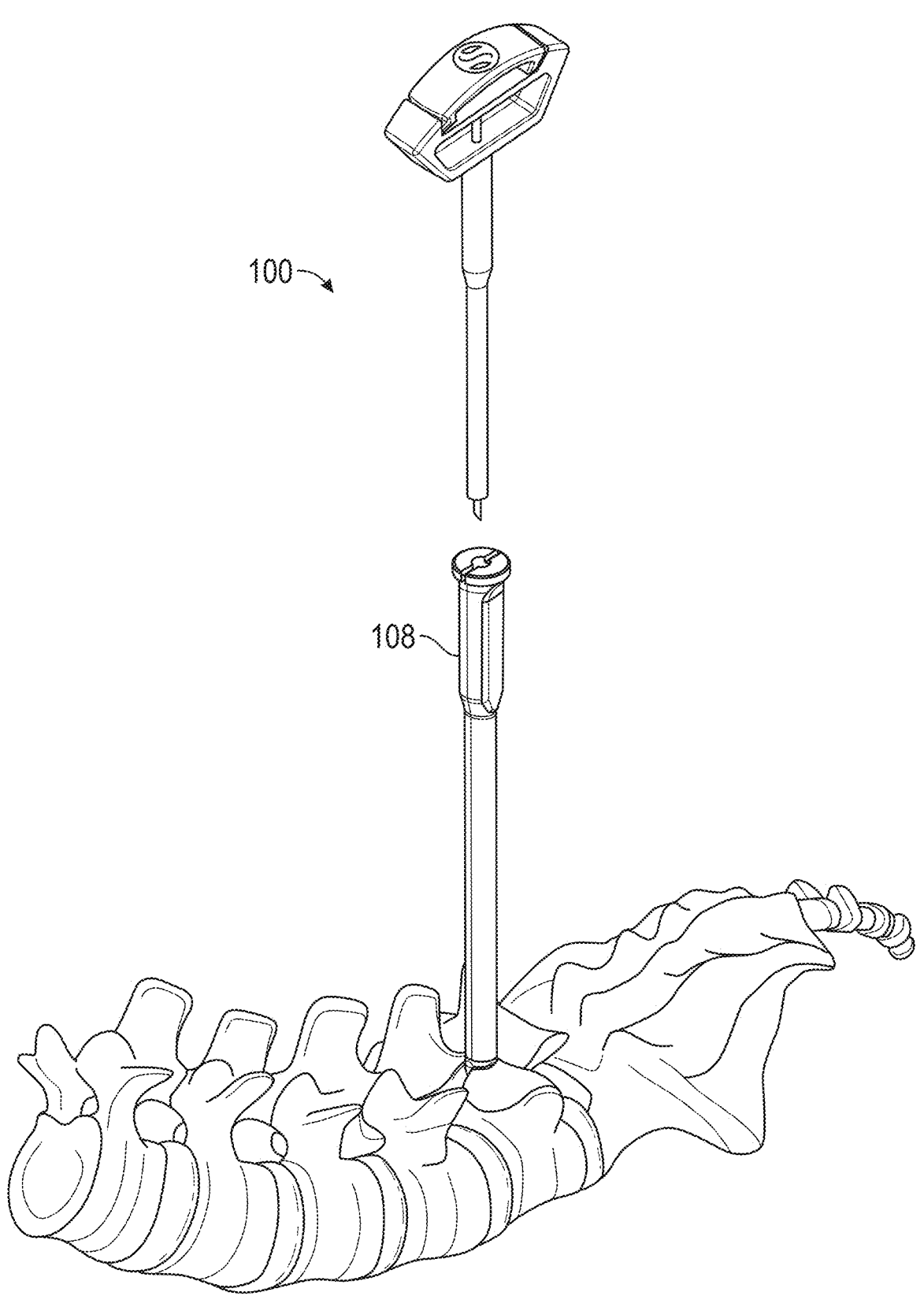
FIG. 4 illustrates a perspective view of an embodiment of a needle assembly showing a guide positioned within a facet joint and other components of the needle assembly removed from the guide.

As shown in FIG. 4, after the guide 108 is anchored into the facet joint via the anchors 120, the dilator 106, the cannula 104, and the stylet 102 can be removed from the guide 108. FIG. 5A shows the guide 108 anchored into the facet joint after removal of the dilator 106, the cannula 104, and the stylet 102 from the guide 108.

After removal of the dilator 106, the cannula 104, and the stylet 102, the guide 108 can be used to advance one or more instruments and/or implants to the facet joint. As described above and shown in FIG. 5B, in some embodiments, the guide 108 can be radiolucent with the radiopaque end that can be used to align the guide 108 with the facet joint for proper alignment of the one or more instruments and/or implants.

Figure 6:
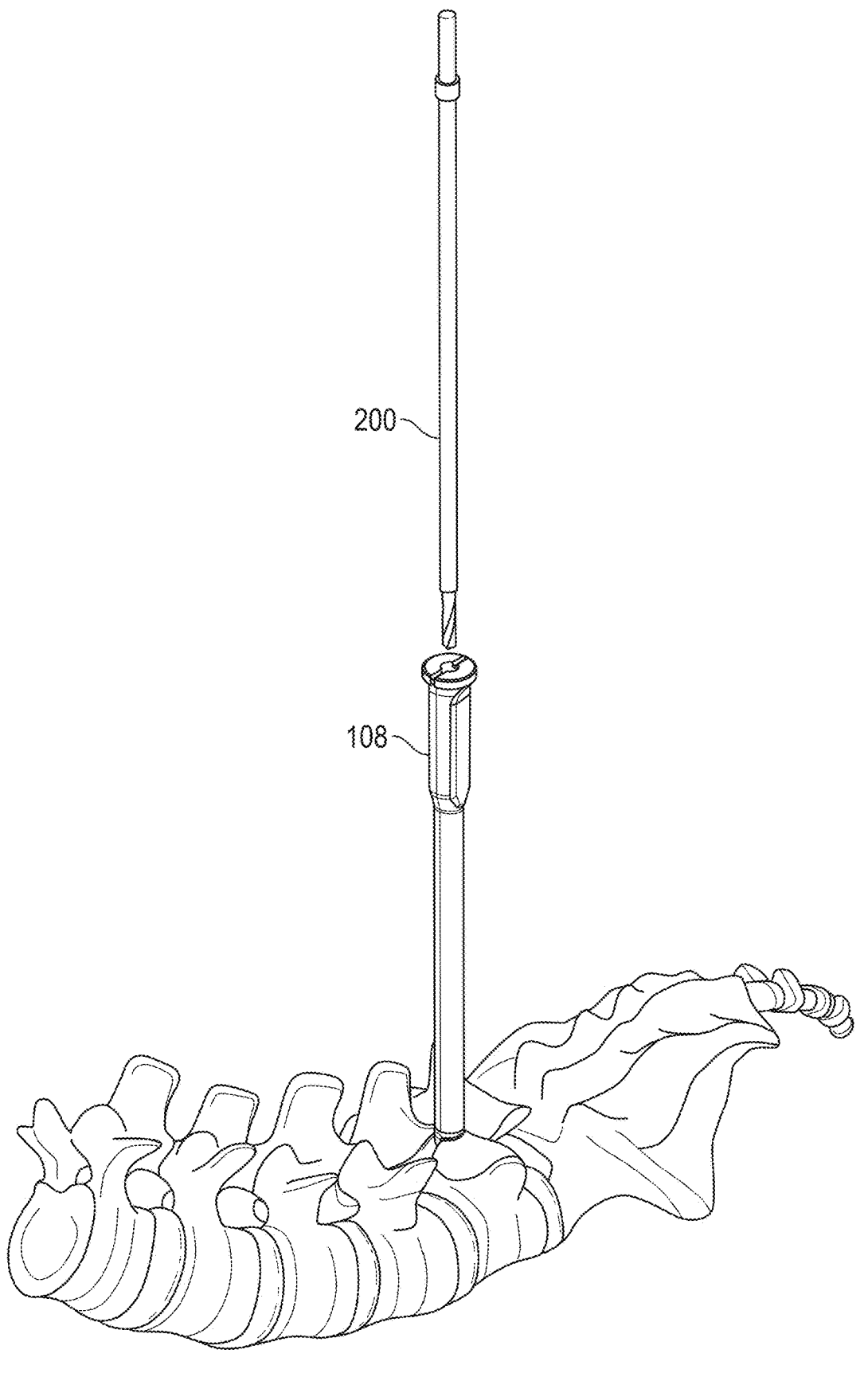
FIG. 6 illustrates a perspective view of an embodiment of a guide of a needle assembly positioned within a facet joint and a drill bit.

As shown in FIG. 6, a drill bit 200 can be advanced through the guide 108 and into the facet joint for drilling a pilot hole for an implant, as described in further detail herein. The drill bit 200 can be used to form a pilot hole at a predetermined depth to allow an implant to be safely inserted into a surgical location, such as a facet joint, at a desired depth to sit flush or countersunk within the surgical location, as described in further detail herein. A predetermined depth can prevent neurologic injury caused by drilling too deep. The average depth of a facet joint is 15 mm. In certain embodiments, the drill bit 200 may contain a drill stop so that the bit can be advanced to a pre-determined depth. The drill bit 200 can be driven using a handle or drill.

The drill bit 200 can be a standard set diameter to drill uniformly into a surgical location, such as the facet joint. In other embodiments, the drill bit 200 may contain multiple widths (diameters). A drill bit 200 with multiple diameters can allow formation of a pilot hole for the implant using a distal section of the drill bit 200 with a set diameter and also allow for formation of an area configured to be positioned above the implant when the implant is positioned in the pilot hole for fusion to take place above implant by reaming using a proximal section of the drill bit. The proximal section of the drill bit may contain various patterns of blades, cutting flute, teeth, reamers, knurling, or any other suitable patterns that can create an area of decortication above the implant and/or over the facet joint. In certain embodiments, after the pilot hole is drilled within the joint or other surgical location at a fixed circumference, a crown or other pattern at a proximal section of the drill will ream a socket or area above the pilot hole. Examples of drill bits having multiple diameters are discussed with respect to FIGS. 16A-C.

Figure 7:
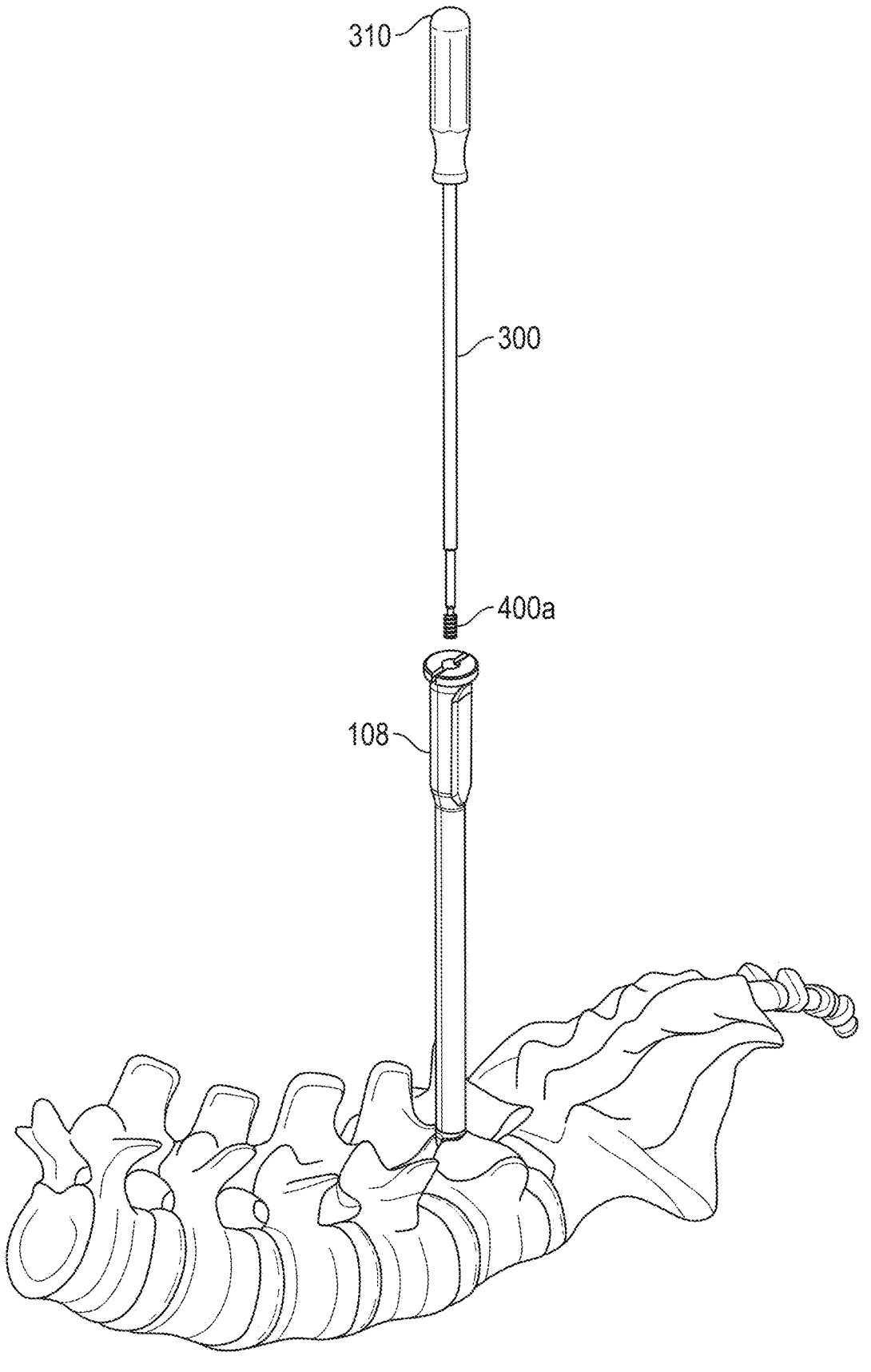
FIG. 7 illustrates a perspective view of an embodiment of a guide of a needle assembly positioned within a facet joint and an inserter.
Figure 8:
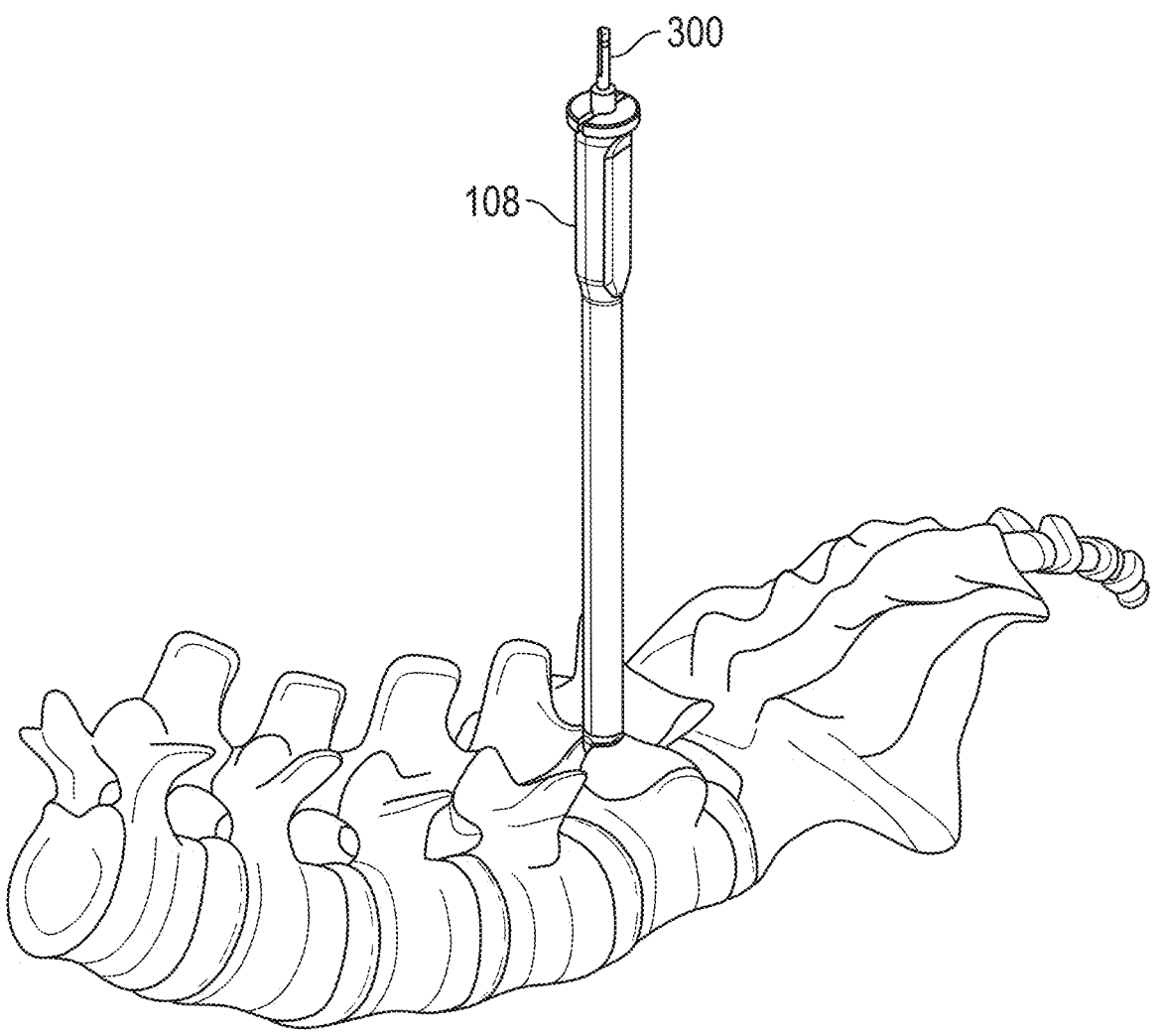
FIG. 8 illustrates a perspective view of an embodiment of a guide of a needle assembly and inserter showing the inserter positioned within the guide.

In some embodiments, after a pilot hole is drilled, for example, an inserter 300 can be used to deliver an implant through the guide 108 and to the facet joint, as shown in FIGS. 7 and 8.

In certain embodiments, only some of the steps of the procedure described with respect to FIGS. 2-8 may be performed for implanting an implant. For example, in certain embodiments, an implant may be implanted without using a stylet 112 and/or without using a drill bit 300 to form a pilot hole.

Figures 9A, 9B, 9C:
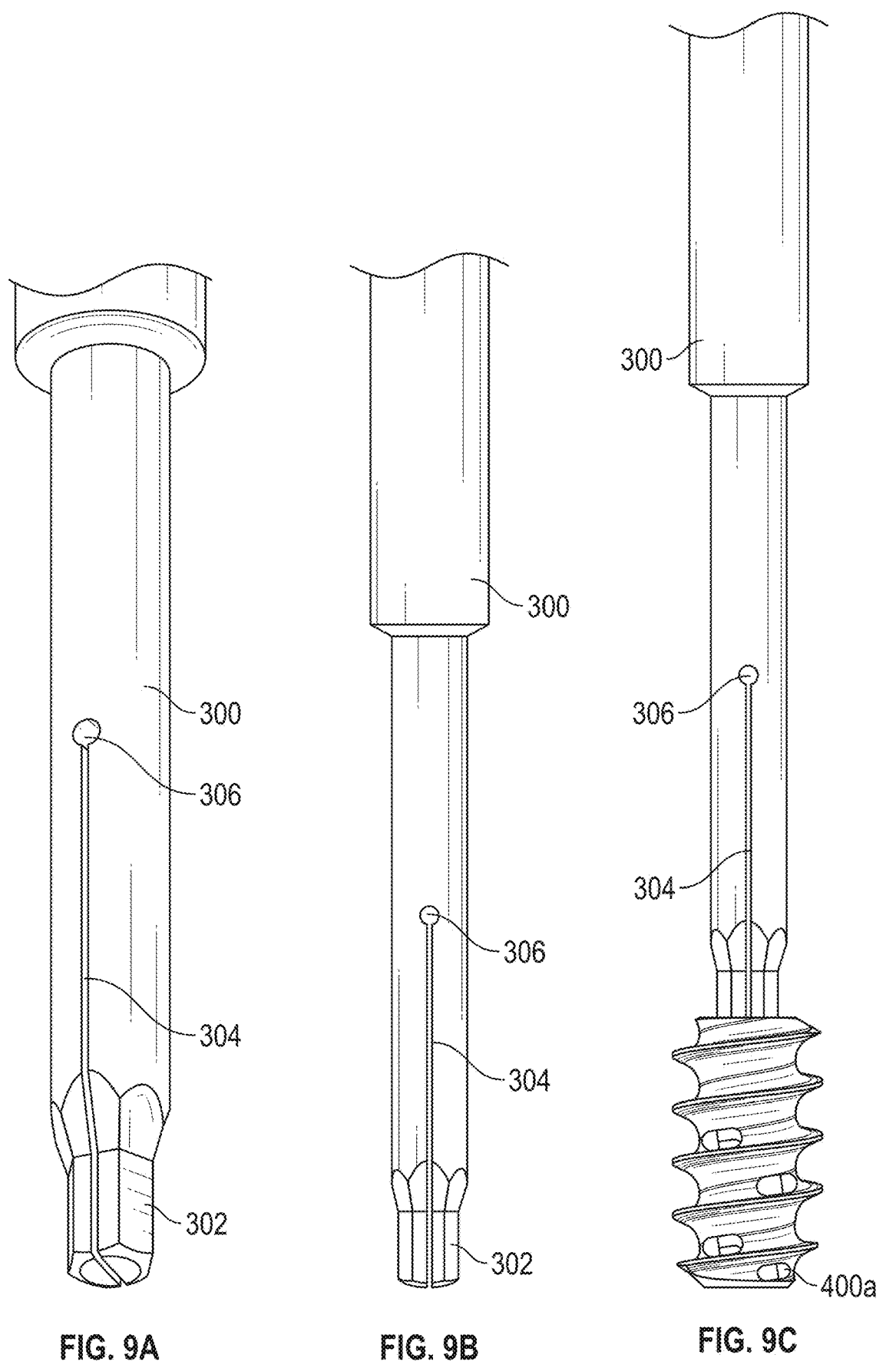
FIG. 9A illustrates an enlarged perspective view of an embodiment of a distal end of an inserter.
FIG. 9B illustrates an enlarged front view of the inserter of FIG. 9A.
FIG. 9C illustrates an enlarged front view of the inserter of FIG. 9A coupled to an implant.

FIGS. 9A and 9B illustrate a distal portion of the inserter 300. The inserter 300 can include distal tip 302 configured to couple with an implant, such as an intrafacet implant, facet screw, facet dowel, pedicle screw, cortical screw, or any other suitable implant. The inserter 300 can include a split 304 extending through the distal tip 302. The split 304 can extend proximally through a body of the inserter 300 to a relief 306. The relief 306 may be a cut-out region within the body of the inserter 300 at a proximal end of the split 304. The relief 306 may be in the shape of a circle or any other suitable shape.

The split 304 and relief 306 allow for the distal tip 302 to compress when an implant, such as a screw, is positioned thereon. FIG. 9C illustrates an embodiment of an implant 400a coupled to the inserter 300.

After the implant is positioned on the distal tip, the compressed distal tip will apply outward forces against the implant to prevent of inhibit premature disengagement of the implant from the inserter 300.

The distal tip 302 can have any shape suitable for coupling to an implant, such as a screw. For example, the distal tip 302 can have a hex pattern, star pattern, square pattern, torx pattern, or any other suitable shape.

In some embodiments, the tip 302 can be coupled to an implant, such as a screw, via a quick release coupling. In some embodiments, the tip 302 can be coupled to an implant, such as a screw, such that the tip 302 can disengage from the implant by pulling proximally on the driver or by exerting a force on the driver in a direction opposite of the insertion direction. Such a coupling may forego the need for additional release mechanisms. In some embodiments, the tip 302 can couple to the implant via a press fit. In some embodiments, the coupling can allow for removal of both the guide 108 and the inserter 300 together. For example, in some embodiments, pulling proximally on the guide 108 in an upward direction or direction opposite of the insertion direction can cause the inserter 300 to disengage from the implant and be removed with the guide 108. In some embodiments, after the inserter 300 bottoms out of the guide 108 and the implant is driven into bone, the driver or inserter 300 can be removed with the guide 108 from the implant.

Figure 9D:
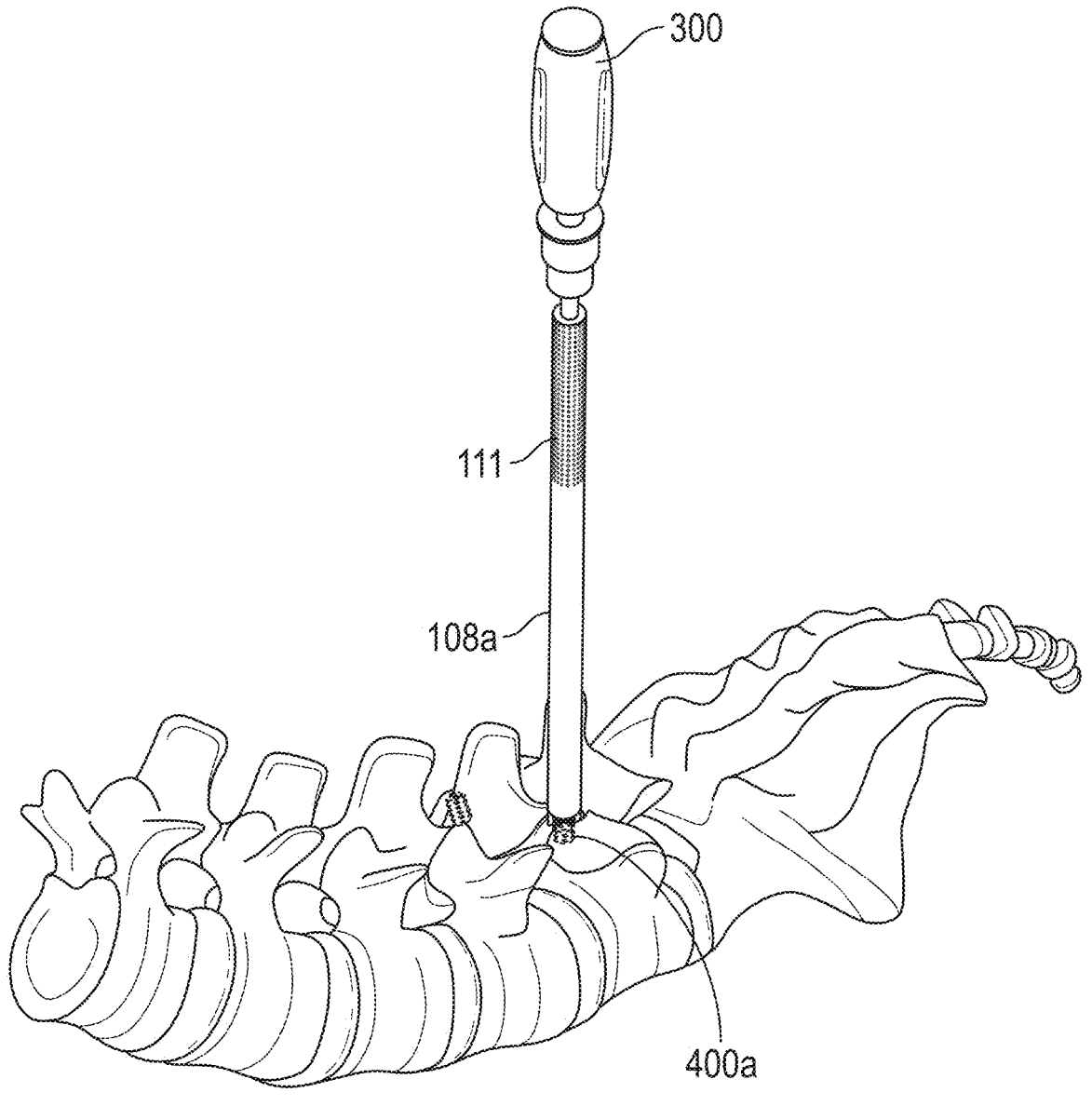
FIG. 9D illustrates a perspective view showing an embodiment of a guide, an inserter, and an implant positioned within a facet joint.
Figure 9E:
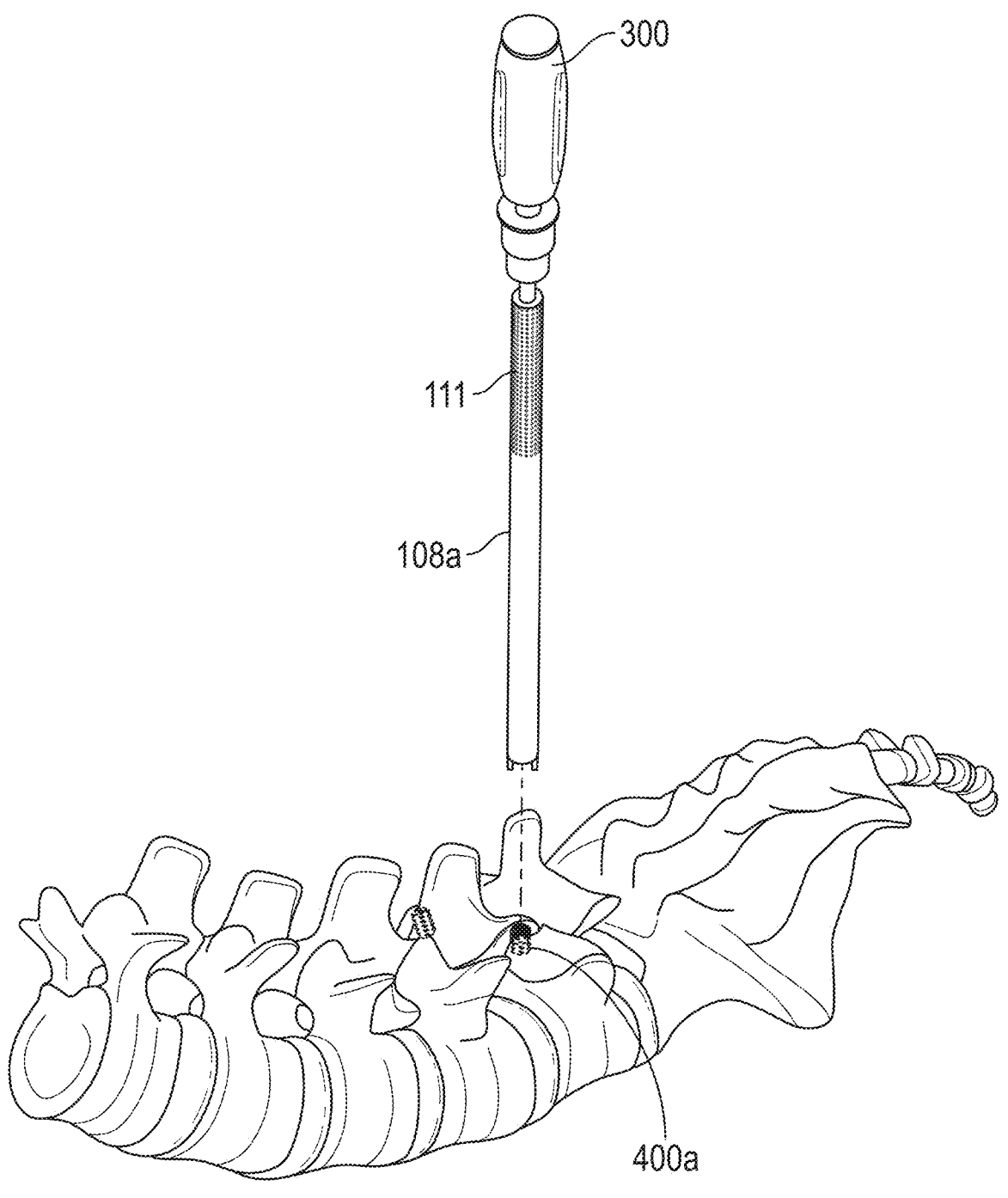
FIG. 9E illustrates a perspective view showing an embodiment of a guide, an implant, and an inserter, with the implant positioned within a facet joint.

FIG. 9D depicts the inserter 300 and an alternative embodiment of a guide 108a with the inserter 300 coupled to the implant 400a after implantation of the implant 400a. The guide 108a can include any of the same of similar feature or functions as the guide 108. The guide 108a can may also include a textured section 111 which may be used as a handle. The guide 108a can be used to perform any of the functions described with respect to the guide 108a, and the guide 108 can be used to FIG. 9E depicts an example of the inserter 300 and guide 108a after the inserter 300 and guide 108a are removed together from the body. Removal of the inserter 300 and guide 108 together can save time and reduce steps during surgery.

As shown in FIG. 7, the inserter 300 can have a handle 310. In some embodiments, the handle 310 can be removable. The handle 310 can couple to the body of the inserter 300 through a snap-on engagement, quick disconnect, or any other suitable engagement. In some embodiments, the handle 310 can be integrally formed with the inserter body as a single piece. The handle 310 can be a ratcheting or non-ratcheting handle. The handle 310 can be a straight handle, a t-handle, egg handle, or any other suitable handle type. In some embodiments, the handle 310 can have a grip. For example, the handle 310 can have a rubber or silicone grip to facilitate gripping by the surgeon. In other embodiments, the handle 310 may have a smooth section for grasping by the surgeon. The inserter 300 can be used to place the implant at a predetermined depth.

In certain embodiments, the inserter 300 may be cannulated from a proximal end to a distal end. The cannula of the inserter 300 can be configured to receive bone graft material and may be used to deliver bone graft material to an implant or surgical location.

Figure 10:
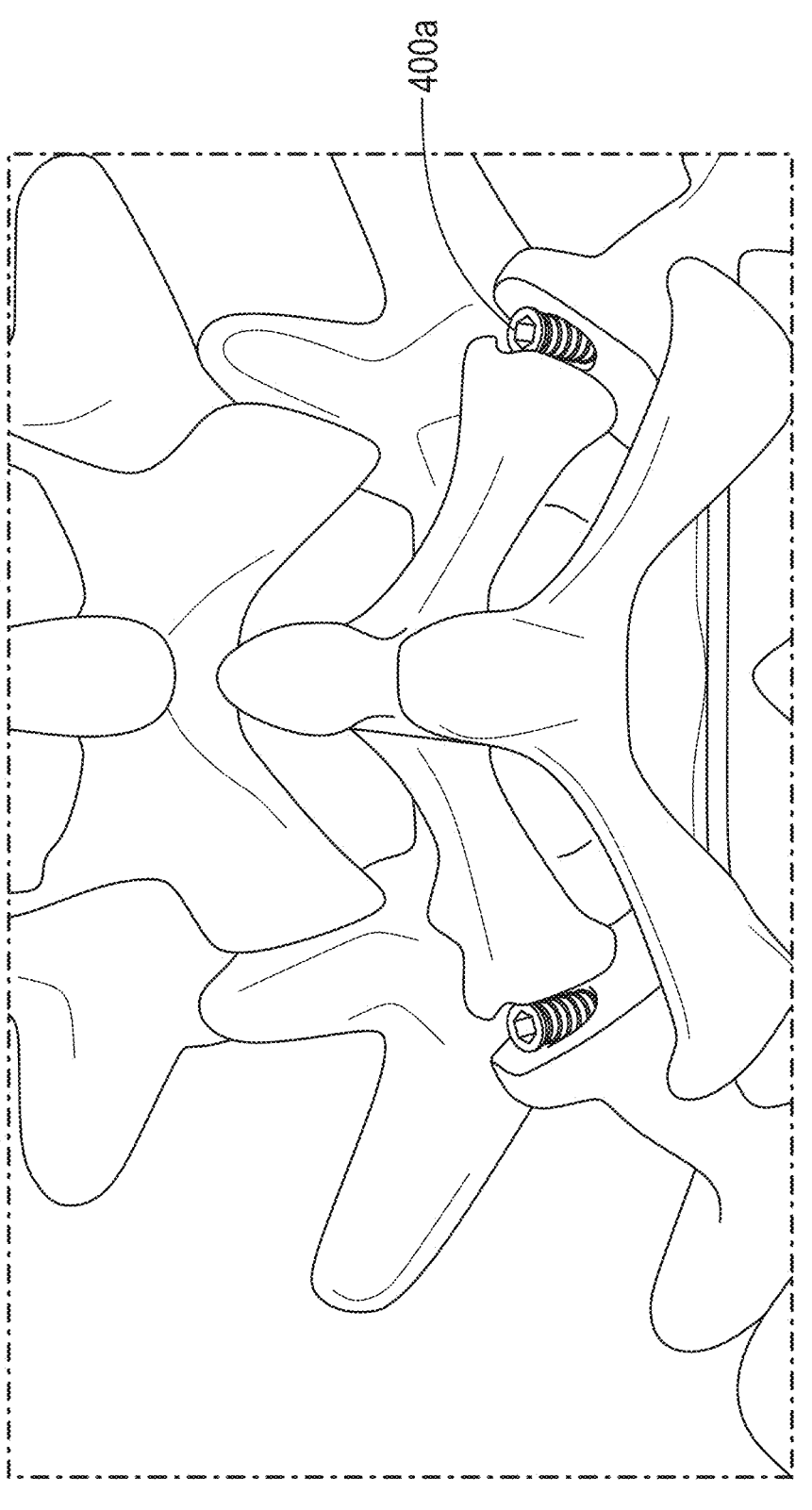
FIG. 10 illustrates a perspective view showing embodiments of implants positioned within facet joints.

FIG. 10 illustrates a pair of implants 400a positioned within the facet joints of a vertebral body. As shown in FIG. 10, the implant 400a can be flush with or countersunk within the facet joint. In other words, the implant 400a can be positioned within the facet joint such that no portion of the implant 400a extends above the facet joint. In some embodiments, for example, a pilot hole can be formed over a distance that is the same as or greater than a length of the implant 400a. For example, a pilot hole 11 mm in depth can be formed for an implant 400a having a length of 10 mm. The implant depth can be between 5 mm to 14 mm to safely fit within a pilot hole and to allow for bone encapsulation as described herein. The implant 400a can be driven into the pilot hole until the implant 400a bottoms out.

After the implant is inserted into the joint, a rasp can be used to create a larger surface area for bone fusion. With an implant that is flush with or countersunk within the facet joint, a rasp, drill, or other means of decortication can be used to decorticate over the entirety of the joint line of the facet joint without contacting the implant 400a to promote fusion. In some embodiments, bone graft can be distributed over the joint and implant, for example, after rasping the joint line. Further, an implant that is flush or countersunk with the facet joint will prevent or reduce contact with other tissues such as muscle that may cause chronic pain or inflammation. Additionally, encapsulation of the implant 400a with bone can seal off the implant from other soft tissues. In contrast to the implants described herein, it is well known that traditional pedicle screws and facet screws have a profile which extends higher than their insertion point into bone, which may cause irritation and require removal. If an implant is proud of the facet joint, the rasp may get caught on the implant or dislodge the implant. Further, the materials, such as metals, of an implant that contacts external tissues may cause an allergic reaction.

Figure 21A:
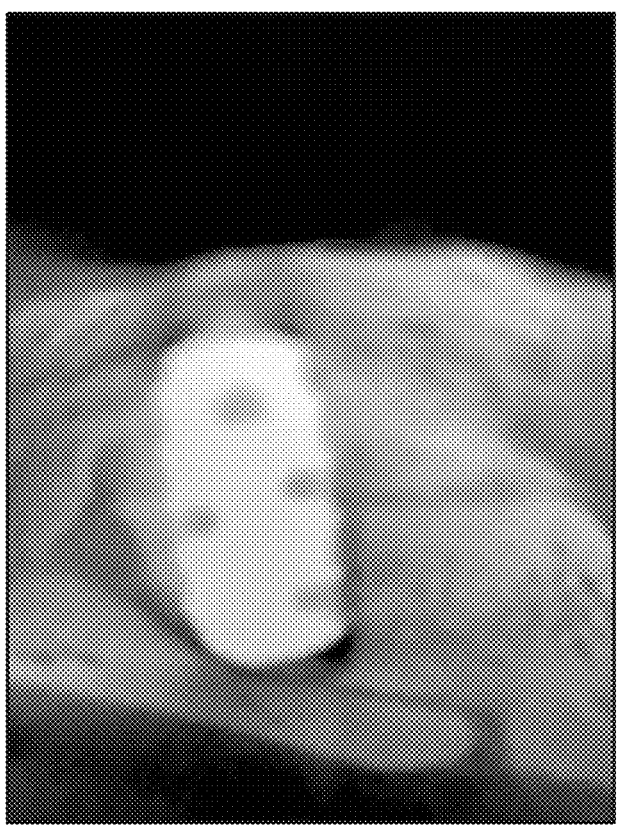
FIG. 21A illustrates an example of an implant encapsulated in bone.

After the implant is placed within the surgical location to a predetermined depth, bone graft (allograft, autograft, synthetic bone graft, or any other suitable graft) can be placed over the top of the implant to encapsulate the implant. The bone graft can be placed using the rasp or after the rasp is removed by a graft delivery device, funnel, or by hand. An implant that is flush with or countersunk within the facet joint may allow for bone growth that encapsulates the implant in bone, for example, as shown in FIG. 21A. Encapsulation can seal the implant within the bone to prevent or inhibit contact with other soft tissues such as muscle, ligaments, cartilage, etc. The encapsulation will also resist the back out of the implant. Traditional orthopedic implants and screws have been known to migrate or pull out in some instances. With the formation of a section of bone, for example a bridge of bone, above the implant, the implant is less likely to back out or expulse.

Figure 11B:
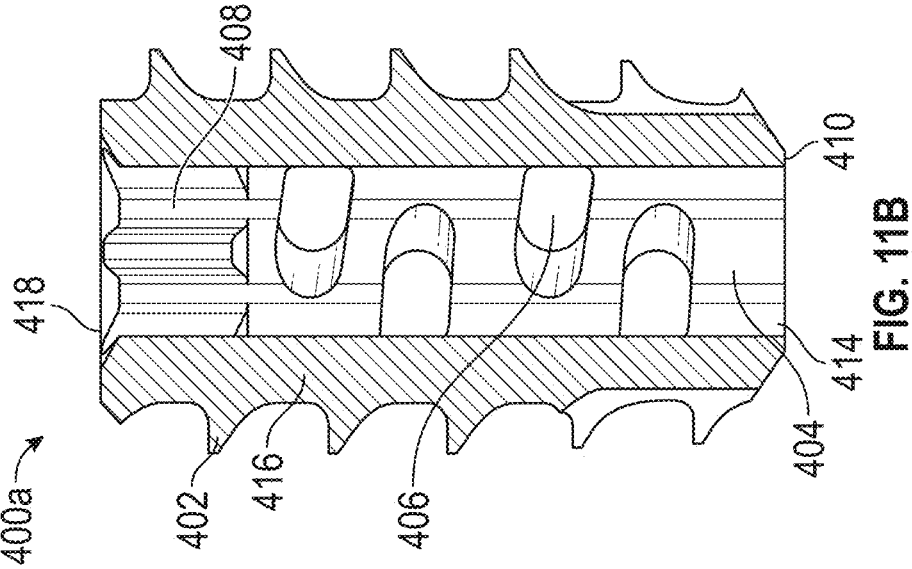
FIG. 11B illustrates a cross-sectional view of the implant of FIG. 11A.
Figure 11A:
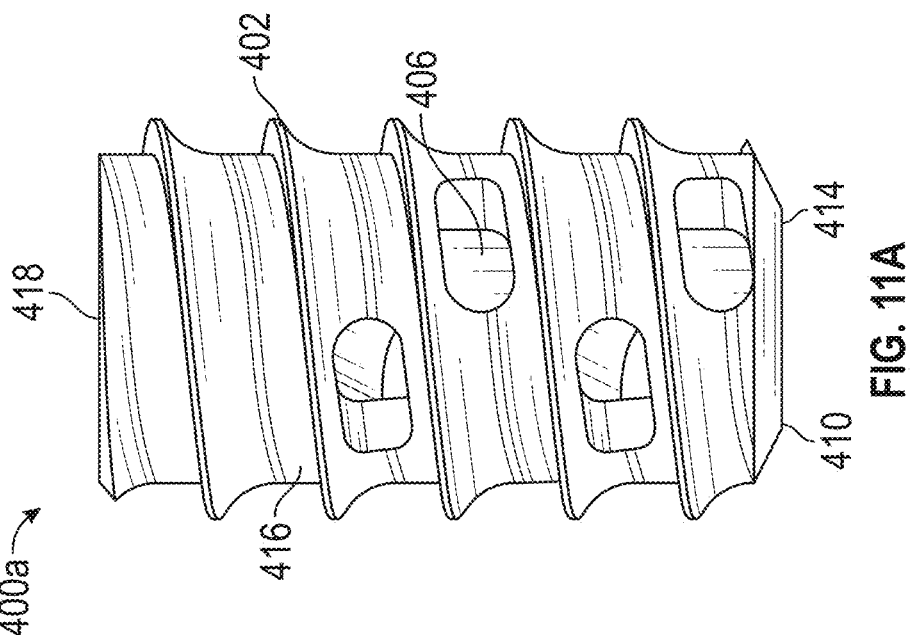
FIG. 11A illustrates a front view of an embodiment of an implant.

FIG. 11A illustrates the implant 400a. FIG. 11B illustrates a cross-sectional view of the implant 400a. In some embodiments, the implant 400a can be an intrafacet implant, such as an intrafacet screw. The implant 400a includes engagement features 402. The engagement features 402 can be in the form of threads extending between a proximal end 418 and a distal end 414 of the implant 400a. The implant 400a can be implanted within a facet joint. The engagement features 402 can be configured to engage a portion of a superior articular process and an inferior articular process to secure the facet joint with the implant 400a.

In some embodiments, the engagement features 402 can be in the form of helical threads. In some embodiments, the helical threads can provide joint compression and prevent implant migration and back out.

As shown in FIG. 11B, the implant 400a can be cannulated from the proximal end 418 to the distal end 414, having a channel 404 extending from the proximal end 418 to the distal end 414. In some embodiments, the channel 404 can allow for a guidewire to extend through the implant 400a.

In some embodiments, the implant 400a can be loaded with demineralized bone matrix (DBM), cortical fibers, synthetic bone matrix, BMP2 or BMP7, peptide graft, autograft or any combination thereof The implant 400a can include a plurality of openings or windows 406. The windows 406 can be in communication with the channel 404. The channel 404 can be packed and/or filled with bone graft material, which can flow through the windows 406 for introduction of the bone graft within the channel 404 to the facet joint. In some embodiments, the windows 406 can be offset relative to one another such that at least some of the windows 406 will align with the bone of the superior and inferior vertebral bodies so that graft flowing through the windows 406 will contact the bone regardless of the orientation of the implant 400a when fully seated within the facet joint.

In certain embodiments, the implant can be configured to be inserted with a driver, such as a hex driver, a star driver, a square driver, a torx driver, or any other suitable driver for driving the implant into bone. The proximal end 418 of the implant 400a can include an engagement feature 408 for coupling with an inserter as described herein. The engagement feature 408 may be a recess configured to couple with an inserter. The engagement feature 408 can be shaped to couple with a hex driver, a star driver, a square driver, a torx driver, or any other suitable driver for driving the implant 400a into bone.

As shown in FIGS. 11A and 11B, a tip 410 of the implant can be flat. As shown in FIGS. 11A-B, the implant 400a or a shank 416 of the implant can be untapered throughout the entire length of the implant or a portion of the length. For example, the shank 416 can have a uniform cross-section or a generally uniform cross-section. In some embodiments, the engagement features 402 (e.g., threads) can extend a uniform distance or generally uniform distance from the shank 416 throughout the length of the implant. Such untapered embodiments may further prevent or reduce migration or back out of the implant 400a from a surgical location in comparison to tapered implants. In some embodiments, the implant 400a can be self tapping or self drilling.

In some embodiments, the implant 400a can be textured by bead blasting, chemical etching, acid etching, 3D printing, coating such as hydroxyapatite (HA) or tricalcium phosphate (TCP), or any other suitable mechanism. Texturing of the implant 400a can help with fusion and bony integration.

The windows 406 can allow bone graft to flow through the implant 400a and contact bone for fusion. The windows 406 can come in a variety of shapes, sizes, and amounts. The windows 406 can include one or more circular windows, square windows, oblong windows and/or windows of any other suitable shape which can be positioned in strategic locations to assist with fusion and graft flow. In some embodiments, there may be only a single window 406. In other embodiments, the implant 400a can include 2, 3, 4, 5, 6, 7, 8, 9, or 10 or more windows. The one or more windows 406 can be strategically placed between/around/through the engagement features of the implant 400a.

As shown in FIGS. 11A-11B, in some embodiments, the implant 400a may be headless. In other words, in some embodiments, the implant 400a does not include a separate head having a different diameter than the shank 416. Instead, the proximal end 418 of the implant can have the same diameter, a similar diameter, or a smaller diameter than the shank 416 of the implant to facilitate countersinking of the implant 400a.

The implant 400a can be formed of titanium, stainless steel, or metal/alloy metal, biocompatible resorbable material, or other any other suitable synthetic implant material.

Figure 12B:
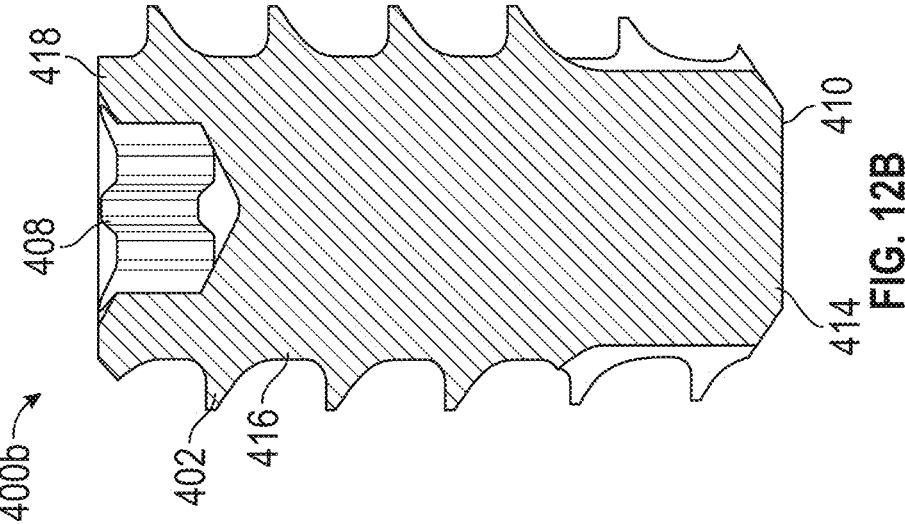
FIG. 12B illustrates a cross-sectional view of the implant of FIG. 12A.
Figure 12A:
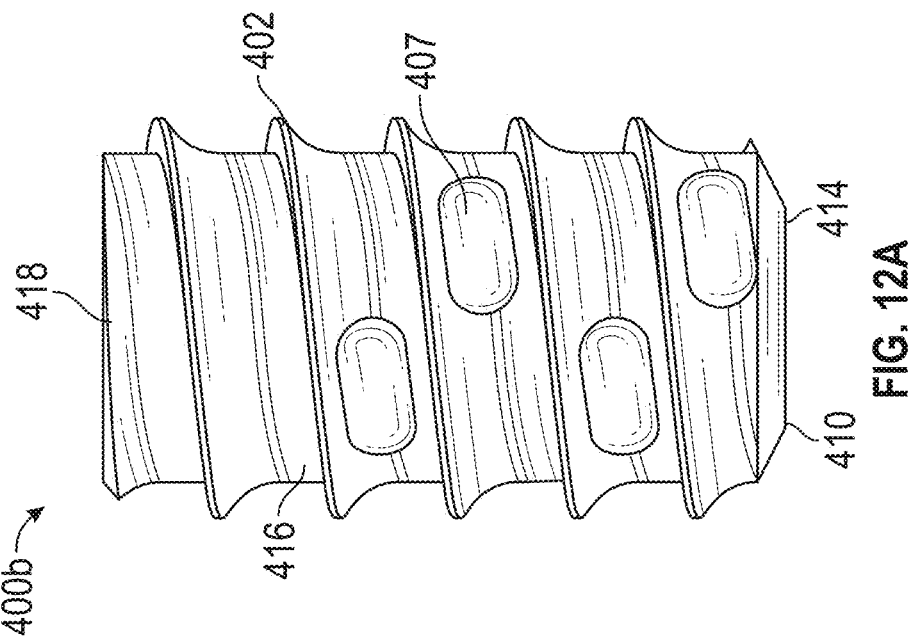
FIG. 12A illustrates a front view of an embodiment of an implant.

[0035] FIGS. 12A and 12B illustrate a front view and a cross-sectional view of an implant 400b. The implant 400b can generally include any of the same or similar functions and features as the implant 400a. In contrast to the implant 400a, the implant 400b is not cannulated. Further, instead of windows 406, the implant 400b includes notches 407 that extend only partially inwardly towards a central axis of the shank. The notches 407 can come in a variety of shapes, sizes, and amounts. The notches 407 can include one or more circular notches, square notches, oblong notches and/or notches of any other suitable shape which can be positioned in strategic locations to assist with fusion. In some embodiments, there may be only a single notch. The one or more notches 407 can be strategically placed between/around/through the engagement features of the implant 400b. The notches 407 can allow for bone growth therein so as to prevent or reduce migration or back out of the implant 400b. In some embodiments, the notches 407 can be offset relative to one another such that at least some of the notches 407 will align with the bone of the superior and inferior vertebral bodies to facilitate bone growth within the notches

407 regardless of the orientation of the implant 400b when full seated within the facet joint.

Figure 13B:
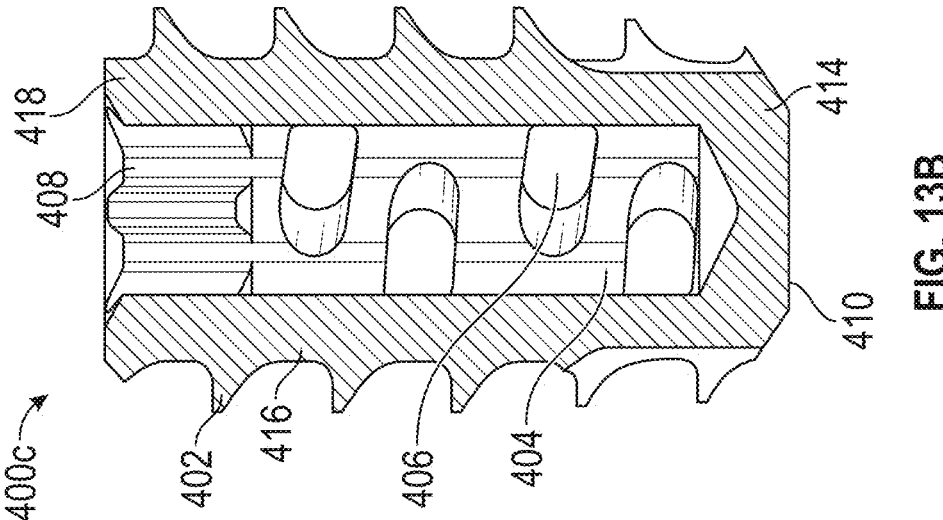
FIG. 13B illustrates a cross-sectional view of the implant of FIG. 13A.
Figure 13A:
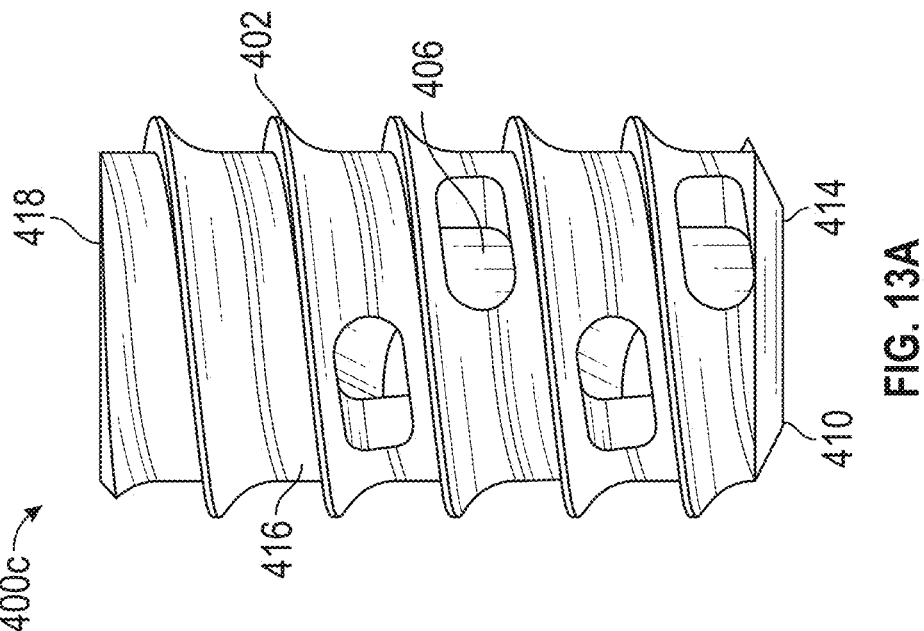
FIG. 13A illustrates a front view of an embodiment of an implant.

FIGS. 13A and 13B illustrate a front view and a cross-sectional view of an implant 400c. The implant 400c can generally include any of the same or similar functions and features as the implant 400a. In contrast to the implant 400a, the implant 400c is cannulated through only a portion of the length of the implant 400c from the proximal end 418 towards the distal end 414. The implant 400c has a closed distal end as shown in FIGS. 13A and 13B.

In some embodiments, an implant that is only partially cannulated, such as implant 400c, may have a higher biomechanical strength than an implant that is cannulated throughout its entire length, such as implant 400a. An implant that is not cannulated, such as implant 400b may have a higher biomechanical strength than a partially or fully cannulated implant. An implant that is not cannulated, such as implant 400b may have a greater cantilever test and/or torque test in comparison to an implant that is partially or fully cannulated.

Figure 21B:
FIG. 21B illustrates an example of bone ingrowth within implants within the facet joints.

In some embodiments it may be desirable for the channel 404 of the implants 400a and 400c to have a diameter large enough to receive bone graft, but small enough to avoid or inhibit deformation of breakage due to fragility. The diameter must also be sufficiently small for the implant to fit in a desired anatomic location, such as the facet joint. In some embodiments, the diameter of the channel 404 is between 1.6 mm and 4 mm. A diameter less than 1.6 mm may prevent graft from flowing within or being packed into the channel 404. A diameter greater than 4 mm may result in an implant with insufficient mechanical strength, which can lead to breakage. An image of a CT scan showing bone ingrowth within an implant fusing through the facet joints is shown in FIG. 21B. The channel of the implant used in the CT scan featured in FIG. 21B was 2.5 mm in diameter. Internal bone growth can be desirable for fusion of implant to surrounding bone to prevent non-unions.

In some embodiments, the implant 400b may be advantageously used in the cervical spine, for example, where a smaller screw implant is required in comparison to other areas of the spine.

Figure 23B:
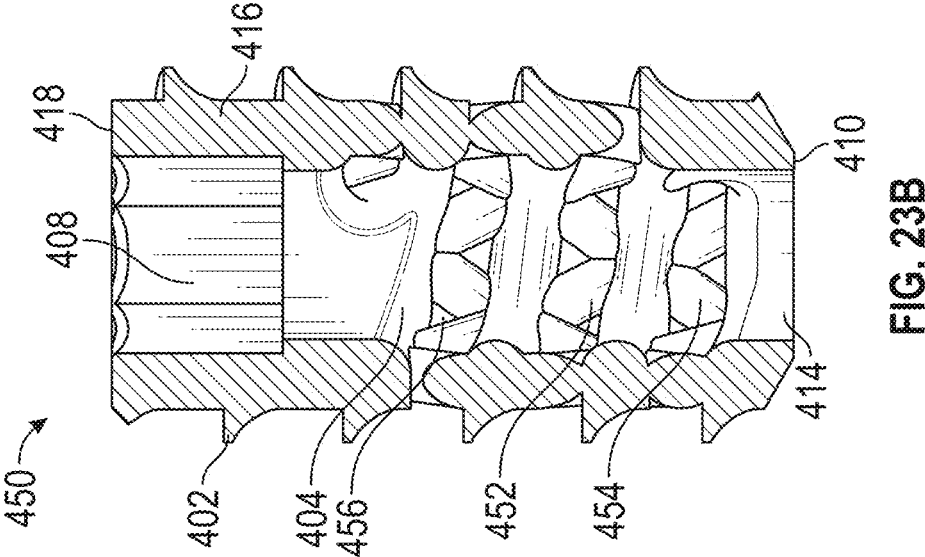
FIG. 23B illustrates a cross-sectional view of the implant of FIG. 23A.
Figure 23A:
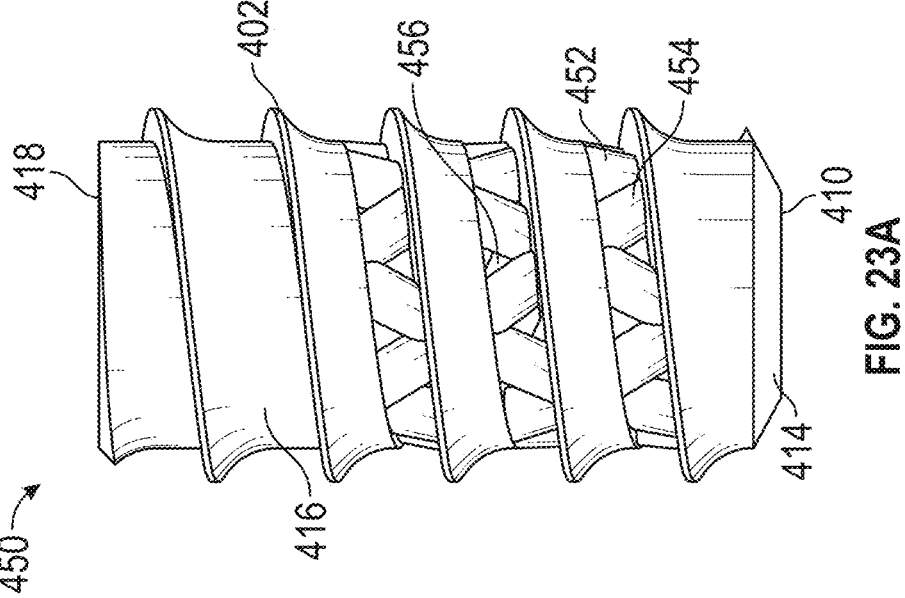
FIG. 23A illustrates a front view of an embodiment of an implant.

FIGS. 23A and 23B illustrate a front view and a cross-sectional view of an implant 450. The implant can generally include any of the same or similar functions and features as the implant 400a. In contrast to the implant 400a, the implant 450 includes a truss or beam system 452. The truss or beam system 452 can act as a scaffolding to provide increased biomechanical strength to the implant 450 and to facilitate bone growth. The truss or beam system 452 can allow for bone graft material to be packed into the implant 450 while facilitating fusion with surrounding bone. The truss or beam system 452 can also provide stability as the implant 450 fuses with the surrounding bone.

The truss or beam system 452 can be formed of a plurality of truss elements or beams 454. In some embodiments, the plurality of truss elements or beams 454 can extend between at least some of the engagement features 402. A number of windows or openings 456 can be formed between the truss elements of beams 454 of the truss or beam system 452 to facilitate fusion of the implant with surrounding bone. The truss or beam system 452 can allow for larger volumes of bone graft material to be packed into the implant 450 while maintaining the biomechanical strength of the implant in comparison to implants without a truss or beam system 452.

As shown in FIGS. 23A and 23B, in some embodiments, the implant 450 can include an open bore extending from the proximal end to the distal end, for example, in the form of the channel 404. Embodiments having an open bore extending from the proximal to distal end can be configured to receive a guidewire or allow fusion to take place through the middle of the implant 450 and into the facet joint through the distal end of the implant 450. In other embodiments, the truss or beam system may extend within at least a portion of or an entirety of the inner volume of the implant. The truss or beam system can be in a planar or non-planar design depending on the desired strength needed.

Figure 14A:
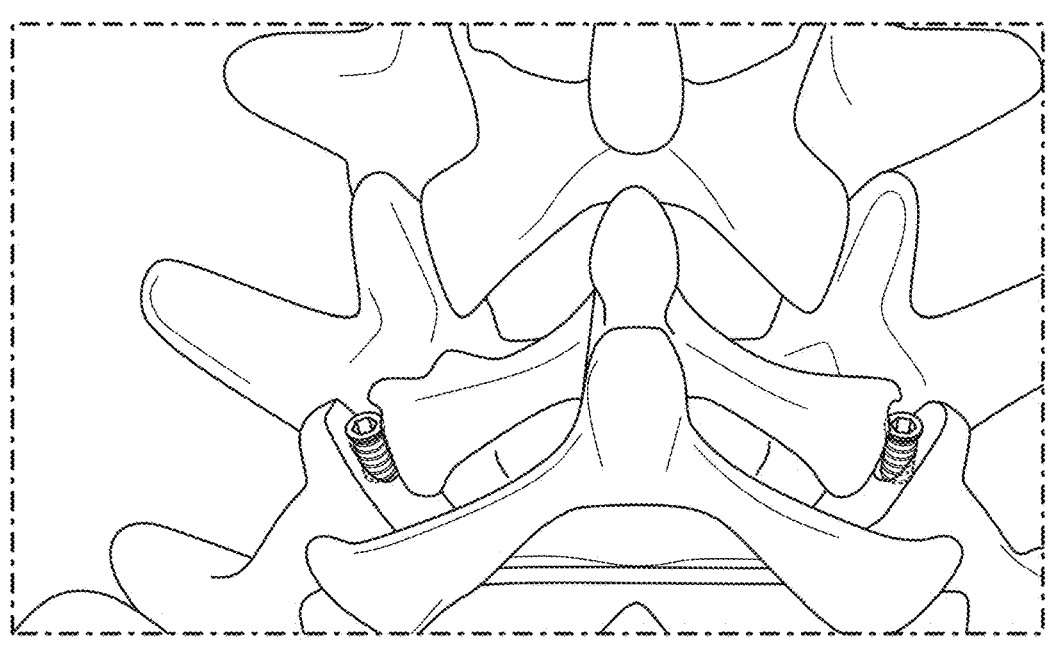
FIG. 14A illustrates a perspective view showing implants positioned within facet joints.

FIG. 14A illustrates another example of a pair of implants 400a positioned within the facet joints of a vertebral body. As shown in FIG. 14A, the implant 400a can be flush with or countersunk within the facet joint.

Figure 14B:
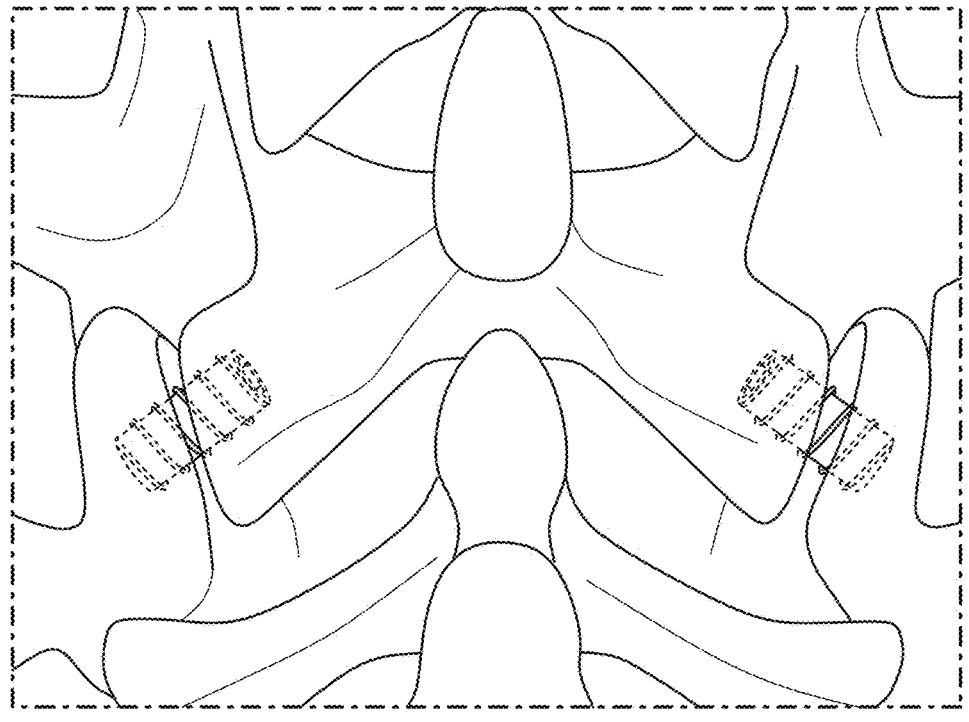
FIG. 14B illustrates a perspective view showing implants positioned within facet joints.

In alternative embodiments, the implants described herein can be implanted using a traditional facet screw approach. The implants can be placed across the facet joint in a trans approach. An example of an implant 400a extending across the facet joint in a trans approach is shown in FIG. 14B. In some embodiments, the implants used in a trans approach may be headless. In other words, in some embodiments, the implants do not include a separate head having a different diameter than the shank. Instead, a proximal end of an implant used in a trans approach has the same diameter, a similar diameter, or a smaller diameter than the shank of the implant to facilitate countersinking of the implant. In contrast an implant having a profile which extends higher than their insertion point into bone may cause irritation and require removal. Further, a countersunk implant may allow for bone growth over the implant which can prevent migration or backout of the implant. In some embodiments, the implants can be provided in a variety of lengths and diameters. In some embodiments, an implant may be inserted in a laminar approach or sub laminar approach. In some embodiments, the implant can be inserted across the facet joint and anchored into the pedicle. In some embodiments, the implant can be inserted across the facet joint and anchored into the articular process. In some embodiments, the implant can have a length sufficiently short to avoid perforation of the neuroforamen, which can cause nerve injury.

Figure 15B:
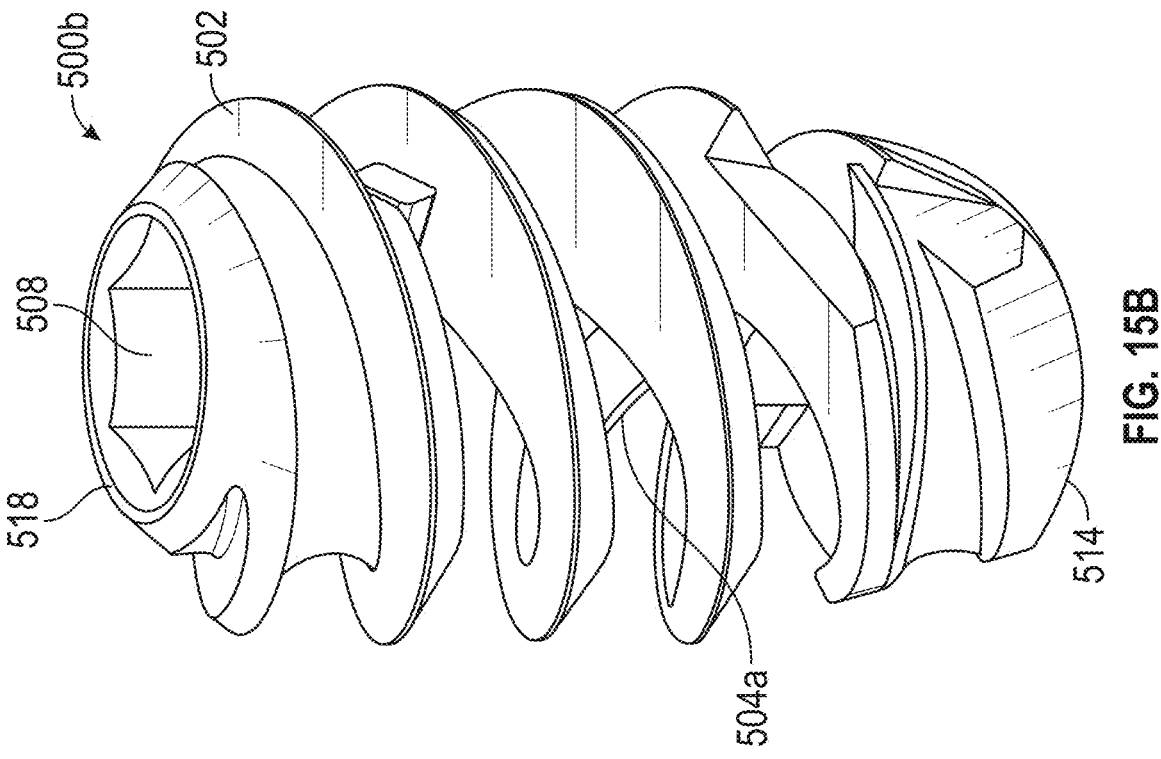
FIG. 15B illustrates a perspective view of an embodiment of an implant.
Figure 15A:
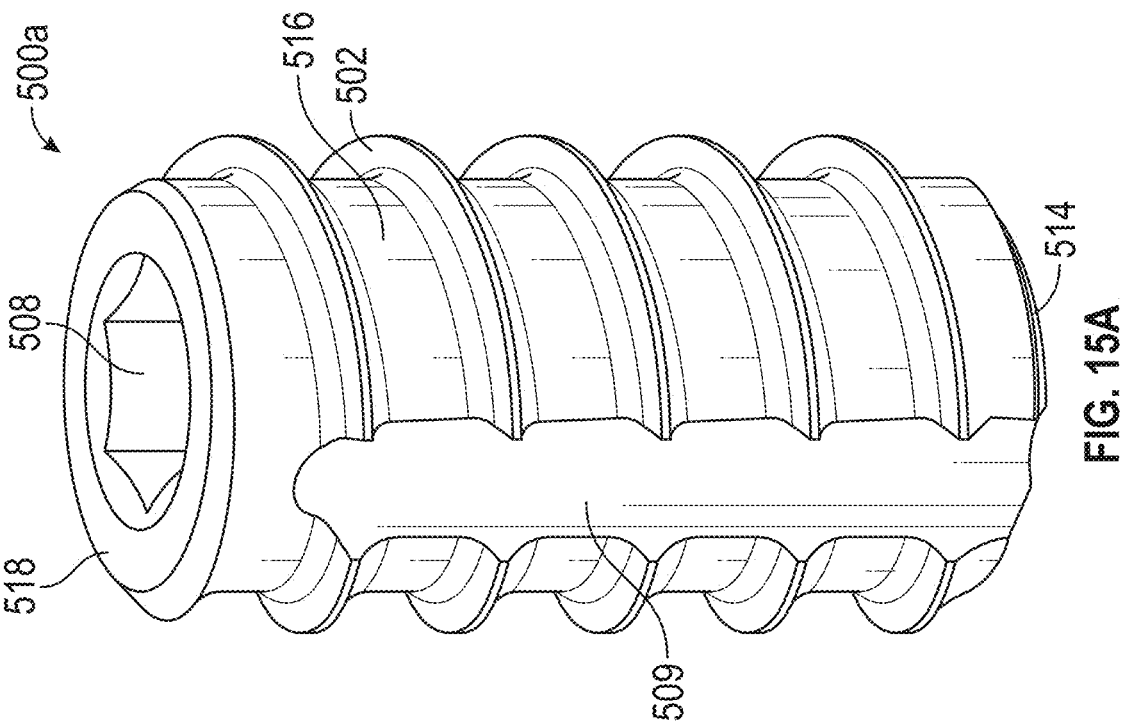
FIG. 15A illustrates a perspective view of an embodiment of an implant.

FIG. 15A illustrates an embodiment of an implant 500a. The implant 500a can include generally include any of the same or similar functions and features as the implants 400a, 400b, and 400c. The implant 500a can be an intrafacet implant, such as an intrafacet screw. The implant 500a includes engagement features 502. The engagement features 502 can be in the form of threads extending between a proximal end 518 and a distal end 514 of the implant 500a. The implant 500a can be implanted within a facet joint. The engagement features 502 can be configured to engage a portion of a superior articular process and an inferior articular process to secure the facet joint with the implant 500a.

In some embodiments, the engagement features 502 can be in the form of helical threads. In some embodiments, the helical threads can provide joint compression and prevent implant migration and back out.

In some embodiments, the implant 500a may not be canulated. In other embodiments, the implant 500a can be cannulated along an entire length of the implant or a partial length of the implant between the proximal end 518 and the distal end 514.

In some embodiments, the implant 500a can be loaded with demineralized bone matrix (DBM), cortical fibers, synthetic bone matrix, BMP2 or BMP7, peptide graft, autograft or any combination thereof.

In some embodiments, the implant 500a can include one or more elongated notches 509. The elongated notches 509 can extend proximally from the distal end 514 of the implant. As shown in FIG. 15A, the notches 509 can extend through at least some of the engagement features 502. In certain embodiments the elongated notches 509 can extend over at least 10%, at least 25%, at least 50%, at least 60%, at least 70%, at least 80%, or at least 90% of a length of the implant 500a between the proximal end 518 and distal end 514. In certain embodiments, the elongated notches 509 can extend over between 0% and 25%, between 25% and 50%, between 50% and 75%, between 50% and 100%, between 65% and 95% of the length of the implant 500a between the proximal end 518 and the distal end 514. The notches 509 can allow for bone growth therein so as to prevent or reduce migration or back out of. In certain embodiments, a plurality of notches 509 can be offset relative to one another such that at least some of the notches 509 will align with the bone of the superior and/or inferior vertebral bodies to facilitate bone growth within the notches 509 regardless of the orientation of the implant 500a when full seated within the facet joint.

In certain embodiments, the implant 500a can be configured to be inserted with a driver, such as a hex driver, a star driver, a square driver, a torx driver, or any other suitable driver for driving the implant 500a into bone. The proximal end 518 of the implant 500a can include an engagement feature 508 for coupling with an inserter as described herein. The engagement feature 508 can be shaped to couple with a hex driver, a star driver, a square driver, a torx driver, or any other suitable driver for driving the implant 500a into bone.

In some embodiments, a tip 510 of the implant can be flat. In some embodiments, the implant 500a or a shank 516 of the implant can be untapered throughout the entire length of the implant or a portion of the length. For example, the shank can have a uniform cross-section or a generally uniform cross-section (for example, other than the one or more notches 509). In some embodiments, the engagement features 502 (e.g., threads) can extend a uniform distance or generally uniform distance from the shank 516 throughout the length of the implant. Such untapered embodiments may further prevent or reduce migration or back out of the implant 500a from a surgical location in comparison to tapered implants. In some embodiments, the implant 500a can be self tapping or self drilling.

In some embodiments, the implant 500a can be textured by bead blasting, chemical etching, acid etching, 3D printing, coating such as HA or TCP, or any other suitable mechanism. Texturing of the implant 500a can help with fusion and bony integration.

In some embodiments, the implant 500a may be headless. In other words, in some embodiments, the implant 500a does not include a separate head having a different diameter than the shank 516. Instead, a proximal end 518 of the implant can have the same diameter, a similar diameter, or a smaller diameter than the shank 516 of the implant to facilitate countersinking of the implant 500a.

The implant 500a can be formed of titanium, stainless steel, or metal/alloy metal, biocompatible resorbable material, or other any other suitable synthetic implant material.

FIG. 15B illustrates an embodiment of an implant 500b. The implant 500b generally include any of the same or similar functions and features as the implant 500a. In contrast to the implant 500a, the implant 500b has a spiral or corkscrew design with engagement features 502 in the form of helical threads extending around an open core 504a between the proximal end 518 and the distal end 514. The implant 500b can include a closed tip 510 at the distal end 514. The corkscrew design has additional space between the threads for bone growth in comparison to, for example, the implant 500a. The engagement features 502 can include sharp cutting flutes for biting bone and gaining bone purchase.

The space between the engagement features 502 can allow bone graft to flow through the implant 500b and contact bone for fusion. The implant 500b can be loaded with demineralized bone matrix (DBM), cortical fibers, synthetic bone matrix, BMP2 or BMP7, peptide graft, autograft or any combination thereof.

Figure 15D:
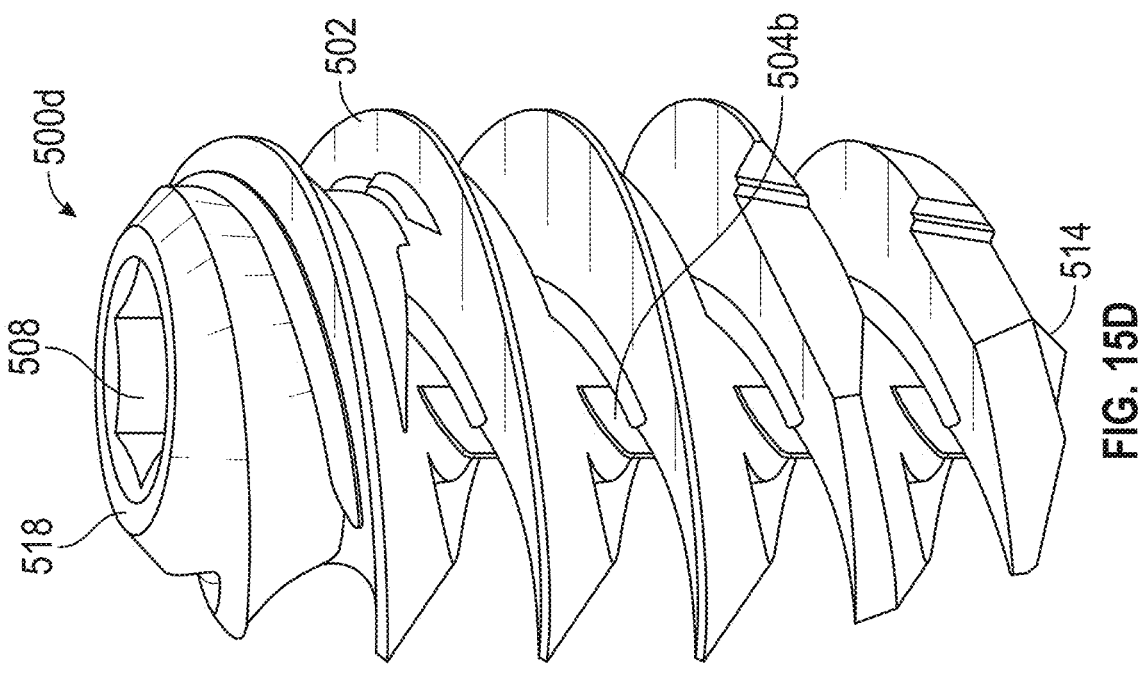
FIG. 15D illustrates a perspective view of an embodiment of an implant.
Figure 15C:
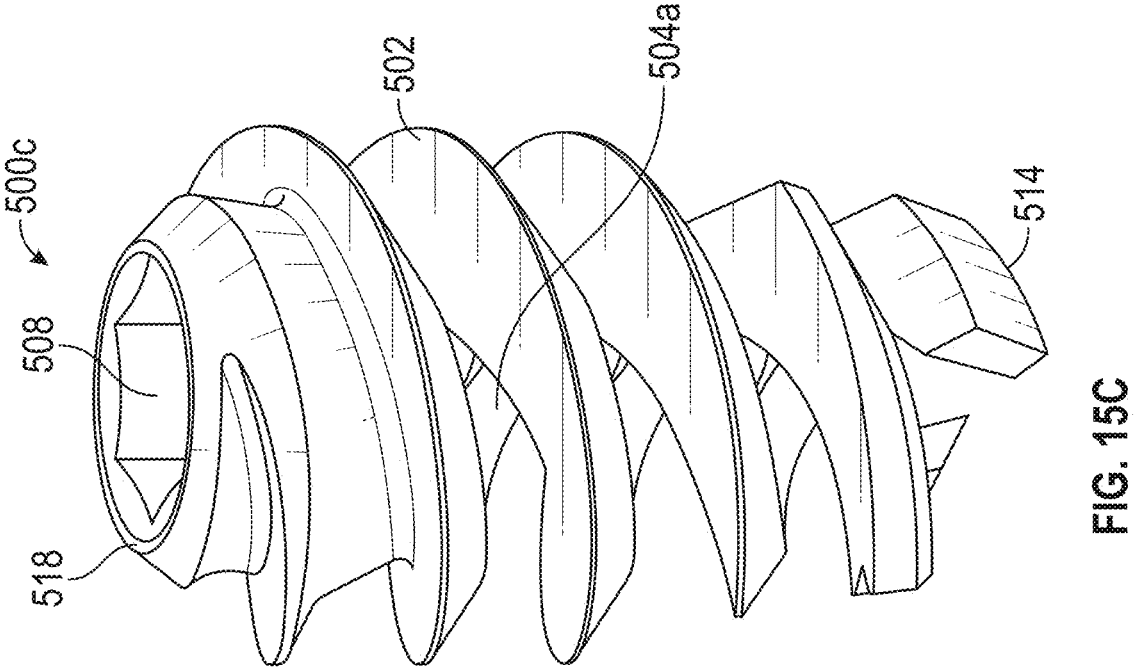
FIG. 15C illustrates a perspective view of an embodiment of an implant.

FIG. 15C illustrates an embodiment of an implant 500c. The implant 500c can generally include any of the same or similar functions and features as the implant 500b. In contrast to the implant 500b, the implant 500c includes an open distal end 514.

FIG. 15D illustrates an embodiment of an implant 500d. The implant 500d can generally include any of the same or similar functions and features as the implant 500b. In contrast to the implant 500b, the implant 500d includes a solid core 504b in addition to a closed distal end 514.

Figures 15E, 15F:
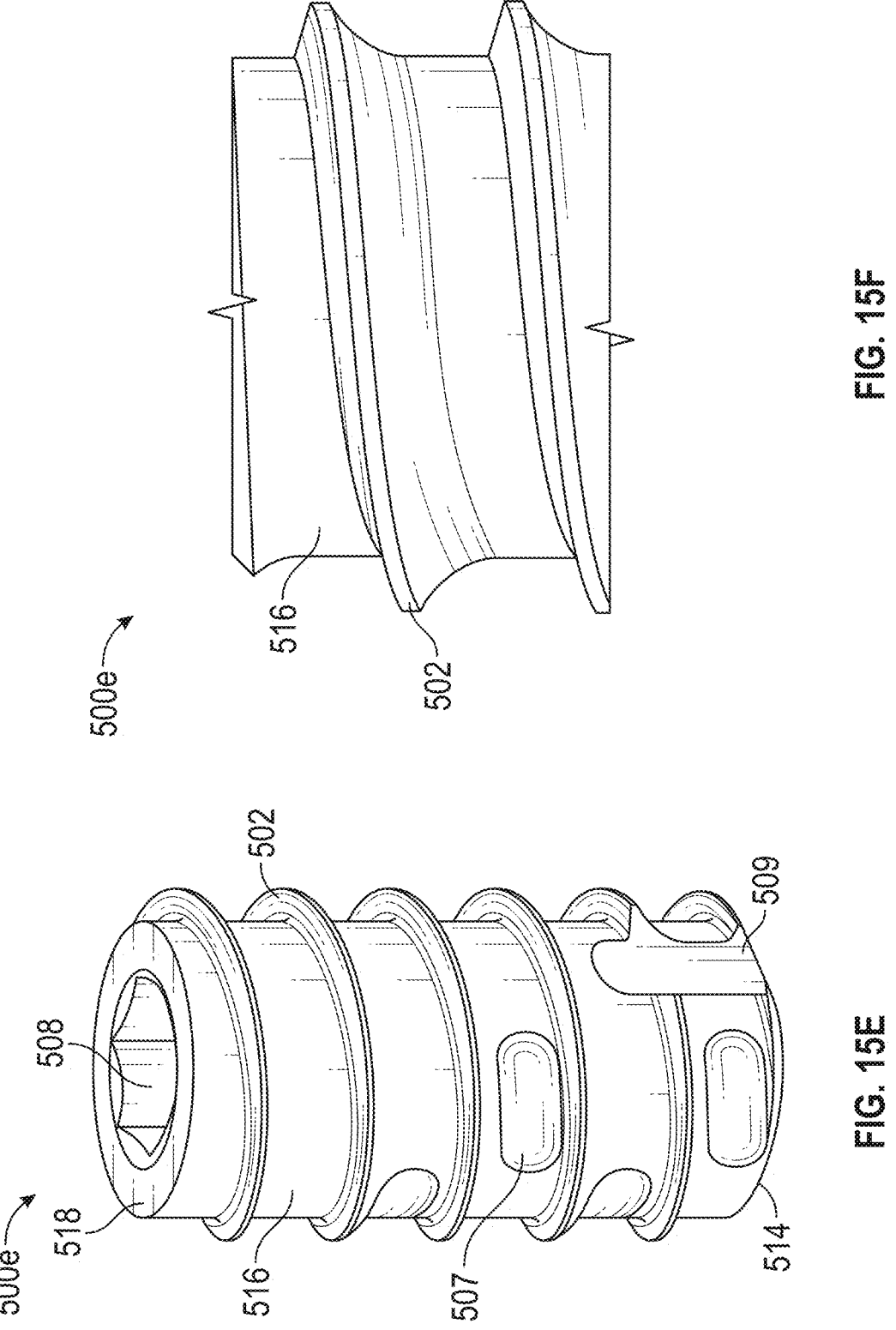
FIG. 15E illustrates a perspective view of an embodiment of an implant.
FIG. 15F illustrates an enlarged front view of a portion of the implant of FIG. 15E.

In some embodiments, the implant 500a may have higher biomechanical strength than implants having a corkscrew design, such as the implants 500b-d. In some embodiment, the implant 500d may have a higher biomechanical strength than implants having an open core and/or an open distal end, such as implants 500b-c. In some embodiments, the implant 500b can have a higher biomechanical strength than implants having an open core and an open distal end, such as implant 500c. [0055] FIGS. 15E and 15F illustrate an embodiment of an implant 500e. The implant 500d can generally include any of the same or similar functions and features as the implant 500a. In certain embodiments, the implant 500e is solid (e.g., not cannulated). The implant 500e may be desirable for use in the cervical spine. An implant, such as implant 500e, used in the cervical spine can have a diameter between 3 mm and 6 mm. In some embodiments, open areas, such as a channel extending through the implant, may lead to wakening and biomechanical failure in the implant wall of an implant having a diameter between 3 mm and 6 mm.

As shown in FIG. 15E, the implant 500e includes one or more elongated notches 509 extending proximally from the distal end. The elongate notch 509 shown in FIG. 15E is shorter than the elongated notch 509 shown in FIG. 15A. The implant 500e also includes one or more notches 507. The notches 507 can come in a variety of shapes, sizes, and amounts. The notches 507 can include one or more circular notches, square notches, oblong notches and/or notches of any other suitable shape which can be positioned in strategic locations to assist with fusion. In some embodiments, there may be only a single notch. The one or more notches 507 can be strategically placed between/around/through the engagement features of the implant 500e. The notches 507 can allow for bone growth therein so as to prevent or reduce migration or back out of the implant 500e. In some embodiments, the notches 507 and/or notches 509 can be offset relative to one another such that at least some of the notches 507 and/or 509 will align with the bone of the superior and inferior vertebral bodies to facilitate bone growth within the notches 507 regardless of the orientation of the implant 500e when fully seated within the facet joint. In some embodiments, the implant 500e can be self-tapping, for example, a self-tapping screw.

FIG. 15G illustrates an embodiment of an implant 500g. The implant 500g can include any of the same or similar features and functions as the implants 400a-c or 500a-500g. As shown in FIG. 15G, the implant 500g can include a plurality of surface indentations or pores 512. The pores 512 can be disposed about an entirety of the implant 500g. In some embodiments, the pores 512 can be disposed about more than 25%, more than 50%, more than 60%, more than 70%, more than 80%, or more than 90% of the external surface of the implant 500g.

The pores 512 can provide a greater total surface area in comparison to an implant without surface indentations to provide a larger surface for bone growth and fusion. By providing a larger surface for bone growth and fusion, an implant 500g having pores 512 may resist migration to a greater extent than an implant without pores 512. The pores 512 may be formed via 3D printing, chemical etching, acid etching, and/or bead blasting. The pores 512 can contain macroporosity and/or microporosity similar to bone, which can enhance bony ingrowth. These pores can range in size from 200 microns to 2000 microns. The porosity can resemble that of cancellous bone which contains these ranges of pores optimal for bony ingrowth. 3D printing may be less expensive than other methods as additional steps to create or enhance the pores or coat the implant may not be required after printing. The implant 500g may have threads, ridges, bumps, or any other suitable engagement features 502. In some embodiments, the implant 500g may be symmetrical. When the pores 512 are in tight contact with the surfaces of the surrounding facet joints, the ingrowth of bone can provide stability and prevent backout.

In some embodiments, any of the implants described herein, including implant 400a, implant 400b, implant 400c, implant 500a, implant 500b, implant 500d, implant 500e, and implant 500G may be shaped, dimensioned, or otherwise configured for implantation into a joint, such as the facet joint. In certain embodiments, any of the implants described herein may include a body or shank that is untapered throughout a length of the implant or a portion of the length. For example, the shank can have a uniform cross-section or a generally uniform cross-section (for example, other than the notches described herein). In certain embodiments, the threads of any of the implants described herein can extend a uniform distance or generally uniform distance from the shank throughout the length of the implant. Such untapered embodiments may further prevent or reduce migration or back out of the implant from a surgical location in comparison to tapered implants. In certain embodiments, a body or shank of any of the implants described herein can have a uniform external diameter and/or a uniform internal diameter (e.g., of a channel within the implant) between a proximal end a distal end). In certain embodiments, the body or shank of any of the implants described herein can have a uniform internal diameter from a distal end of an engagement feature (e.g., engagement feature 408 or 508) and a distal end of the implant. In certain embodiments, any of the implants described herein may have a pointed or tapered tip for insertion. A pointed or tapered tip can allow the implant to self-center in a pilot hole and enhance the ability of the implant to gain purchase.

In certain embodiments, the diameter of any of the implants described herein can vary depending on the anatomy at the location in which the implant is to be implanted. In certain embodiments, the diameter can be between 3 mm and 7.5 mm. In certain embodiments, implants having a diameter smaller than 3 mm don't provide sufficient biomechanical strength or purchase. In certain embodiments, implants having a diameter greater than 7.5 mm can be too wide for use in the facet joints and may perforate the foramen and cause nerve damage. Implants of varying sizes may accommodate different regions of the spine, e.g., from cervical to lumbar, and patients of different sizes. In some instances, facet joints may become more relaxed when there is instability, which may require an implant having a larger diameter for stabilization of the joint. The cervical spine facet joints are typically much smaller than the lumbar facet joints, and require an implant having a smaller diameter for safe implantation.

In certain embodiments as described herein, a drill is used to create a pilot hole. In certain embodiments, the drill bit has a diameter less than the diameter of the implant. In certain embodiments, the drill bit has the same or a similar diameter to a minor diameter of the implant. Having a drill bit with the same or a similar size may provide for appropriate bone purchase of threads of the implant. A drill bit that is too large may not provide adequate bone purchase.

In certain embodiments, any one of the implants described herein may be part of a set containing numerous implant sizes and drill bits corresponding to the numerous implant sizes. The implants may come in a sterile kit alone or with disposable instruments. The sterile kit may be sterilized by E-beam, gamma, EO, or other means of terminal sterilization. The implants and instruments can also or alternatively be autoclaved in a standard tray prior to surgery.

In certain embodiments, any of the implants described herein can be textured by bead blasting, chemical etching, acid etching, 3D printing, coating such as HA or TCP, or any other suitable mechanism. Texturing of the implant can help with fusion and bony integration.

In certain embodiments, any of the implants described herein may be headless. In other words, in some embodiments, the implants described herein do not include a separate head having a different diameter than the shank. Instead, a proximal end of the implant has the same diameter, a similar diameter, or a smaller diameter than the shank of the implant to facilitate countersinking of the implant. In certain embodiments, the proximal end may facilitate positioning of the implant flush with the facet joint and allow bone graft to be packed over the implant. In certain embodiments, any of the implants described herein may prevent compression of the facet joint when implanted therein. In certain embodiments, any of the implants described herein may have the same or similar biomechanical strength as traditional facet implants, but may allow for placement of the implant along a variety of different trajectories. In some embodiments, the implants described herein may be used with a sublaminar, laminar, or posterior approach in which the implant crosses both articular processes.

In certain embodiments, the tips of any of the implants described herein may be flat, conical, tapered, pointed, symmetrical with the shank, or any other suitable shape. In certain embodiments, the tips of any of the implants described herein may include one or more cutting flutes. Alternatively, the tips may not include any cutting flutes.

FIG. 16A illustrates an embodiment of a drill bit 600a which may be used to drill a pilot hole as described herein. The drill bit 600a includes a distal section 602, which may be in the form of a flute drill bit or a twist drill bit, for formation of the distal end of the pilot hole. The drill bit 600a can also include a proximal section 604a having a crown shape with saw teeth 606 extending distally and disposed radially beyond the circumference of the distal section 602. The proximal section 604a can be positioned proximally to the distal section 602. The proximal section 604a can create an area at a proximal end of the pilot hole having a larger cross-sectional area than at the bottom end of the pilot hole, which can provide a greater area for packing bone graft after an implant is positioned in the pilot hole. The proximal section 604a may form an area for encapsulating the implant. The proximal section 604a may debride and decorticate over an external portion of the facet joint to provide additional surface area for bone fusion.

FIG. 16B illustrates an embodiment of a drill bit 600b which may be used to drill a pilot hole as described herein. The drill bit 600b can generally include any of the same or similar functions and features as the drill bit 600a. The drill bit 600b includes a proximal section 604b that differs from the proximal section 604. The proximal section 604b includes a tapered blade 608 extending radially beyond the circumference of the distal section 602. The tapered blade 608 is configured to ream the bone at the facet joint to form a funnel shaped opening at a proximal end of the pilot hole to allow for the packing of bone graft over the implant when the implant is positioned within the pilot hole. The proximal section 604b may form an area for encapsulating the implant.

Figure 16C:
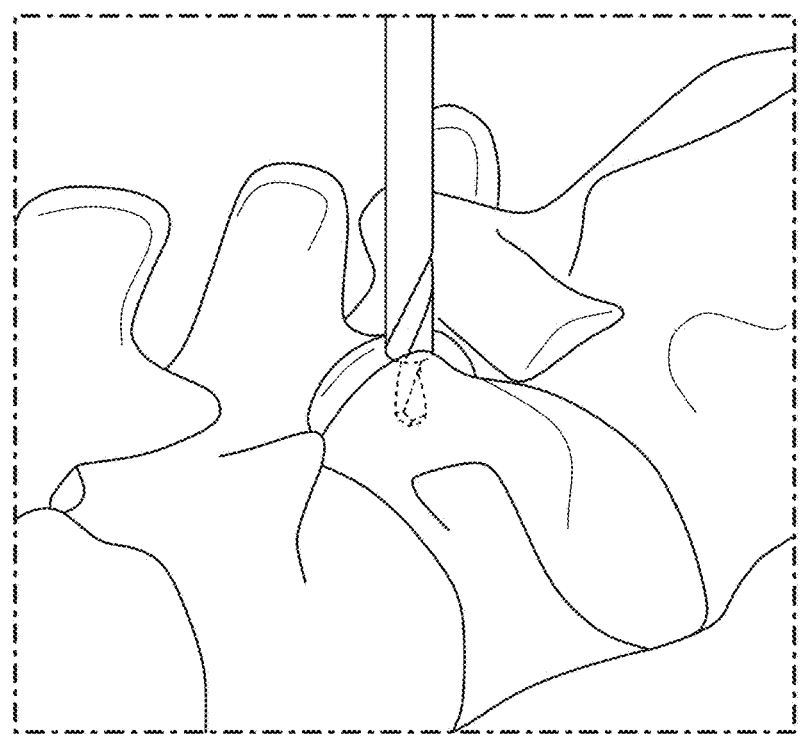
FIG. 16C illustrates a perspective view of the drill bit of FIG. 16B positioned within a facet joint.

FIG. 16C depicts an example of the drill bit 600b positioned within the facet joint.

Figure 16D:
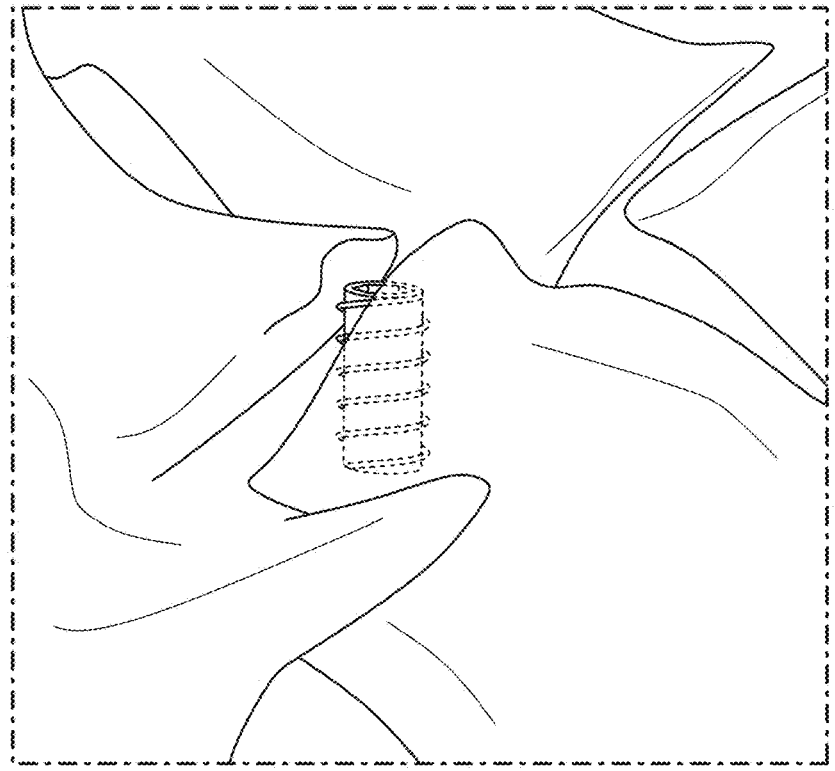
FIG. 16D illustrates a perspective view of an implant positioned within a facet joint.

FIG. 16D depicts an example of the implant 500e positioned within the facet joint. As shown in FIG. 16D, a top portion of the facet joint has been debrided and decorticated by the drill bit 600b, forming an opening for packing bone graft material over the implant 500e.

Figures 17A, 17B:
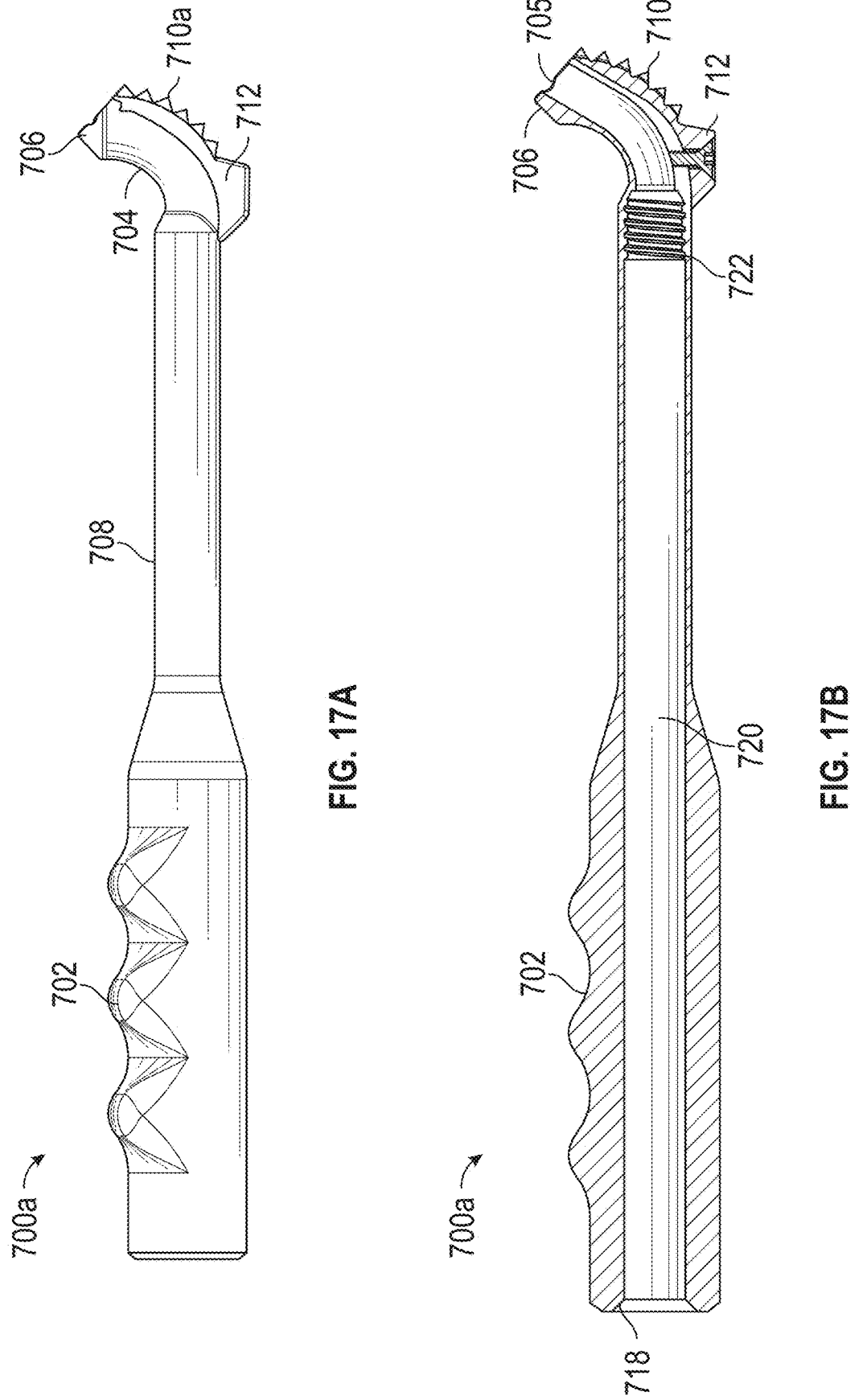
FIG. 17A illustrates a side view of an embodiment of a rasp.
FIG. 17B illustrates a cross-sectional view of the rasp of FIG. 17A.
Figure 17C:
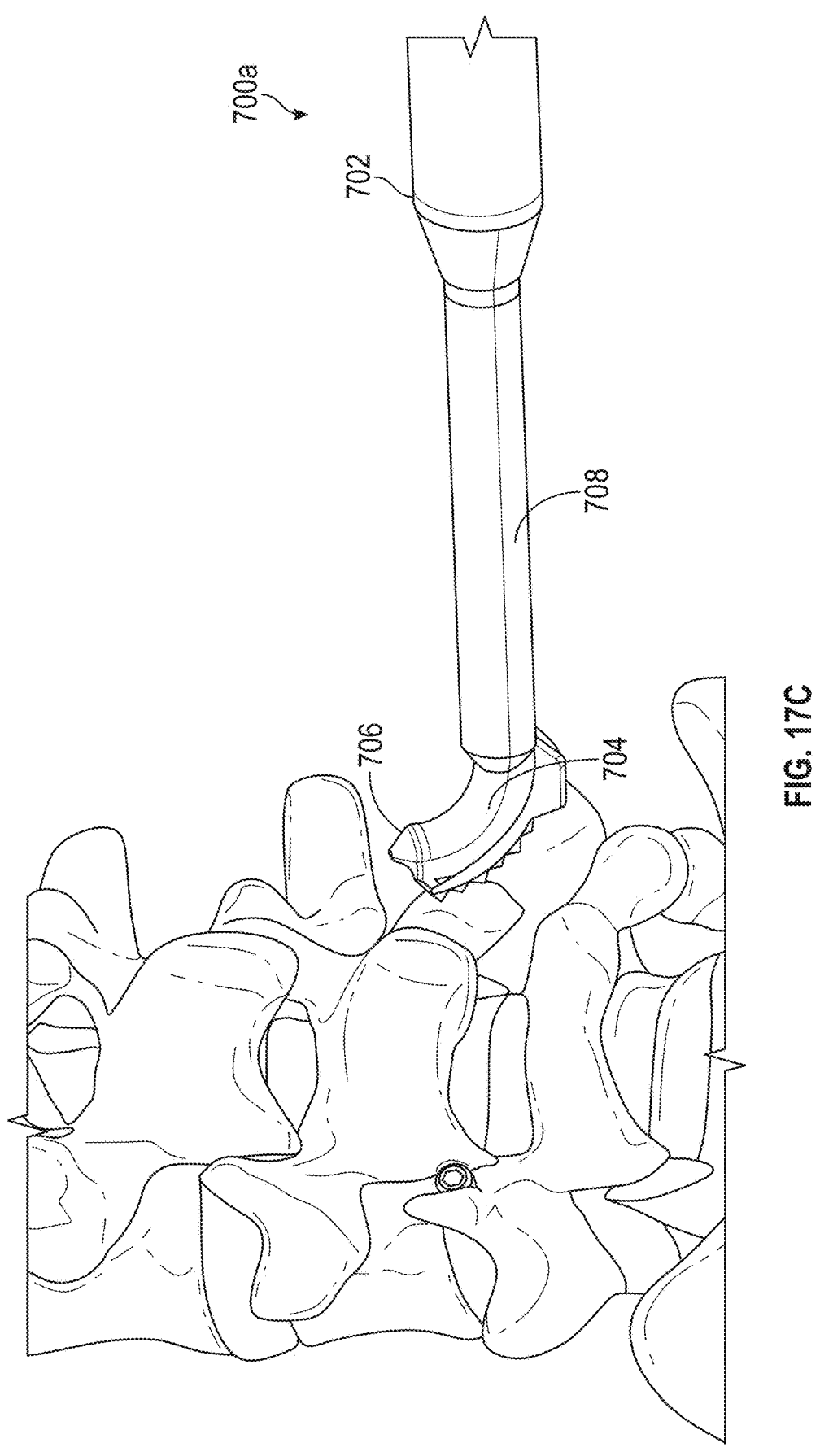
FIG. 17C illustrates a perspective view of an embodiment of a rasp positioned at a facet joint.
Figure 17D:
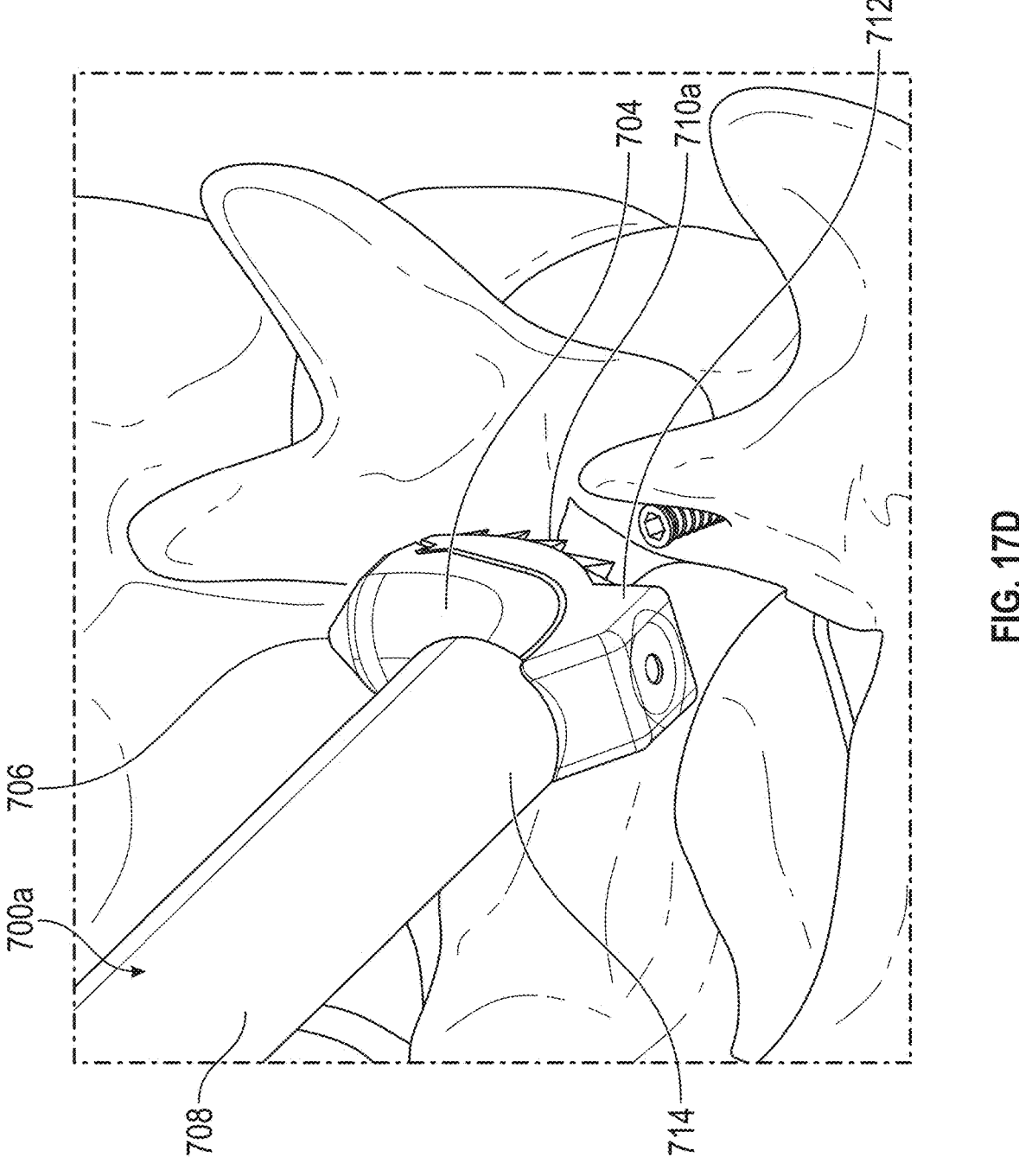
FIG. 17D illustrates a perspective view of an embodiment of a rasp positioned at a facet joint.

FIGS. 17A and 17B depict a side view and a cross-sectional view, respectively, of a rasp 700a. FIGS. 17C and 17D depict examples of the rasp 700a rasping a facet joint after an implant has been positioned therein using the devices and methods described herein. As described above, the implant may be positioned to be flush with or counter-sunk within the facet joint. With an implant that is flush with or countersunk within the facet joint, the rasp 700a can be used to rasp the entirety of the joint line of the facet joint without catching on the implant to promote fusion. In some embodiments, bone graft can be distributed over the joint and implant, for example, after rasping the joint line. In certain embodiments, the rasp 700a can be inserted into the same incision as used for implantation of an implant, such as an intrafacet implant. The rasp 700a can be inserted into the same incision as used by any of or all of the instruments used to implant the implant (e.g., a needle assembly, a drill bit, an inserter, etc.). In certain embodiments, an implanting procedure and a rasping procedure can be performed using a single implant.

The rasp 700a can includes a handle or grip section 702, a curved or angled section 704, and a distal section 706. In certain embodiments, rasp 700a can included a connection section 708 extending between the handle section 702 and the curved section 704.

In certain embodiments, one or more of the handle section 702, connection section 708, curved section 704, and distal section 706 can be integrally formed with one another. In other embodiments, one or more of the handle section 702, connection section 708, curved section 704, and distal section 706 can be separate components that may be coupled, removably or permanently, to form the rasp 700a.

In some embodiments, the distal section 706 is conical or generally conical. This shape can be beneficial for delivering bone graft material to, for example, a facet joint. In some embodiments, the distal section 706 is pointed, bulleted, and/or sharp to dissect or split muscle and tissue as it is advanced to the surgical location. Alternatively, the distal section 706 can be blunt to allow for displacement of muscle without risk of cutting of nerves or other tissue.

The rasp 700a may have a single or multiple openings 705 configured to deliver bone graft material to a desired location. In some embodiments, the one or more openings 705 are positioned within the distal section 706. The one or more openings may be in fluid communication with a bone graft delivery device when the rasp 700a is coupled thereto. In some embodiments, the one or more openings may be in fluid communication with an elongate tube of a bone graft delivery device. In some embodiments, the one or more openings may be offset from a central axis of the distal section 706. In some embodiments, a distal most point of the distal section 706 may extend beyond a distal edge of the one or more openings 705.

In some embodiments, the rasp 700a can include a lumen 720. The lumen 720 can be in fluid communication with the one or more openings 705 at the distal section 706 to allow delivery of bone graft therethrough. The lumen can extend between an opening 718 at a proximal end of the rasp and an opening in the distal section. In some embodiments, a pusher, plunger, or other means may be used to deliver graft through the lumen.

In certain embodiments, the lumen can be dimensioned, shaped, or otherwise configured to receive a tube, for example, a tube of a bone graft delivery device. In certain embodiments, the rasp 700a can include threads 722. The threads 722 can couple to complementary threads of a tube, for example, of a bone graft delivery device.

As shown in FIGS. 17A-D, at least one at least one side or area of the rasp 700a includes a rasping surface 710a configured to serve as a rasp for scraping bone. The rasping surface 710a can include a series of jagged edges or other suitable surface features. The rasping surface 710a can have a variety of teeth patterns, sizes, diameters, and/or lengths to allow for rasping of different orthopedic sites including, but not limited to, the transverse process of the spine, facets, SI joint, disc space, tibial plateau, hip and an array of other locations. In some embodiments, the surface features of the rasping surface 710a can be patterned (for example, staggered relative to one another), positioned, sized, shaped, and/or otherwise configured to facilitate rasping an entire surface of a bone. In some embodiments, the surface features of the rasping surface 710a can be patterned (for example, staggered relative to one another), positioned, sized, shaped, and/or otherwise configured to facilitate self-cleaning of the rasping tip. In some embodiments, the surface features of the rasping surface 710a can be patterned (for example, staggered relative to one another), positioned, sized, shaped, and/or otherwise configured to prevent or restrict tissue from binding to the surface features of the rasping surface 710a or other portions of the rasp 700. In some embodiments, the teeth are staggered when neighboring rows of teeth are offset from one another. Staggering of the teeth can allow the rasp 700 to contact all or substantially all of the surface of a bone during a rasping procedure.

In some embodiments, the edges of the surface features of the rasping surface 710a may be triangular in shape. In some embodiments, the edges may be flat. In some embodiments, the jagged edges may form a plurality of flat surfaces parallel with each other all within the same plane. In some embodiments, the rasping surface 710a can include a rough-ened surface extending around an outer surface of the tip. In some embodiments, the rasping surface 710a can include a surface texturing configured to act as an abrasive to roughen the bone during a rasping procedure. The surface texturing can be sprayed on, chemically etched, 3D printed, bead blasted or created using any other suitable texturing process. In some embodiments, the rasping surface 710a may be positioned on a portion of the curved section 704 and/or a portion of the distal section 706. In some embodiments, the rasping surface 710*a* can be a curved surface extending along a bottom portion of the rasp 700*a*. The curvature of the rasping surface 710*a* can prevent muscle or tissue from catching onto the rasp 700*a* when the rasp 700*a* passes through the tissue to reach a bone area. The rasp 700*a* can be used to decorticate bone in the spine or other regions where orthopedic fusion is needed. The curvature of the rasping surface 710*a* can also facilitate rasping of both a facet and transverse process simultaneously by facilitating contact of the rasping surface with both the facet and transverse process simultaneously. In some embodiments, the curvature of the rasping surface 710*a* can allow a user to move the rasping surface 710*a* from one anatomical area to another, for example from a facet to a transverse process or from a transverse process to a facet, without catching the rasping surface 710*a* on muscle or tissue.

In some embodiments, the rasping surface 710*a* can be removable. In some embodiments, the rasping surface 710*a* can be replaceable with another rasping surface 710*a* or with a rasping surface having an alternative design. In some embodiments, the rasping surface 710*a* can be disposable. In some embodiments, the rasping surface 710*a* can part of a removable rasping cover or piece 712. A rasping surface can become dull over time or may become contaminated. Replacement of a rasping surface, such as rasping surface 710*a* allows for a sharp and clean surface 710*a* to be used for each patient with the same rasp 700*a*. In some embodiments, a rasping surface 710*a* can be replaced with a rasping surface 710*a* having teeth with different lengths and/or geometries to rasp different bone anatomies.

In some embodiments, the rasp 700*a* can include a main body 714 and the rasping cover 712. In some embodiments, the main body 714 can include the handle section 702, the connection section 708, the curved section 704, and distal section 706.

In certain embodiments, the rasping cover 712 can be coupled to the main body 714. In some embodiments, the rasping cover 712 can be configured to couple to the main body 714 so as to be positioned against or cover an exterior surface of the rasp 700*a*. In some embodiments, the surface is at least partially formed by an exterior surface of the curved section 704. In other embodiments, the surface is at least partially formed by an exterior surface of the connection section 708.

In some embodiments, the distal section 706 is pointed, bulleted, and/or sharp to dissect or split muscle and tissue as it is advanced to the surgical location. The overall shape of the rasp 700*a*, which includes an elongated straight portion defined by the handle section 702 and the connection section 708, with the smaller angled section and distal section 706 can facilitate dissection or splitting of muscle and tissue by providing additional leverage for a user to exert force on the muscle and tissue. Alternatively, the distal section 706 can be blunt to allow for displacement of muscle without risk of cutting of nerves or other tissue.

In some embodiments, the curved section 704 can be configured to facilitate a projection of graft and access to an opposite transverse process from a first transverse process (for example, adjacent transverse processes of adjacent superior and inferior vertebral bodies) without requiring an additional incision. In some embodiments, a radius of curvature of the curved section 704 can facilitate the flow of graft through the rasp 700*a*. Without an appropriate radius of curvature graft may bind in the transition between the straight section of the lumen proximal to the curved section

704 and the curved section 704. The binding of the graft may prevent or restrict the flow of the bound graft out of the rasp 700*a*. In some embodiments, the radius of curvature can facilitate dissection of adjacent transverse processes with minimal repositioning of the rasp 700*a* and/or within the same incision. For example, a surgeon can use the distal section 706 to rasp a first transverse process and rotate or move the distal section 706 while the distal section 706 is positioned within the body to rasp a second transverse process.

In some embodiments, one or more of the internal diameter of the curved section 704, the radius of curvature of the curved section 704, and a curve angle of the curved section 704 can be dimensioned to facilitate the advancement of the bone graft through the curved section 704. In some embodiments, the internal diameter of the curved section 704 can be between 2.5 mm to 12 mm. In some embodiments, the radius of curvature of the curved section 704 can be between 5 mm to 24 mm. In some embodiments, the curve angle of the curved section 704 can be between 0° and 90°. In some embodiments, the curve angle is preferably between 45° and 70°.

In some embodiments, the curvature of the curved section 704 and/or the rasping surface 710*a* can facilitate rasping of both a facet and transverse process simultaneously by facilitating contact of the rasping surface with both the facet and transverse process simultaneously. In some embodiments, the curvature of the curved section 704 and/or the rasping surface 710*a* can allow a user to move the rasping surface 710*a* from one anatomical area to another, for example from a facet to a transverse process or from a transverse process to a facet, without catching the rasping surface on muscle or tissue.

Figure 18A:
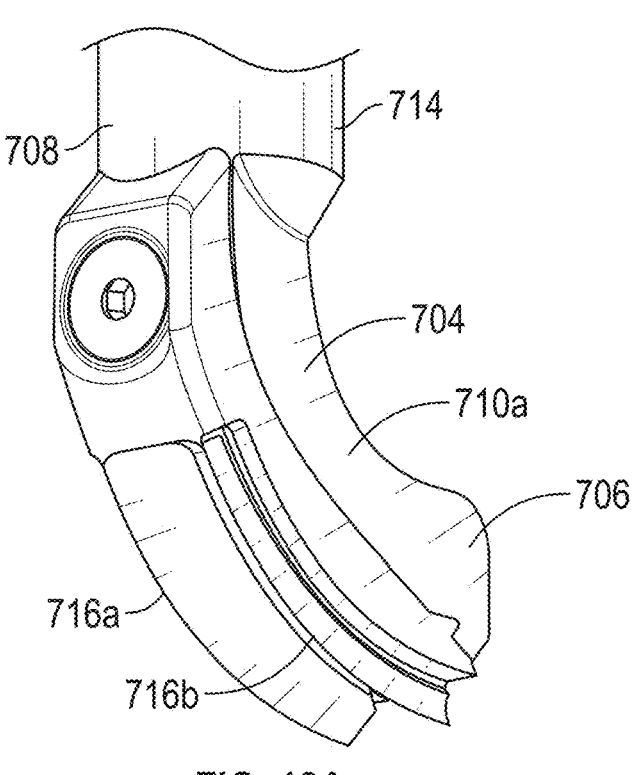
FIG. 18A illustrates an enlarged perspective view of a distal end of an embodiment of a rasp.
Figure 18B:
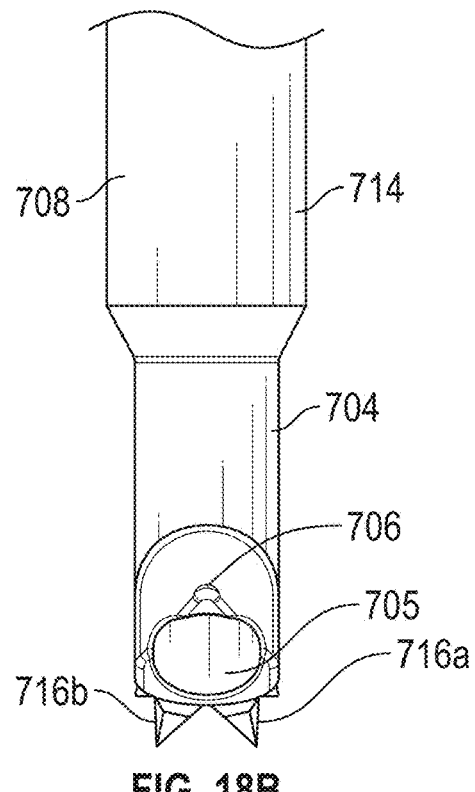
FIG. 18B illustrates an enlarged front view of the distal end the rasp of FIG. 18A.
Figure 18C:
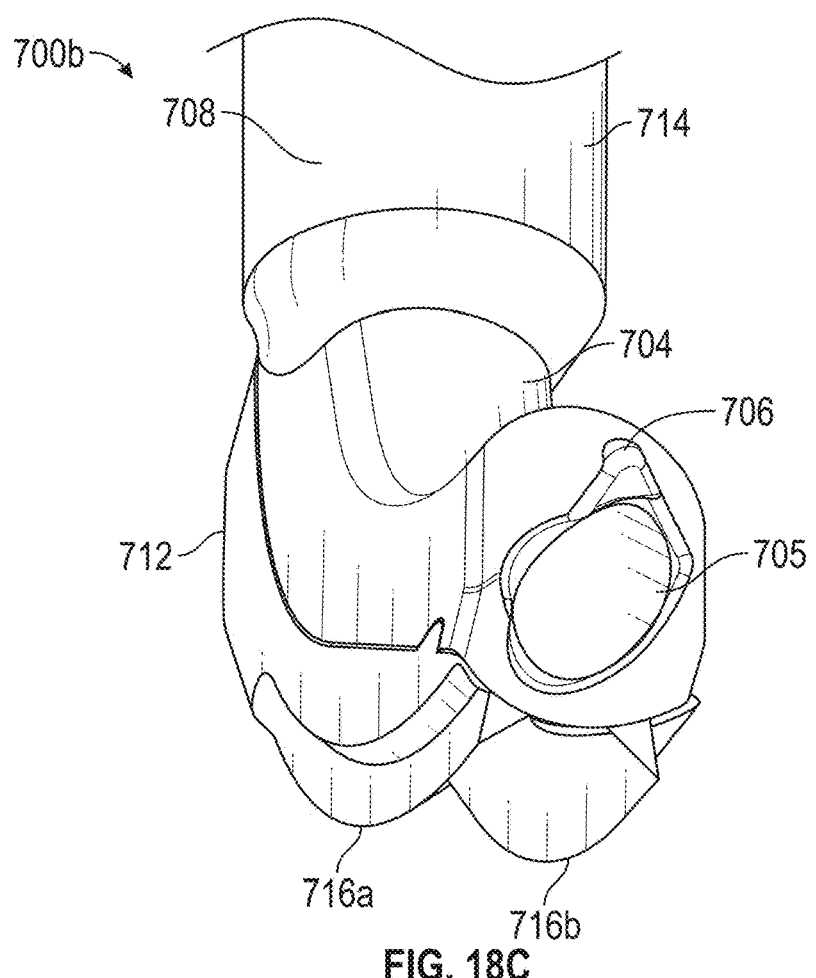
FIG. 18C illustrates an enlarged perspective view of the distal end the rasp of FIG. 18A.

FIGS. 18A-C illustrate a distal region of a rasp 700*b*. In certain embodiments, the rasp 700*b* can include any of the same or similar functions and features as the rasp 700*a*. In the illustrated embodiment, the rasp 700*b* has a rasping surface 710*b* that differs from the rasping surface 710*a* shown in the FIGS. 17A-D. The rasping surface 710*b* can include blades 716*a* and 716*b*. The blades 716*a*-*b* can be positioned on the cover 712. The blades 716*a*-*b* can extend along the curved section 704 towards the distal section 706. In some embodiments, each blade 716*a* can extend along a length of more than 30%, more than 40%, more than 50%, more than 60%, more than 70%, more than 80%, more than 90%, between 25% and 50%, between 50% and 75%, or between 75% and 100% of the length of the curved section 704.

The blades 716*a* and 716*b* can be laterally offset from a central axis of the curved section 704 on opposite sides of the central axis. Each blade 716*a* and 716*b* can include a slight curvature to facilitate enhanced removal of periosteum. Each blade 716*a* and 716*b* can be configured to remove the periosteum and soft tissue from bone to create bleeding bone optimal for fusion.

Figure 18D:
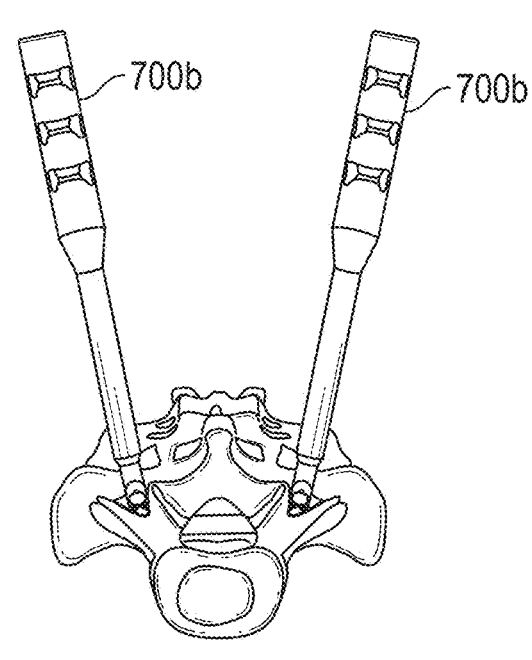
FIG. 18D illustrates two rasps of FIG. 18A positioned at surgical locations.

In certain embodiments, one of the blades 716*a* and 716*b* is used to scrape the periosteum and soft tissue by tilting or angling the rasp laterally, for example, as shown in FIG. 18D. It may be desirable to scrape the transverse process in a medial to lateral direction. Scraping in a lateral to medial direction may damage or fracture the transverse process. The placement of the blades 716*a* and 716*b* offset from the central axis of the curved section 704 can facilitate the positioning of the blades to scrape the transverse processes in the medial to lateral direction. In some embodiments, the blade 716*a* may be used to scrape a transverse process or facet joint on one side of a vertebral body (for example, the left side of the vertebral body) and the other blade 716*b* can be used to scrape the transverse process or facet joint on the other side of the vertebral body (for example, the right side of the vertebral body) as shown in FIG. 18D. FIGS. 18A-18C further show the distal opening 705 for delivering bone graft through the rasp 700*b*. In an alternative embodiment, a rasp may include only a single blade, such as one of blade 716*a* and 716*b*, for unilateral decortication or surgeon preference.

In some embodiments, after the one or more implants are placed, one or more of rasps, such as rasps 700*a* and 700*b* can be used to decorticate bone, such as for example, the facet joints and/or transverse processes. In some embodiments, the one or more rasps can be inserted through the same incision as the one or more implants. Inserting rasps through the same incision can prevent or reduce scarring, blood loss, and/or trauma to the patient. Inserting rasps through the same incision can also decrease time for the surgeon to perform a procedure. Inserting rasps through the same incision can also reduce the risk of infection that would be associated with having another incision. In some embodiments, the shape and the size of the rasp can be optimized for accessing the bony area through the same incision. In some embodiments, a surgeon can use one or more dilators, retractors, or other instruments to help mitigate tissue damage. In some embodiments, a retractor may have a light source or illuminator to aid in direct visualization.

In some embodiments, any of the rasps described herein can be used to obliterate a medial branch nerve of the patient. The medial branch nerve lies on the transverse processes and in the facet joint. The medial branch nerve innervates a facet joint and is responsible for the patient feeling pain in the facet joint. The medial branch nerve is positioned on the transverse process and vertebral body junction. In some embodiments, the physician can rasp the transverse process to mechanically obliterate the medial branch nerve to provide pain relief to the patient. In some embodiments, a medial branch block may be performed before rasping the medial branch nerve. In some embodiments, the medial branch nerve can be obliterated via the rasp after an implant is delivered to the facet joint. Bone graft may then be placed over the facet joint or transverse processes for fusion. This will also prevent the nerve from growing back and causing pain.

In some embodiments, the one or more rasps can be inserted through a second incision. For example, in some embodiments, it may be preferable to use an alternative incision to reach a target location if it is difficult or impossible to reach the target location through a first incision. In some embodiments, a surgeon may choose to create a larger incision for direct visualization of bony anatomy, for example, if minimally invasive surgery is not performed. In some embodiments, the second incision can be a Wiltse approach or larger incision. In some embodiments, a retractor may be used to assist with tissue retraction. The retractor may be monolithic or contain multiple pieces. In some embodiments, the retractor can be expandable.

In some embodiments, the rasps described herein, such as rasps 700*a-b*, can be used in an open or minimally invasive procedure. One or more rasps can be inserted into any incision suitable for reaching a desired surgical location, such as a facet joint, transverse process, disc space or sacroiliac joint, hip, ankle, tibia etc. In some embodiments, the rasp can include an indicator, such as a line or arrow, for example on the proximal end of the rasp, to indicate the orientation of the distal end of the rasp when the distal end of the rasp is positioned within the body. For example, in some embodiments, a proximal end of the rasp can include a line or arrow pointing in the direction of or otherwise indicating the orientation of the distal tip 706.

In some embodiments, bone graft is the placed in a rasp, such as rasps 700*a-b*, or in a graft tube into a lumen in the rasp to deliver graft in conjunction with implants. In some embodiments, decortication and bone graft delivery on the facets and transverse process provide ancillary fusion to the placed implants. In previous surgical techniques bone graft was only used on the transverse processes when open lumbar fusions were performed due to accessibility issues. A large midline incision was made and the tissue was dissected out to the transverse processes and facets. Using previous methods for minimally invasive lumbar fusions, there is no way to adequately decorticate and deliver bone graft for posterolateral fusions. Attempts with other devices have been made with little to no success. The embodiments of the described herein allow a user to decorticate bone and deliver bone graft simultaneously to a targeted site. Under previous methods, these steps are generally done with two separate instruments, for example, a rasp and a bone graft delivery instrument, which can make it difficult for the user to find the decorticated site once the rasp is removed from the incision and the bone graft delivery instrumented is inserted into the incision.

In some embodiments, a physician can dilate to the facet joint, for example using a dilator as described herein, and use any of the following instruments including but not limited to a facet locator, drill guide, broach, tap, drill bit, and/or inserter to implant a facet bone dowel or other intrafacet implant into the facet joint or across the facet joint. These instruments may be used in consecutive order or some of the instruments may be skipped depending on the surgeon's preference. In some embodiments, the surgeon may use all of these instruments or less than all of these instruments.

Once the implant is placed within the body, a rasp, such as rasps 700*a-b*, can be inserted into the same incision and to the facet joint. In some embodiments, a rasp, such as rasps 700*a-b*, can be used to rasp the facet joint and then can be maneuvered to rasp the transverse process using the same incision. Such a procedure can prevent scarring, blood loss, trauma and risk of infection. In some embodiments, after decorticating the transverse process, the rasp can be passed under the skin and through the muscle to an adjacent transverse process for decortication.

In some embodiments, the method can include delivering bone graft through the tip of the rasp using a bone graft delivery system, a bone graft delivery device, or a push rod. In some embodiments, before delivering bone graft, a cavity or pocket can be formed in muscle or tissue.

In some embodiments, bone graft compositions, either synthetic, allograft or allogenic, may be used for minimally invasive graft delivery procedures to visualize bone graft under the skin in situ. In some embodiments, bone graft compositions can be radiopaque. In some embodiments, the bone graft may be manufactured to be radiopaque. In some embodiments the graft may be radiopaque in nature, such as cortical bone or synthetic materials. Alternatively, bone graft can be enhanced with a contrast agent at the time of surgery. In some embodiments, cortical allograft fibers, DBM, or synthetic bone graft with wicking effect can provide improved results when adding a contrast agent at the time of surgery. In some embodiments, the contrast agent can include one or more of isovue, omnipaque, iodine, or any other suitable agent. In some embodiments, the contrast agent may be used in a 1:1, 1:2, 1:3 or 1:4 contrast agent to bone graft mixture. If a ratio greater than 1:1 is used, the bone graft may become over hydrated or have poor consistency. In some embodiments, ratios less than 1:1 may provide less visibility for imaging. In some embodiments, a carrier or binder material, such as collagen, bioresorbable polymers, or any other suitable carrier material, may provide radiopacity. In such embodiments, the carrier may be used to wick up iodine or other contrast agents and retain those agents until implanted and then resorbed. The radiopacity of the bone graft composition can be important when used in a minimally invasive posterolateral lumbar fusions. In such procedures, a rasp can be used with or without a graft delivery system. In some embodiments, a bone graft composition is loaded into an elongate tube and placed in a rasp or placed directly into rasp lumen. A delivery system or push rod can be used to push the bone graft composition out of the rasp to a decorticated area on the facet joints and/or transverse processes. During this type of minimally invasive procedure, the bone graft cannot be seen under the skin, muscle, and tissue. A surgeon can use the radiopacity of the bone graft composition to ensure bone graft is placed in the proper position.

In some embodiments, after delivery of the bone graft over one or more facets and/or transverse processes, the rasp, such as rasps 700a-b, and/or delivery system may be removed. Following removal of the rasp and/or delivery system, any incisions can be sutured.

Although the methods outlined above are generally described in an order of implanting an implant followed by use of a rasp to decorticate bone and/or deliver bone graft material, in certain embodiments, a rasp may be used first to decorticate bone and/or deliver bone graft material before implantation of an implant. In other embodiments, a method may include implantation of an implant without additionally using a rasp to decorticate bone and/or deliver bone graft material or use of a rasp to decorticate bone and/or deliver bone graft material without implantation of an implant.

Methods for decorticating bone and/or delivering bone graft material to a surgical location using the rasps, such as rasps 700a-b, and delivery systems and devices described herein can provide for a reduced number of incisions, reduced blood loss, reduced scarring, decreased risk for infection, and reduced time in the operating room. In contrast, some conventional techniques involve muscle stripping, facial cutting, and comparatively more blood loss.

In some embodiments, rasps described herein, for example, rasps 700a-b, can be used to rasp adjacent transverse processes (for example, a transverse process of an inferior vertebral body and a transverse process of a superior vertebral body adjacent the inferior vertebral body) using a single incision. In some embodiments, the incision is a midline incision. In certain embodiments, the incision can preferably be between 2 cm and 3.5 cm in length. However, in some procedures, the size of the incision may larger or smaller depending on the number of vertebral levels to be fused. In some embodiments, the size of the incision can be between 1 cm and 9 cm in length. The incision can be made about one finger breadth lateral to the facet joint between the superior and inferior vertebral bodies. The rasp can be advanced through the incision to a first transverse process of one of the superior and inferior vertebral bodies. In some embodiments, the rasp is advanced through the musculature and the fascia, for example, to avoid resistance from the fascia during the rasping procedure. In certain embodiments, the rasp can be advanced through the incision to a first transverse process of one of the superior and inferior vertebral bodies with the tip 706 facing a second transverse process of the other of the superior and inferior vertebral bodies. For example, if the first transverse process is positioned on the inferior vertebral body, the tip 706 can be pointed in the superior direction. If the first transverse process is positioned on the superior vertebral body the tip 706 can be pointed in the inferior direction. Orienting the tip towards the second transverse process can facilitate movement of the rasp to the second transverse process by facilitating dissection using the tip 706 between the two transverse processes without requiring rotation of the rasp. The first transverse process can be rasped laterally and medially and/or cephalad and caudad. After rasping the first transverse process, the rasp can be moved to the second transverse process, for example, without removing the rasp from the incision. The tip 706 can dissect tissue as the rasp is moved to the second transverse process from the first transverse process. After the rasp is moved to the second transverse process, the second transverse process can be rasped laterally and medially and/or cephalad and caudad. After rasping of the second transverse process, the rasp can be used to deliver bone graft material to the second transverse process. The rasp can be moved back towards the first transverse process while delivering bone graft material to supply bone graft material between the first transverse process and the second transverse process for fusion. After the rasp returns to the first transverse process, the bone graft can be delivered to the first transverse process. In some embodiments, the rasp can be rotated between the second transverse process and the first transverse process while delivering bone graft material to create a wider dispersion of the bone graft material between the first and second transverse processes for fusion of the first and second transverse processes. The curvature and length of the curved section 704 of the rasp can facilitate a wider dispersion of the bone graft material. For example, in some embodiments, the distal end 706 of the rasp can extend 10 mm or about 10 mm laterally beyond the edge or diameter of the connection section 708. In other embodiments the distal end 706 can extend between 0 mm and 20 mm, between 5 mm and 15 mm, 6 mm, 7 mm, 8 mm, 9 mm, 11 mm, 12 mm, 13 mm, 14 mm, or any other suitable distance or within any other suitable range of distances laterally beyond the edge or diameter of the connection section 708. The curvature and length of the curved section may also allow for movement between and rasping of the two transverse process with a reduced incision size, reduced force, and/or reduced damage to other tissue in comparison to a rasp in which there is no lateral extension. In some embodiments, the transverse process of the inferior vertebral body can be the first transverse process and the transverse process of the superior vertebral body can be the second transverse process. In some embodiments, the transverse process of the superior vertebral body can be the first transverse process and the transverse process of the inferior vertebral body can be the second transverse process. In some embodiments, the rasps describes herein, such as rasps 700a-b, can be used to rasp and/or deliver bone graft to a facet joint and to rasp and/or deliver bone graft to a transverse process using the same incision.

In some embodiments, the rasps described herein, such as rasps 700a-b, can be used in mini open or open orthopedic or spine surgeries. For example, in some embodiments, the rasp can be used as an alternative to burrs, cobb elevators, or other conventional rasps. In some embodiments, the rasps described herein, such as rasps 700a-b, have a larger footprint (i.e., can contact a larger surface of the bone), staggered teeth, and bone graft delivery to the decorticated area.

In some embodiments, the rasps described herein, such as rasps 700a-b, provide a surgeon with tactile feedback, which can indicate that the bone is being rasped. For example, the surgeon can grip the rasp and feel the grinding of bone during use of the rasp. By feeling the grinding of the bone, the surgeon can detect when a majority or an entirety of a bone surface, such as a transverse process, is cleared from soft tissue to facilitate a larger or maximized area of soft tissue for fusion to be achieved. This case be performed for rasping between in medial and lateral directions and/or cephalad and caudal directions.

In some embodiments, a rasp having a curved section 704 and a curved lumen, such as rasps 700a-b, can be advantageous for minimally invasive applications.

The rasps 700a-b can be made of a metallic, radiopaque material to facilitate visualization on, for example, fluoroscopy or x-ray. Alternatively, the rasps 700a-b may be made of another material, for example a durable medical plastic or a composite material, and may include markers to facilitate visualization.

In some embodiments, one or more components that act as a register for image guidance can be attached to the bone graft delivery system, bone graft delivery device, or rasp, such as rasps 700a-b to register placement on an imaging modality to allow for tracking of the system, device, or rasp, such as rasps 700a-b.

In some embodiments, the bone graft delivery system or device and/or rasp, such as rasps 700a-b, can be used with a navigation system, an augmented reality (AR) system, etc., such as, for example, Lessray, stealth system O-arm, Excelsius GPS, 7D, HOLO, Track-X or a robotic navigation system. In some embodiments, a navigation system can facilitate determination of real time anatomical positioning in relation to the rasp, such as rasps 700a-b, and/or bone graft delivery system or device. In some embodiments, as opposed to traditional fluoroscopy, the navigation system is a three-dimensional navigation system. Fluoroscopy is only two-dimensional as opposed to three-dimensional. In contrast to fluoroscopy, such navigation systems may not require multiple or excessive radiation exposures during surgery.

In some embodiments, navigation spheres are used to track and register surgical instruments used during orthopedic and spine surgery. When decorticating bone using the rasp there are delicate structures such as nerves and blood vessels that surgeons need to stay away from. Because these anatomical bony structures are under the muscle, they are not visible. This can make the procedures described herein, including posterior lateral fusion, dangerous because the surgeon essentially is performing the procedure without visualization or using fluoroscopy which does not provide an accurate depth measurement. Fluoroscopy images may also be blurry or unclear if a patient is overweight or the imaging source is older or not properly calibrated.

In certain embodiments, the spheres or another navigation register can be anchored to the proximal end of a rasp, a delivery tube, a dilator, or a guide as described herein. In certain embodiments, navigation spheres may be too bulky for placement on a distal end of a rasp, tube, dilator, or guide that enters an incision of a patient.

Navigation can be performed both active and passively. If active, the register may require batteries or laser capability on a small box or other structure to charge and operate. In some embodiments, in order to function properly, three or more spheres or reflective passive markers must register with the navigation tracking system to provide enough points in space for a reliable signal to proceed. The spheres, markers, or register can be built onto the rasp, graft delivery tube, dilator, or guide or can come as separate modular components that can be snapped, screwed, slid over, clamped or otherwise anchored to the rasp, rasp handle, graft delivery tube, dilator, or guide. The spheres or register can be disposable or reusable. The spheres or register can be formed of different types of reflective materials including metal, plastics, ceramics, polymers, glass, or any other suitable material. Once anchored, the spheres or register may be secured in place permanently or removably. In some embodiments, the spheres or register can include a push button for release or other release mechanism to rotate or remove the device.

In some embodiments, the spheres or register may be preset before a surgery is performed if, for example, a rasp, bone graft delivery system, dilator, or guide is used often. This will ensure the calibration is set properly to reach a desired spot that needs to be decorticated or that requires graft to be delivered for fusion. In other embodiments, the spheres or register can be calibrated during surgery, for example, if the rasp, bone graft delivery system, dilator, or guide are being used for the first time or infrequently.

In some embodiments, once the spheres or register are calibrated, the surgeon can proceed with 3D visualization of the surgical site. Once the surgical site is identified, the surgeon can drop the rasp instrument to an orthopedic site such as a transverse process and begin decortication using a mechanical rasp, file, burr or other object to remove cortical bone and create a bed for bone graft and fusion. The graft can then be delivered by actuating the delivery mechanism to advance bone graft out of the rasp to the desired surgical site.

Figure 19A:
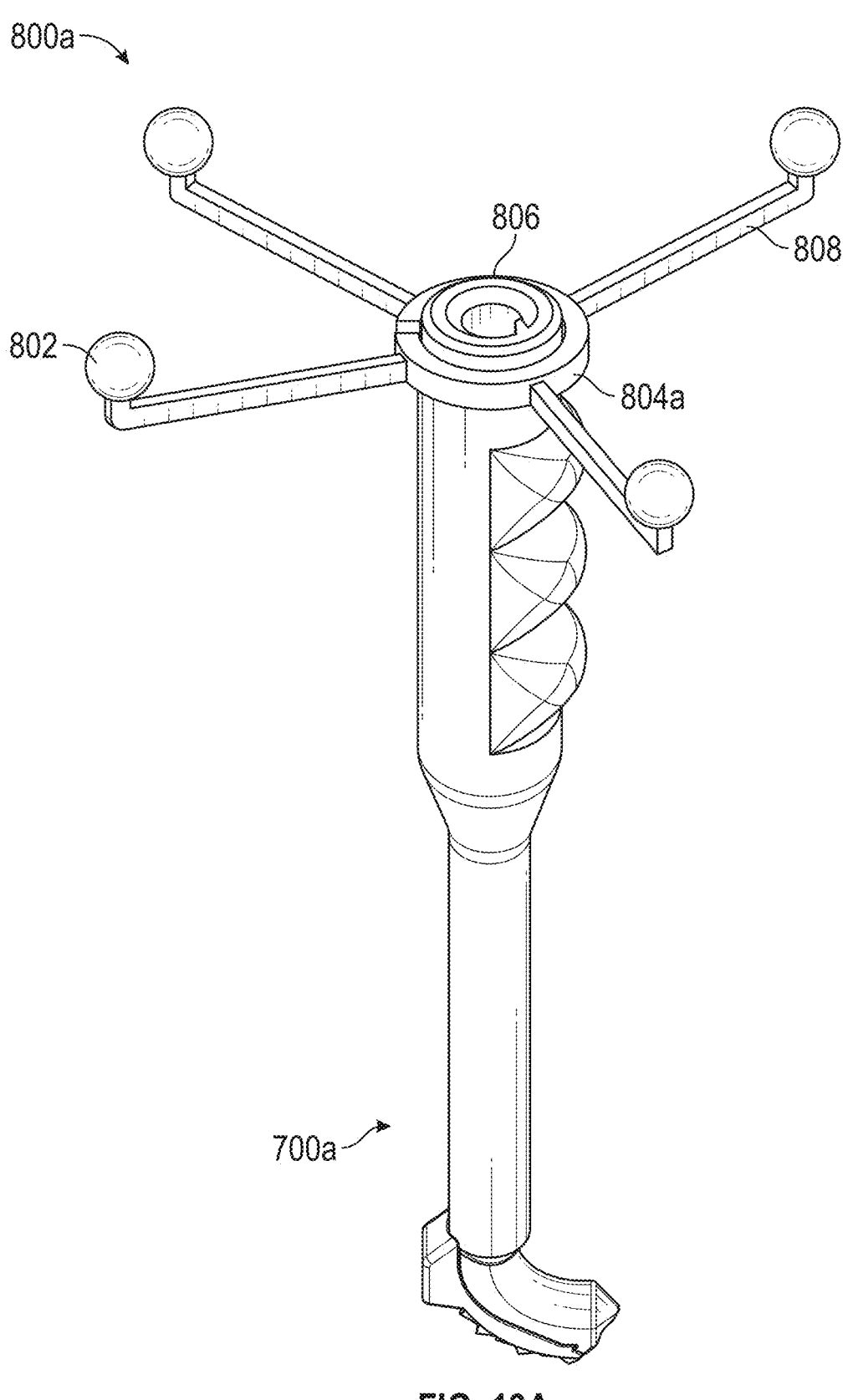
FIG. 19A illustrates a perspective view of an embodiment of a rasp and a navigation system.
Figure 19B:
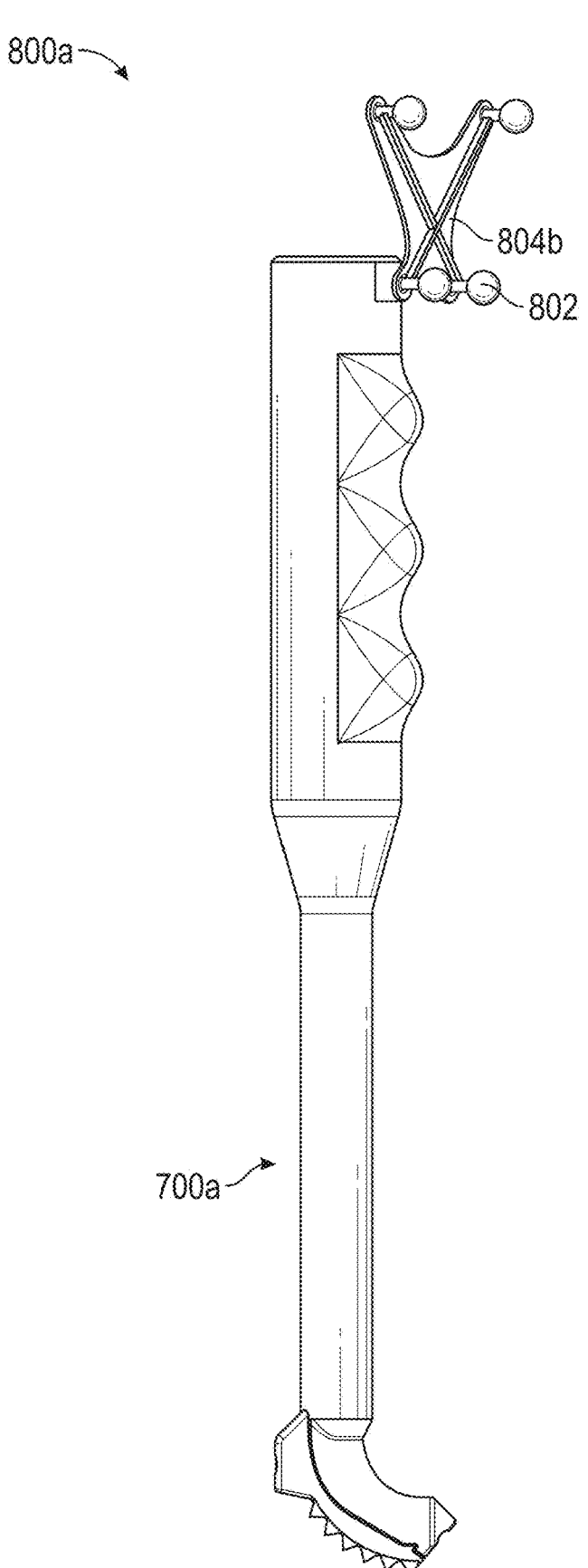
FIG. 19B illustrates a perspective view of an embodiment of a rasp and a navigation system.

FIGS. 19A-B depict examples of navigation systems 800a and 800b having one or mor navigation spheres 802. As shown in FIG. 19A, the navigation spheres 802 are distributed radially about a proximal end of the rasp 700a. The spheres 802 are coupled to a frame 804a having a cylindrical section 806 configured to couple to the handle section 702 and a plurality of arms 808 extending outwardly from the cylindrical section 806.

As shown in FIG. 19B, the navigation system 800b includes a frame 804b coupled to one side of the handle section 702. The spheres 802 are distributed near corners of the frame 804b. As shown in FIG. 19B the frame 804b includes two spheres positioned superior to a proximal end of the rasp 700a and two spheres positioned inferior to the proximal end of the rasp 700a.

Figure 20A:
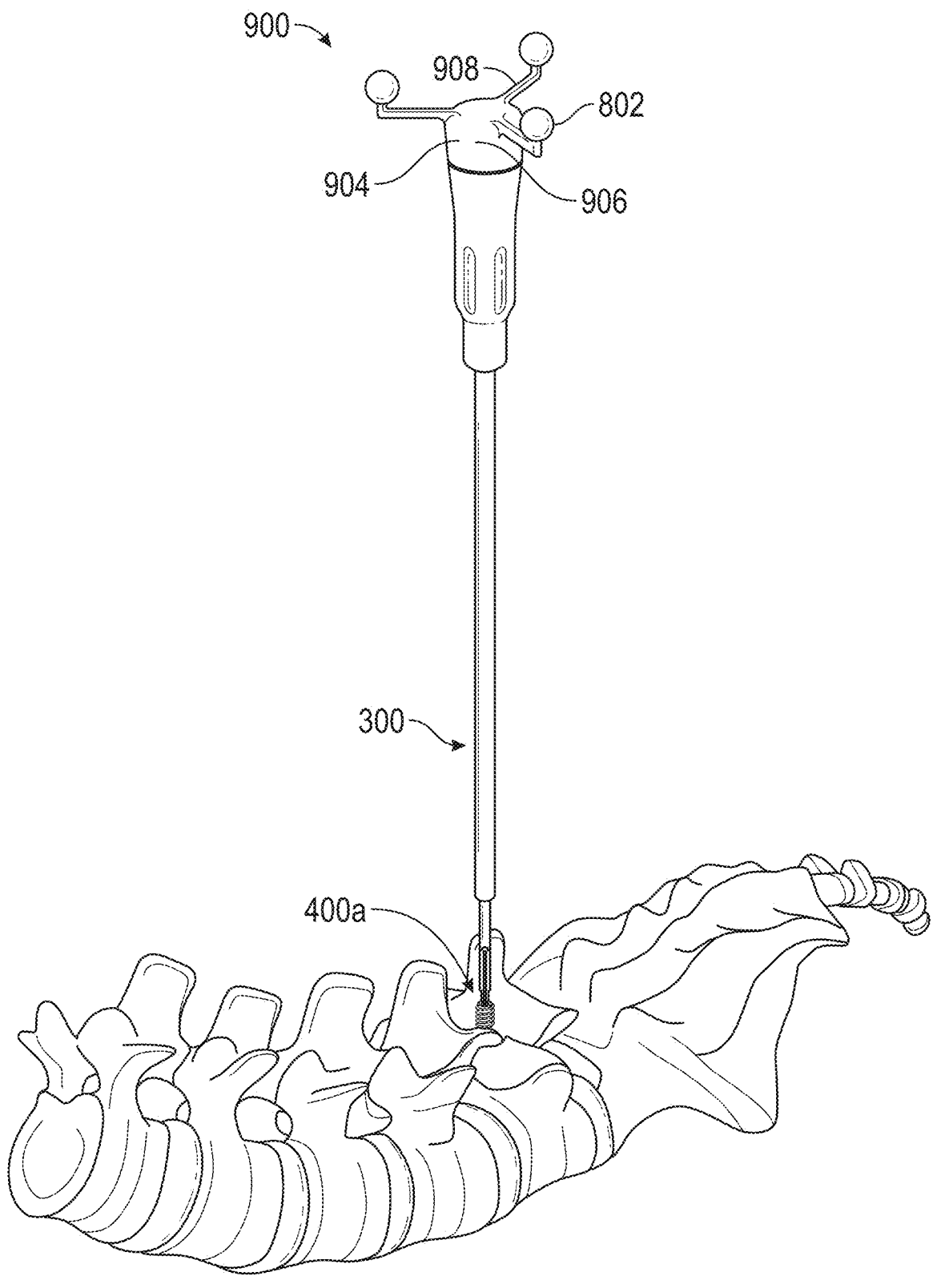
FIG. 20A illustrates a perspective view of an embodiment of an inserter, a navigation system, and an implant positioned at a facet joint.
Figure 20B:
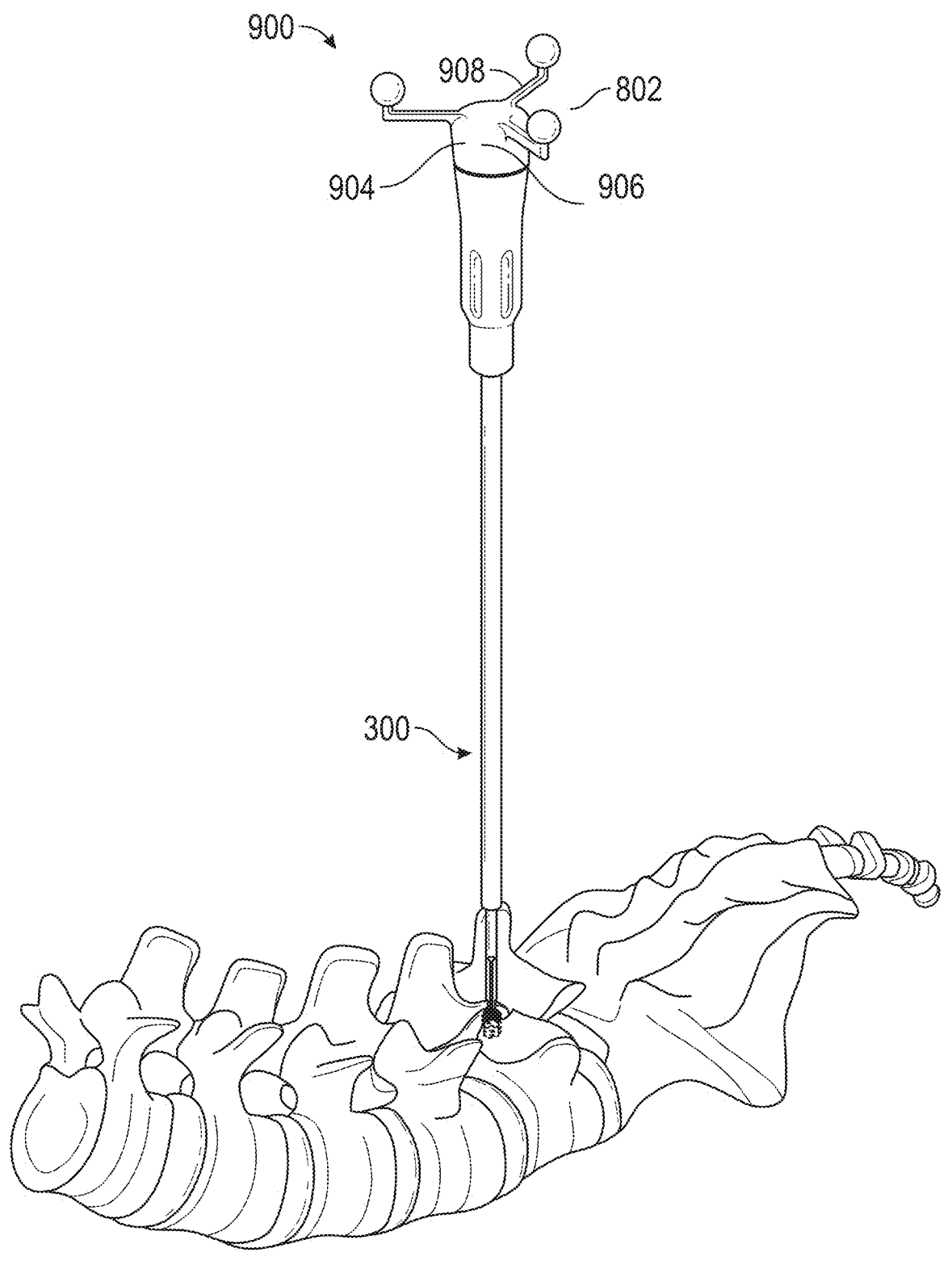
FIG. 20B illustrates a perspective view of an embodiment of an inserter, a navigation system, and an implant, showing the implant positioned within a facet joint.

FIGS. 20A and 20B depict an example of a navigation system 900 coupled to the inserter 300. As shown, the navigation system 900 can include a plurality of spheres 802 coupled to a frame 904. The frame 904 can include a cap 906 positioned over a proximal end of the handle of the inserter 300 and a plurality of arms 908 extending radially outward from the cap. In some alternative embodiments, the navigation system 900 may couple to the body of the inserter instead of the handle.

In some patients, an osteophyte on the facet joint may obscure the view of the joint line, for example if using fluoroscopy. In some embodiments, navigation can facilitate determination of real time anatomical positioning of the inserter and implant relative to the joint line to facilitate positioning of the implant within the facet joint. Such navigation can facilitate positioning of the implant within the facet joint in the presence of an osteophyte.

Procedures for treating the facet joint and transverse process are discussed herein. However, the devices, systems, and methods described herein may be used for other surgical procedures.

Figures 22A, 22B:
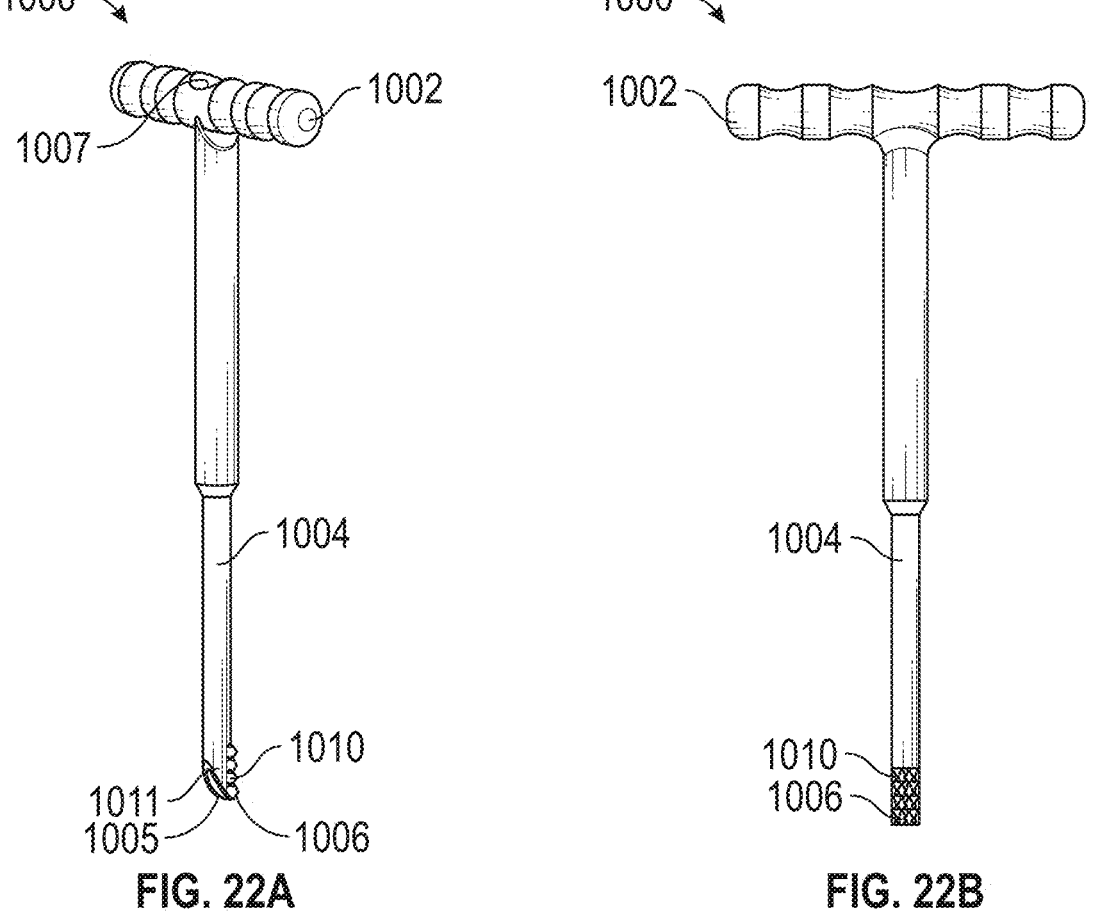
FIG. 22A illustrates a perspective view of an embodiment of a rasp.
FIG. 22B illustrates a front view of the rasp of FIG. 22A.

FIGS. 22A and 22B show an embodiment of a rasp 1000. In some embodiments, the rasp 1000 can include any of the same features or functions as the rasps 700a and 700b. The rasp 1000 can include a handle section 1002 which may be coupled to a tubular section 1004 extending distally from the handle section. The handle 1002 can be a straight handle, a pear-shaped handle, a t-handle, or any other suitable handle shape. In certain embodiments, a t-handle may provide additional torque. In some embodiments, the handle section 1002 can be perpendicular to the tubular section 1004. In some embodiments, the handle section 1002 can extend laterally beyond the circumference of the tubular section 1004. In some embodiments, the handle section 1002 can be detachable. In other embodiments, the handle section 1002 may be integral with the tubular section 1004.

A rasping surface 1010 can extend at least partially or completely around a circumference of the tubular section 1004 at a distal end 1006 of the rasp 1000. In some embodiments, the rasp 1000 includes a smooth surface 1011 on an opposite side of the rasping surface 1010. The rasping surface 1010 can include any of the same or similar features or functions as the rasping surface 710a. The rasp 1000 can include an opening 1005 at the distal end, an opening 1007 at the proximal end with a lumen extending therebetween for the delivery of bone graft material. In some embodiments, the lumen can be straight or generally straight to facilitate the contiguous flow of bone graft material therein.

Figure 22C:
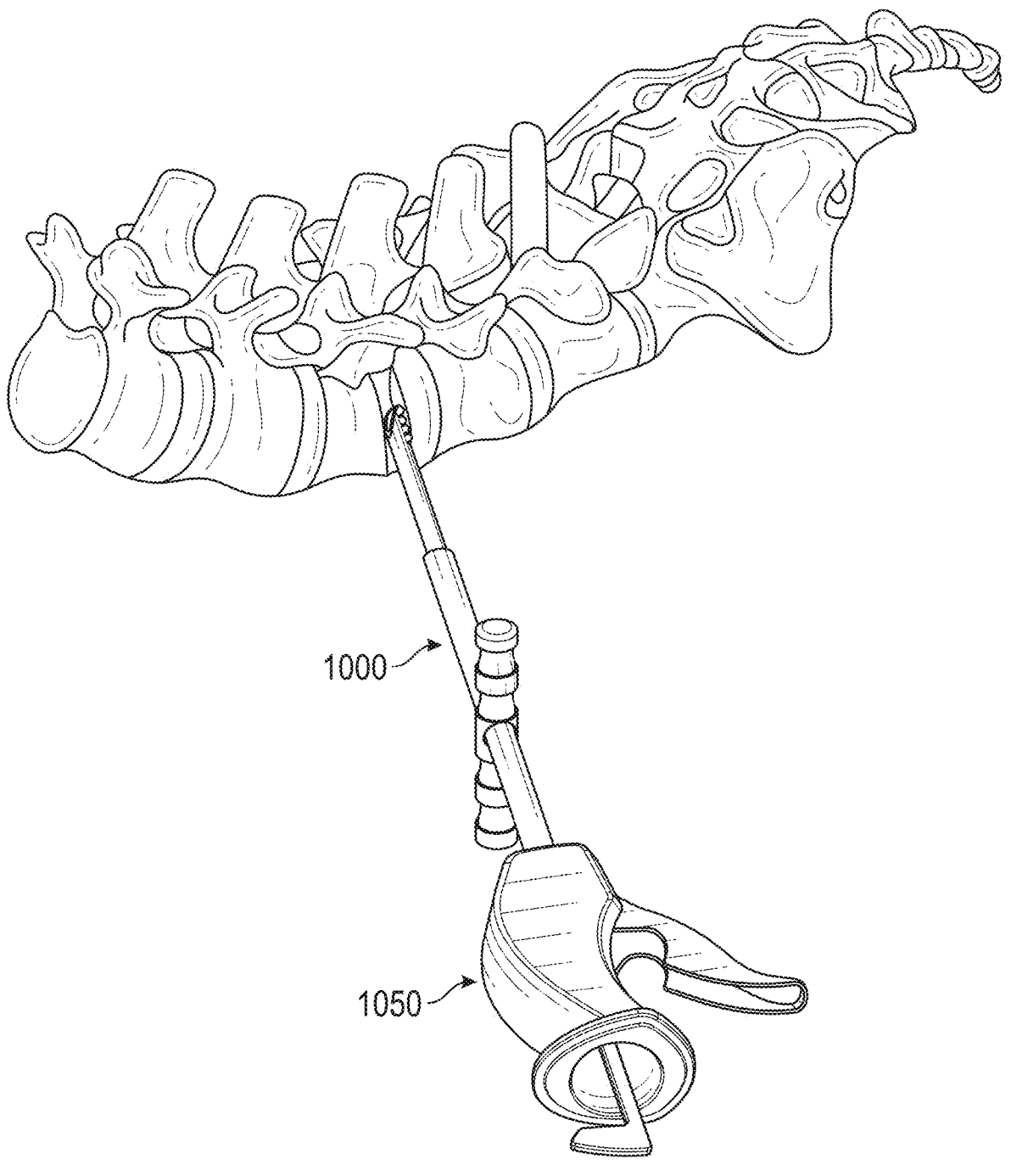
FIG. 22C illustrates a perspective view of the rasp of FIG. 22A positioned within a disc space and a bone graft delivery device.

As shown in FIG. 22C, the rasp 1000 can be used as an intradiscal rasp. The smooth surface 1011 can facilitate passage of the rasp by nerve root during insertion without damaging the nerve root. After the rasping surface 1010 passes the nerve root, the rasp 1000 can be rotated in the disc space so that the rasping surface roughens the endplates to create a bed for bone fusion. In certain embodiments, a t-handle may provide additional torque to rotate the rasp and apply force on the endplates.

Bone graft can be delivered to the disc space through the lumen of the rasp 1000, for example, using a bone graft delivery system 1050 as shown in FIG. 22C or using a funnel. The delivery system 1050 or funnel can be placed within the lumen of the rasp 1000 and, in the case of the delivery system, actuated for the delivery of bone graft material. Using a single rasp to rasp the intradiscal space and deliver bone graft material without removal of the rasp limits the number of times an instrument must pass by the nerve roots in comparison, for example, to procedures in which a rasping instrument must first be removed and a second instrument inserted to deliver bone graft material. Using a single rasp 1000 for delivery of bone graft material may also decrease total surgery time and provide convenience to a user. In some embodiments, the opening 1005 can open at a distal most portion of the rasp 1000 to allow graft to be delivered further into the disc space.

In some embodiments, the rasp 1000 can act as a lumen or working channel. For example, after the rasp 1000 passes the nerve roots, one or more instruments, such as endoscopes for visualization or pituitary instruments or graspers for disc removal, can be introduced through the lumen or working channel of the rasp 1000. Introduction of the instruments through the lumen or working channel of the rasp 1000 can reduce or prevent damage to the nerve roots that may occur if each instrument was introduced and/or removed separately from the rasp. In some embodiments, after the rasp 1000 has passed the nerve roots, the rasp 1000 can be used, in combination with one or more additional instruments, to visualize the surgical location, to remove a disc, and/or to create bone by rasping and delivery of bone graft material to facilitate bone fusion.

The rasp 1000 may be used in a variety of different spinal fusion procedures including, but not limited to, fusion procedures in which nerve roots are in close working proximity, such as oblique lateral interbody fusion, TLIF or PLIF.

Additional details regarding implants, inserters, rasps, bone graft delivery devices and systems, and related accessories that may be used in the embodiments described herein are described in U.S. Patent Application Publication No. 2020/0306055, which is incorporated by reference herein in its entirety and for all purposes.

Removal of a screw in a minimally invasive surgery can be difficult due to tissue creep. In certain instances, locating a head of the screw can be difficult due to the relatively small size of the incision used in minimally invasive surgery. The implant may be buried deep into a patient's bone within the incision. In some instances, for example if an inserter is used to remove the implant, the implant may fall of the tip of the inserter as the inserter is retracted out of the tissue. The implant may then become caught in muscle and tissue making retrieval difficult.

Figures 24A, 24B, 24C:
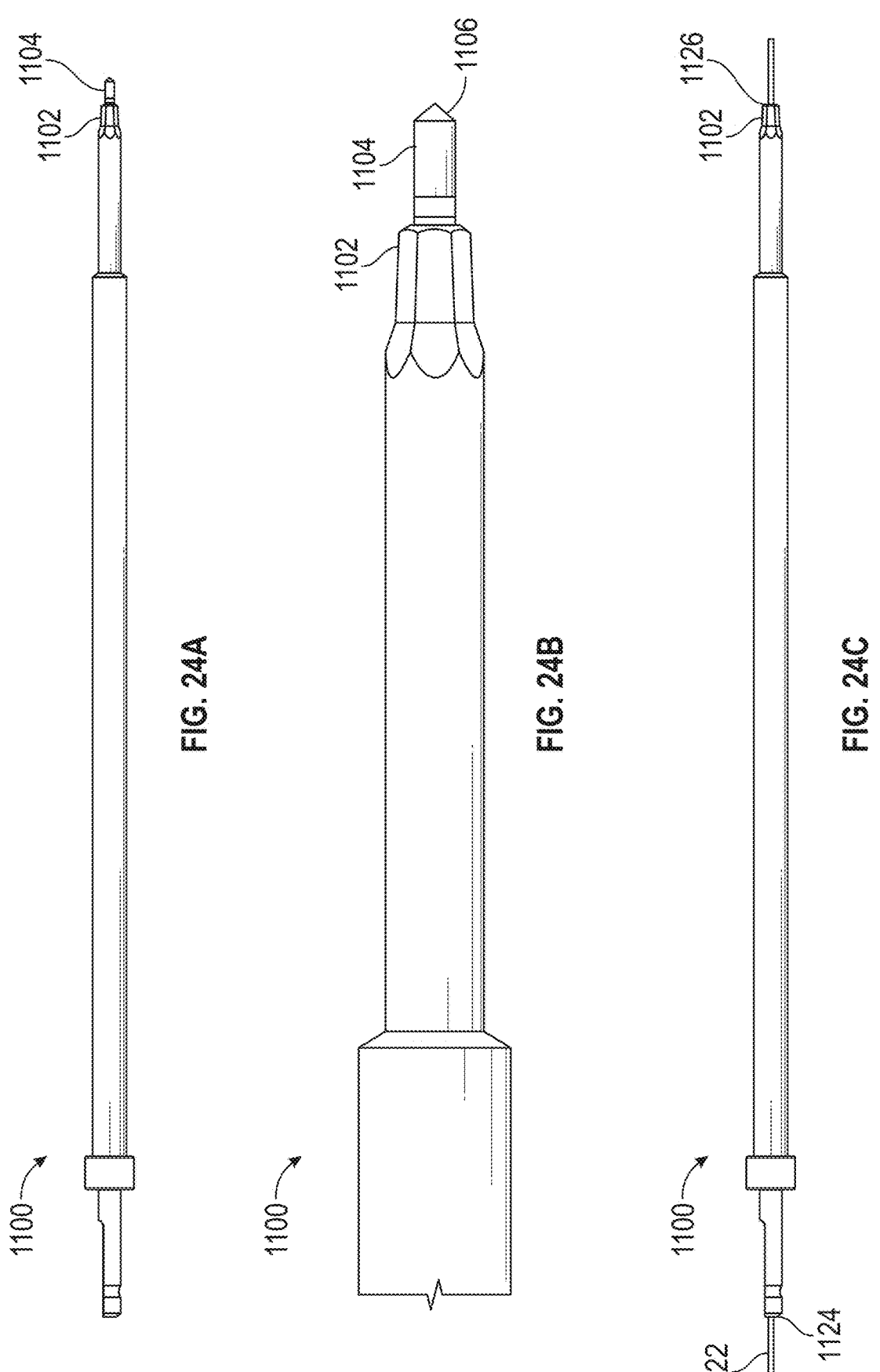
FIG. 24A illustrates a side view of an embodiment of an inserter.
FIG. 24B illustrates an enlarged side view of a distal end of the inserter of FIG. 24A.
FIG. 24C illustrates a side view of an embodiment of a rasp.

FIGS. 24A-24B depict an embodiment of a driver or inserter 1100. The inserter 1100 can generally include any of the same or similar features or functions as the inserter 300. In certain embodiments, the inserter 1100 can include an engagement tip or engagement feature 1102. The engagement tip 1102 can be configured to couple with an implant, such as an intrafacet implant, facet screw, facet dowel, pedicle screw, cortical screw, or any other suitable implant.

The engagement tip 1102 can have any shape suitable for coupling to an implant, such as a screw. For example, the engagement tip 1102 can have a hex pattern, star pattern, square pattern, torx pattern, or any other suitable shape.

In certain embodiments, the inserter 1100 may act as a removal tool or be used as part of a removal system for removing an implant, such as an intrafacet implant, from a surgical location. The inserter 1100 may allow for improved removal of an implant in a minimally invasive surgery.

The inserter 1100 can include a guide tip 1104. The guide tip 1104 can be configured to be received within an interior portion of the implant (e.g., a channel of the implant). In a procedure for removing an implant, the inserter 1100 can be advanced towards the implant and the guide tip 1104 can be inserted into the implant and used to align the engagement tip 1102 with a complementary engagement feature of the implant. The guide tip 1104 can have smaller diameter than the engagement tip 1102 and a complementary engagement feature of the implant configured to receive the engagement tip 1102. The smaller diameter of the guide tip 1104 can allow for easier insertion into an interior of the implant and alignment of the engagement tip 1102 with a complementary engagement feature in comparison to an engagement tip without a guide tip 1104. For example, an engagement tip 1102 may have a cross-sectional shape that substantially corresponds to a cross-sectional shape of a complementary engagement feature of an implant and may require more precise alignment. The guide tip 1104 can be received within the implant before the engagement tip 1102, making it easier to advance and align the engagement tip 1102 with the engagement feature of the implant. In certain embodiments, the guide tip 1104 can include a beveled or tapered distal end 1106, which may allow for easier engagement of the implant.

Figures 25A, 25B:
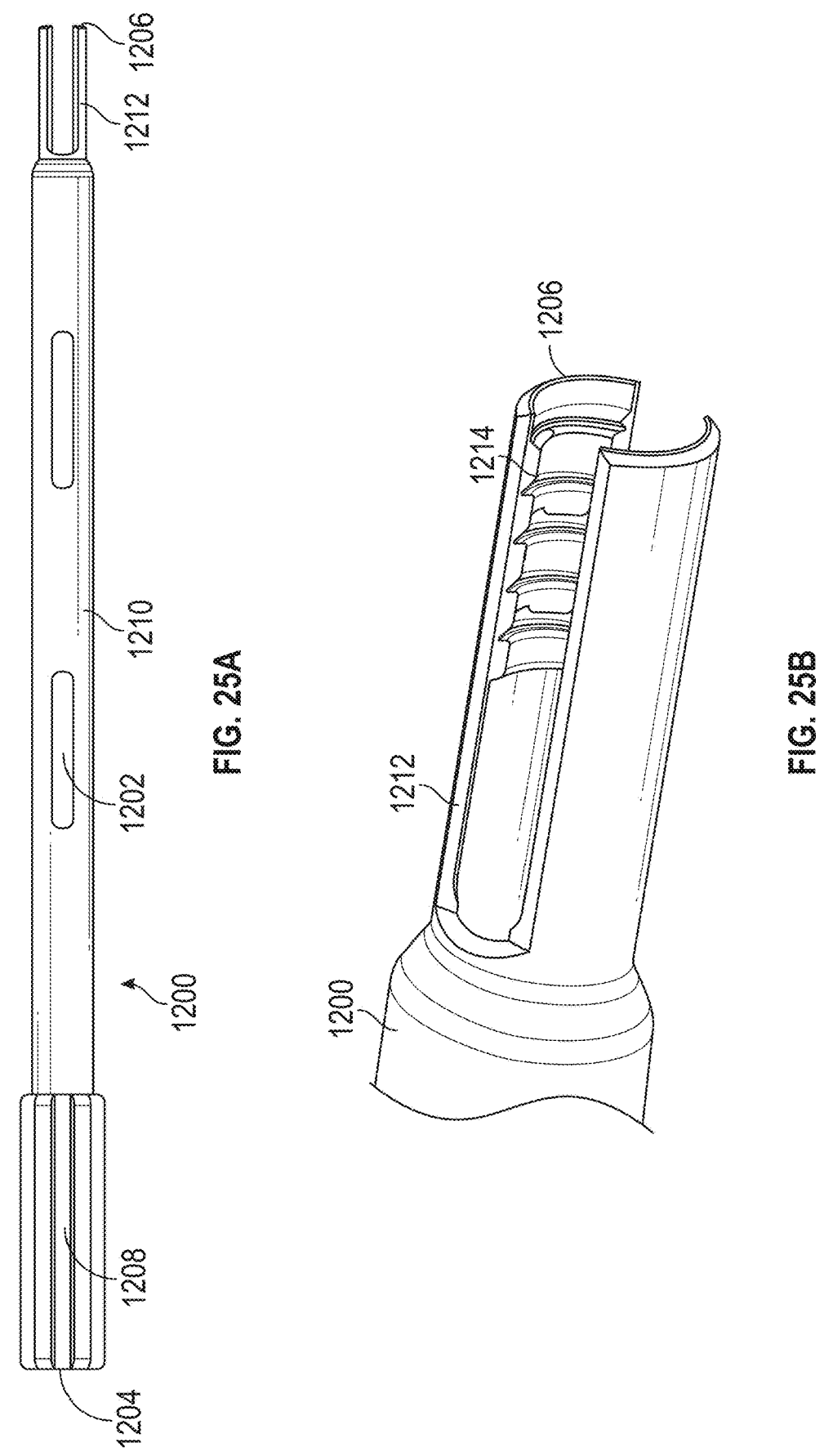
FIG. 25A illustrates a side view of an embodiment of a removal sleeve.
FIG. 25B illustrates an enlarged perspective view of a distal end of the removal sleeve of FIG. 25A.

In alternative embodiments, the inserter 1100 can be cannulated and a guidewire may be used instead of a guide tip 1104. FIG. 24C illustrates an alternative embodiment in which the inserter 1110 is configured to receive a guidewire 1122. In the embodiment of FIG. 24C, the inserter includes a proximal opening 1124, a distal opening 1126, and a lumen extending between the proximal opening 1124 and the distal opening 1126. The guidewire 1122 can be advanced through the inserter and into the interior of the implant. The inserter 1100 can then be advanced and the engagement tip 1102 can be aligned with and coupled to the engagement feature of the implant. FIGS. 25A-25B illustrate an example of an engagement removal sleeve 1200 that may be used with the inserter 1100 to remove an implant from a surgical location (e.g., a facet joint). The removal sleeve 1200 can include a lumen 1202 extending between a proximal end 1204 and a distal end 1206. In certain embodiments, the lumen 1202 can be configured to receive the inserter 1100 therethrough.

The removal sleeve 1200 can include a handle 1208 that can be gripped by a user. The sleeve 1200 can further include one or more windows 1210 that can be used to visualize the inserter 1100 and/or an implant within the lumen 1202.

The removal sleeve 1200 can include a tip 1212 which can be configured to fit over and capture an implant. The tip 1212 can include one or more engagement features 1214 (e.g., threads, ridges, bumps, or any other suitable engagement features) that can be configured to couple with complementary engagement features of the implant. For example, the tip 1212 can include threads configured to mate with complementary threads of an implant. When the engagement features 1214 are coupled with complementary engagement features of an implant, the removal sleeve 1200 can be withdrawn from the surgical location to remove the implant while preventing the implant from falling off the removal sleeve and into tissue.

In certain embodiments, the inserter 1100 can be used to couple the implant with the engagement features 1214 of the removal sleeve 1200. For example, the inserter 1100, can be rotated or otherwise manipulated so that threads of the implant mate with the engagement features 1214, which can be in the form of complementary threads.

FIGS. 26A-26G depict an example of a procedure for removing an implant 400d using the inserter 1100 and removal sleeve 1200.

Figures 26A, 26B:
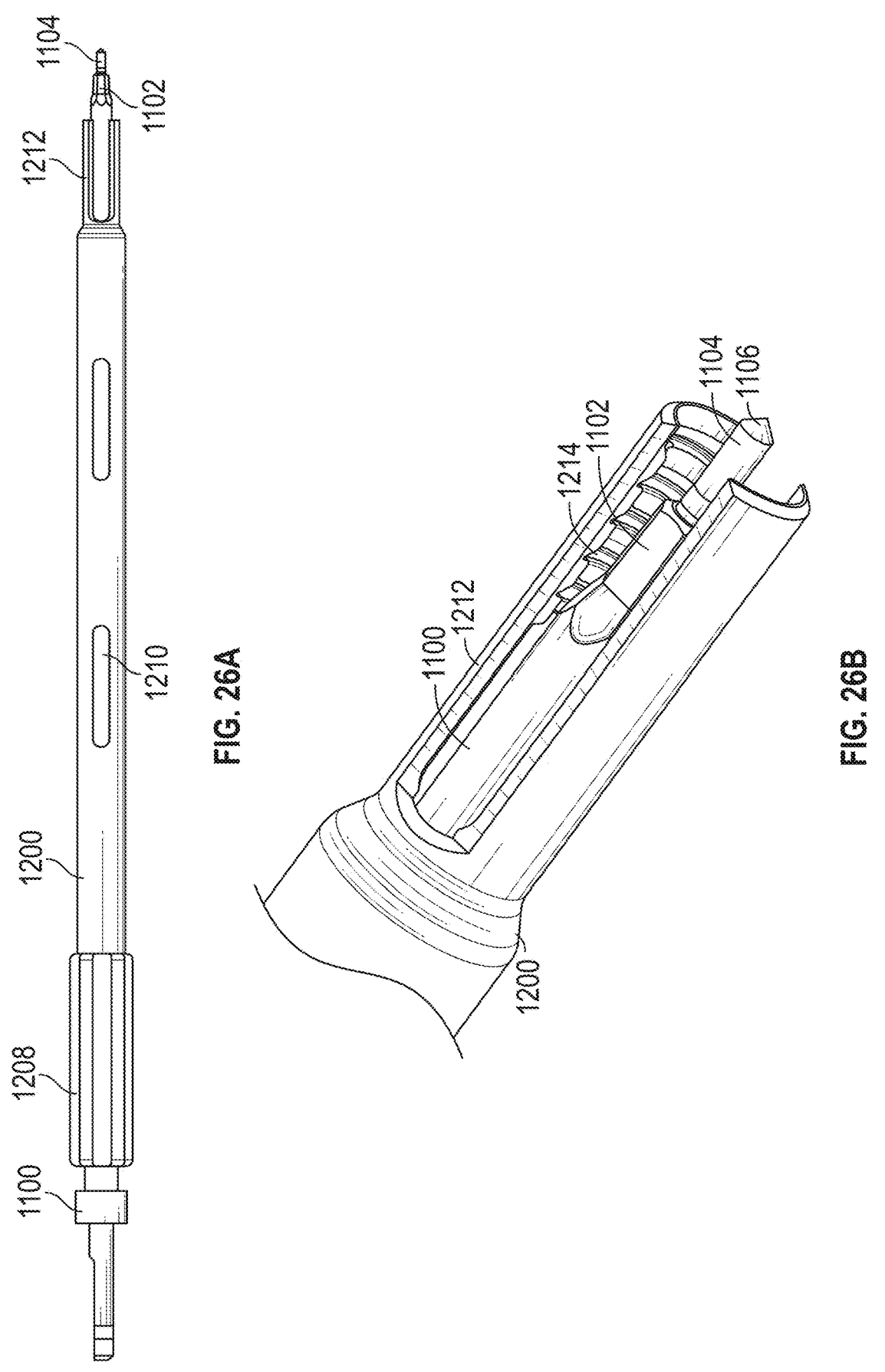
FIG. 26A illustrates a side view of an embodiment of an implant removal system including the inserter of FIG. 24A and the removal sleeve FIG. 25A.
FIG. 26B illustrates an enlarged perspective view of a distal end of the removal system of FIG. 26A.

As shown in FIGS. 26A and 26B, the removal sleeve 1200 can be positioned over the inserter 1100. In some embodiments, the removal sleeve 1200 may receive the inserter through its proximal end 1204. In other embodiments, distal end 1206 may be advanced over the inserter 1100. In certain embodiments, the removal sleeve 1200 and inserter 1100 may be advanced to the surgical location together. In other embodiments, the inserter 1100 may be advanced to the surgical location first and the removal sleeve 1200 may be advanced to the surgical location over the inserter 1100. In other embodiments, the removal sleeve 1200 may be advanced to the surgical location first, and the inserter 1100 can be advanced to the surgical location through the removal sleeve 1200. In certain embodiments, the inserter 1100 and removal sleeve 1200 can be advanced to the facet joint using a guide, such as guide 108, or dilator. In certain embodiments, removal of the implant may be performed using the inserter 1100 and removal sleeve 1200 after implanting the implant using any of the instruments or procedures described herein.

Figures 26C, 26D:
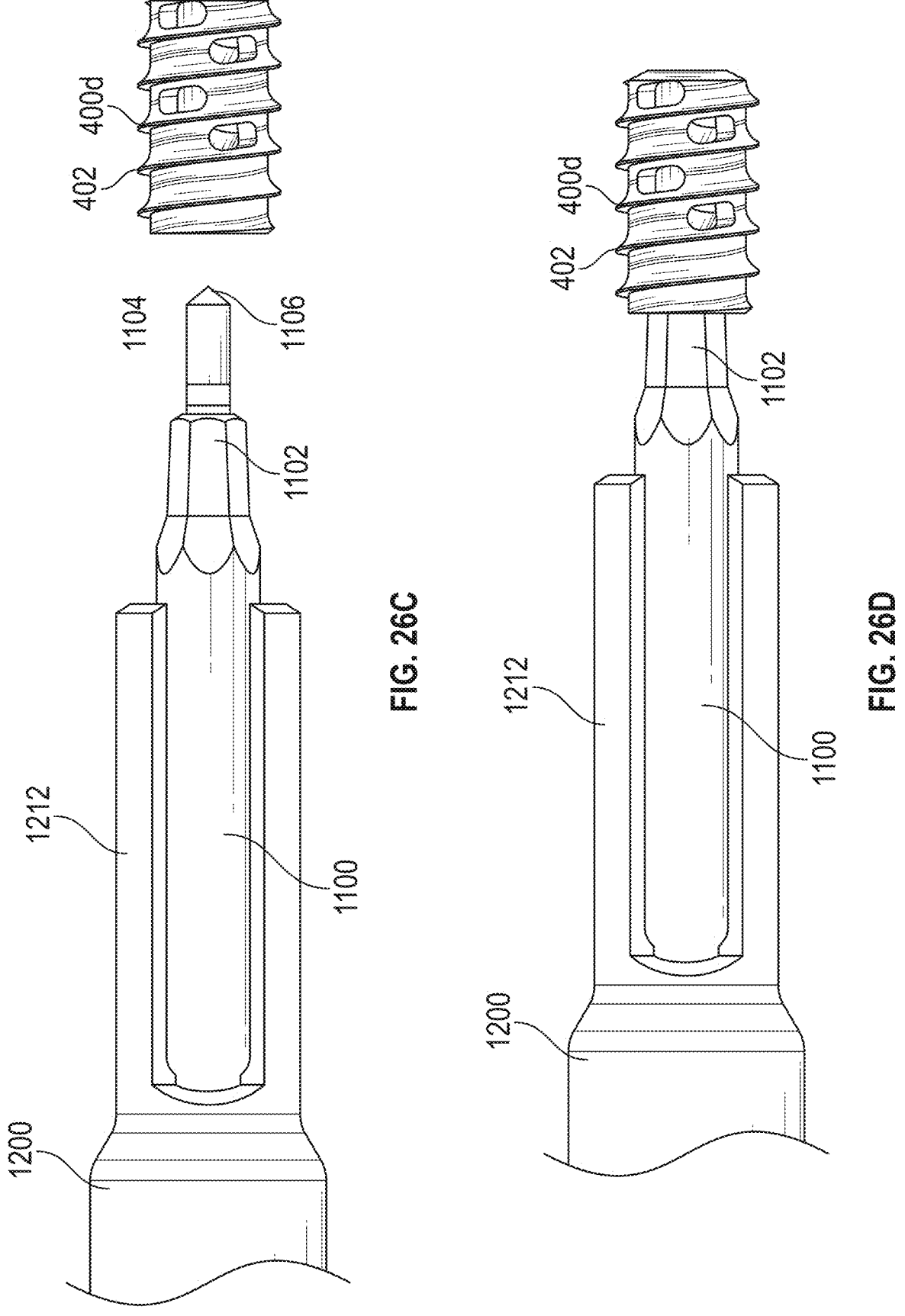
FIG. 26C illustrates an enlarged side view of a distal end of the removal system of FIG. 26A coupled to the implant of FIG. 26B.
FIG. 26D illustrates an enlarged side view of a distal end of the removal system of FIG. 26A coupled to the implant of FIG. 26B.
Figure 26E:
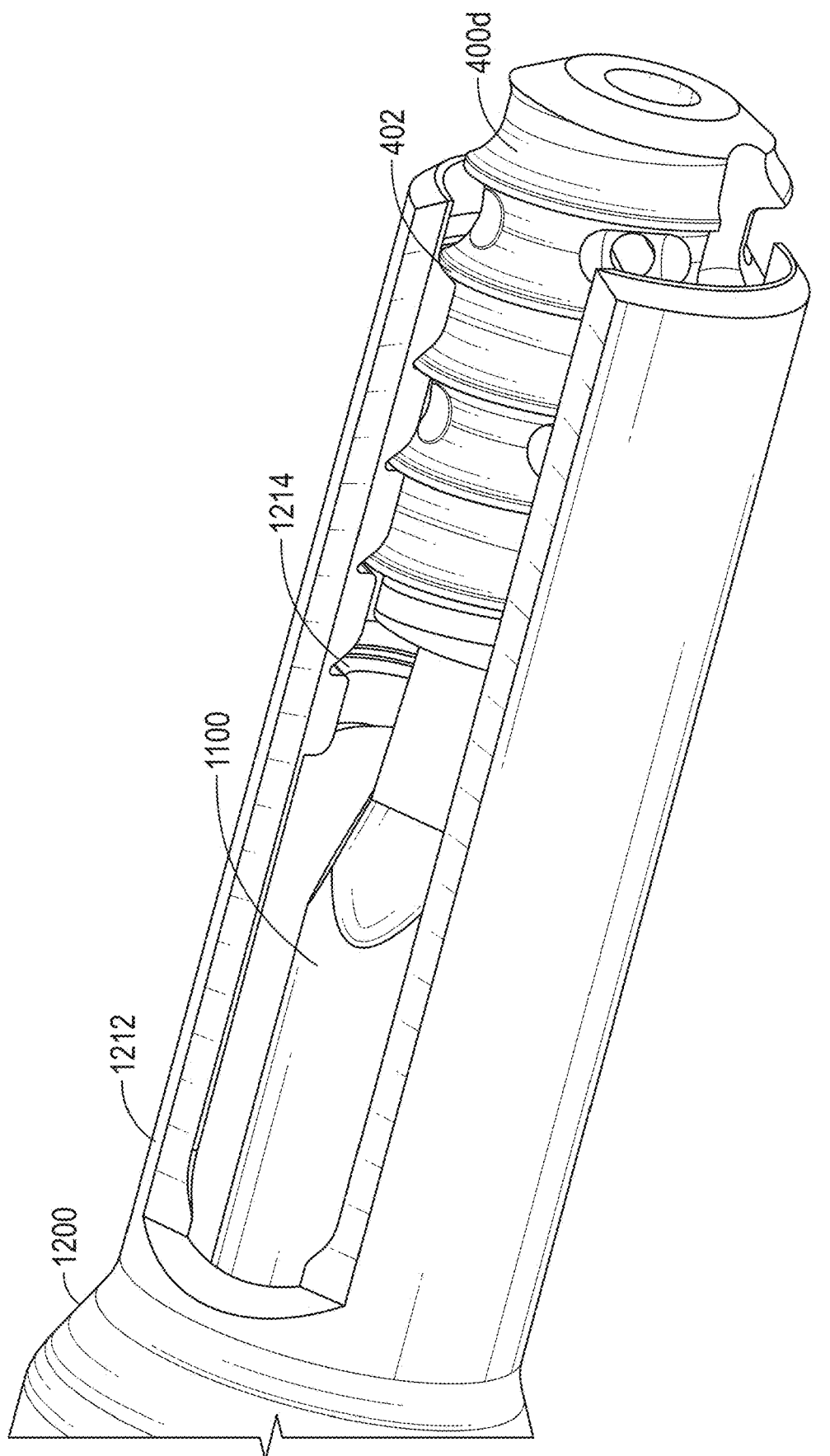
FIG. 26E illustrates an enlarged perspective view of a distal end of the removal system of FIG. 26A coupled to the implant of FIG. 26B.
Figure 26F:
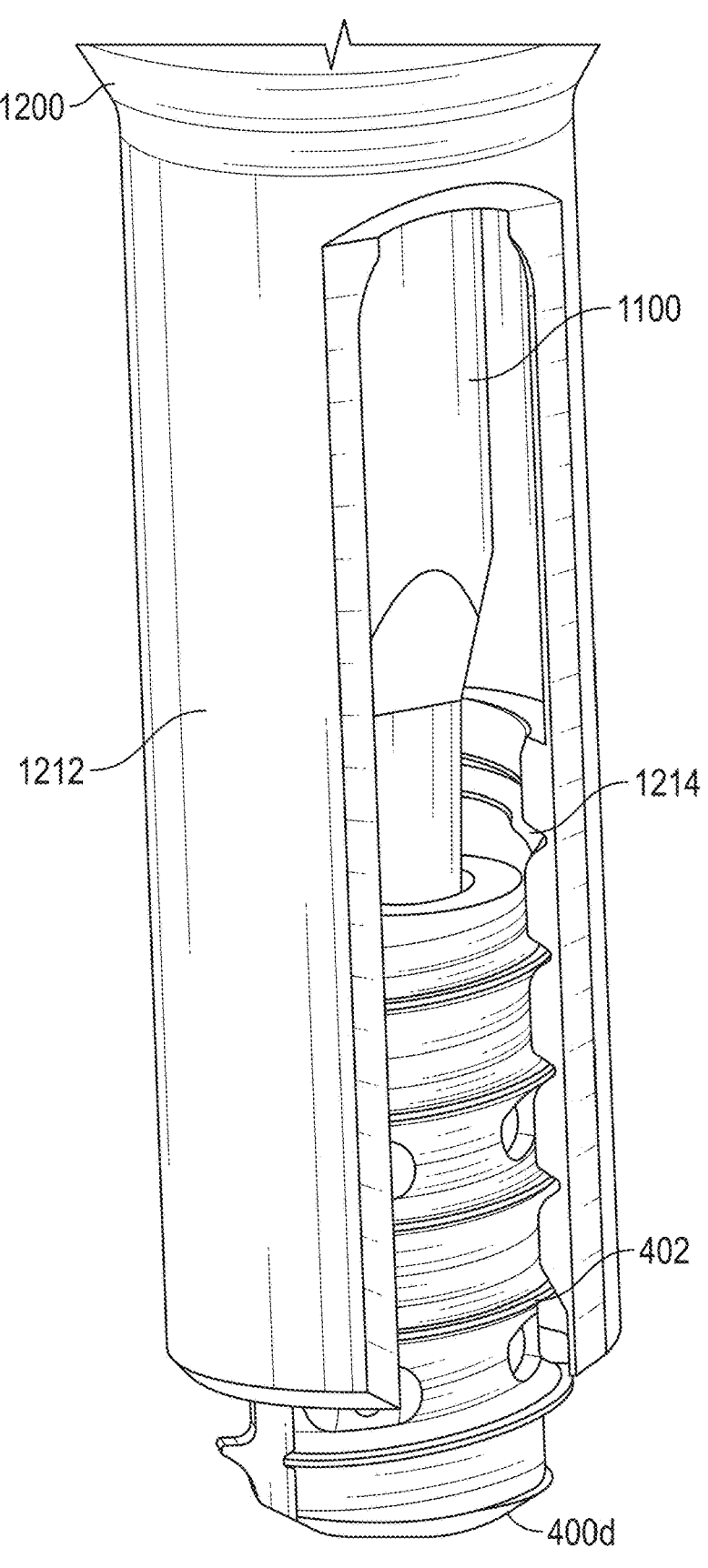
FIG. 26F illustrates an enlarged perspective view of a distal end of the removal system of FIG. 26A coupled to the implant of FIG. 26B.
Figure 26G:
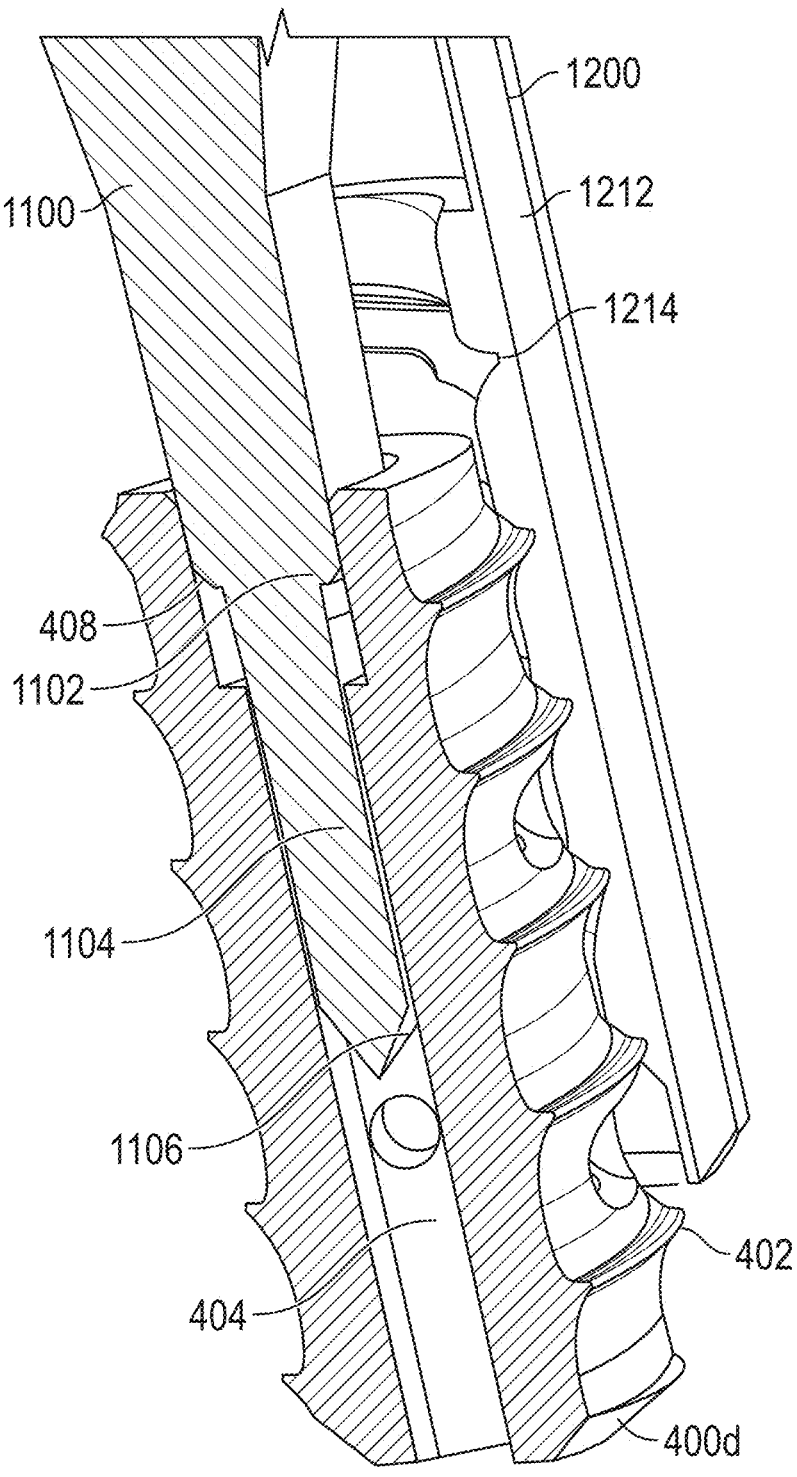
FIG. 26G illustrates an enlarged cross-sectional view of a distal end of the removal system of FIG. 26A coupled to the implant of FIG. 26B.

As shown in FIG. 26C, the tip 1104 can be advanced to the implant 400d. The guide tip 1104 can be inserted into the channel 404 of the implant 400d and used to align and couple the engagement tip 1102 with the engagement feature 408 of the implant 400d, as shown in FIG. 26D.

The inserter 1100 can be rotated to back the implant 400d out of the surgical location. As the implant 400d is backed out of the surgical location, the sleeve 1200 can be advanced to meet the implant, and the inserter 1100 can continue to be rotated to mate the engagement features 402 of the implant 400d with the engagement features 1214 of the removal sleeve 1200. After the implant 400d is mated with the sleeve 1200, the sleeve 1200 and the inserter 1100 can be withdrawn to remove the implant 400d from the surgical location. In other embodiments, the inserter 1100 may be first, and then the sleeve 1200 can be withdrawn to remove the implant 400d.

FIGS. 27A-D depict an embodiment of a rasp 1300. The rasp 1300 can generally include any of the same or similar features as the rasps 700a, 700b, and 1000. The rasp 1300 extends between a proximal end 1318 and a distal end 1306. The rasp 1300 can include a rasping tip 1307 having rasping surfaces 1310a and 1310b extending from opposing generally rectangular surfaces 1312a and 1312b. In certain embodiments, the surface 1312a and the surface 1312b can be a top surface and a bottom surface, respectively, of the rasping tip 1307. The rasping tip can include generally flat side surfaces 1314a and 1314b. The distal end 1306 can be a pointed or wedge shaped distal end of the rasping tip 1307.

Figure 27A:
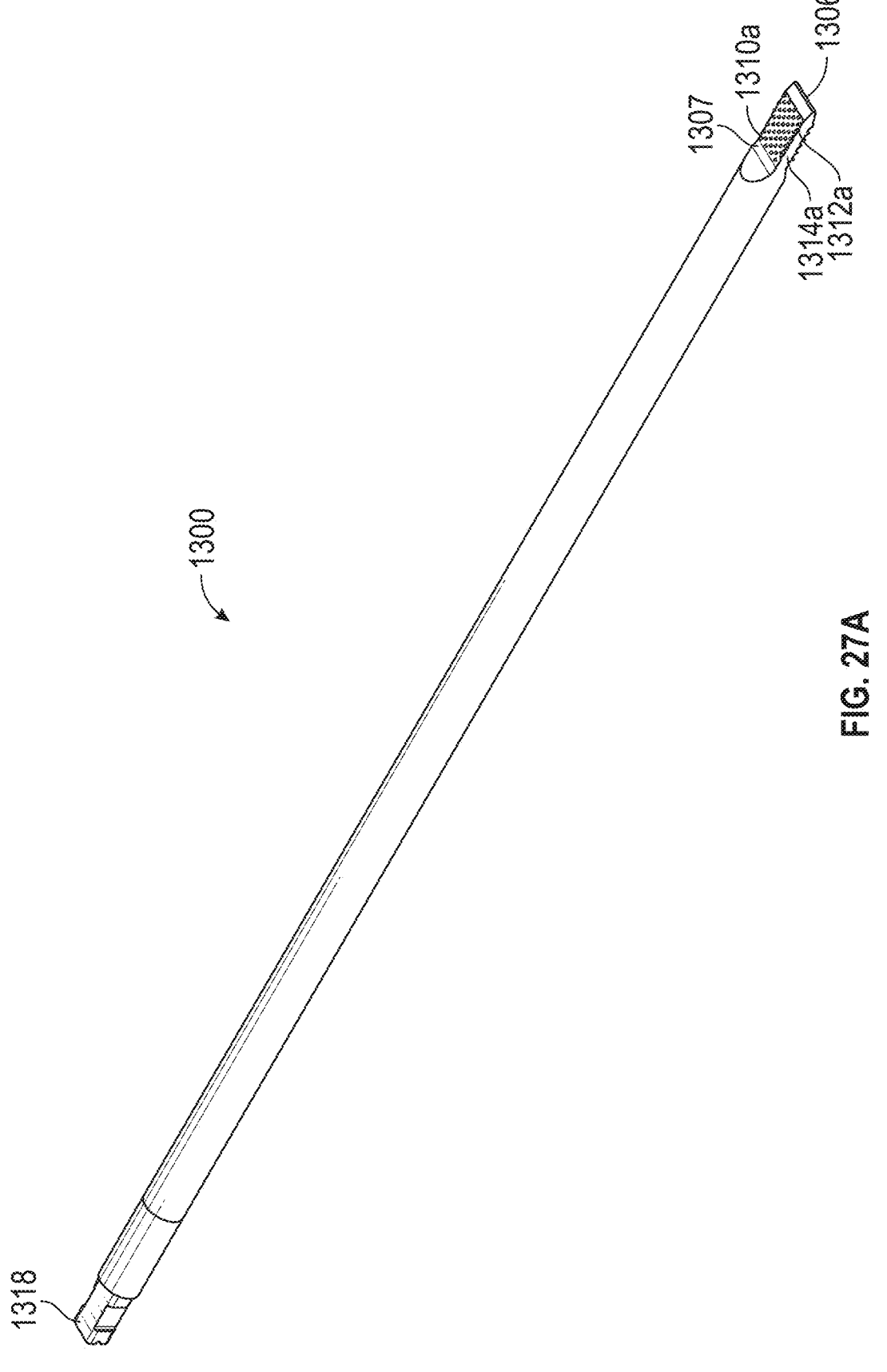
FIG. 27A illustrates a perspective view of an embodiment of a rasp.
Figure 27B:
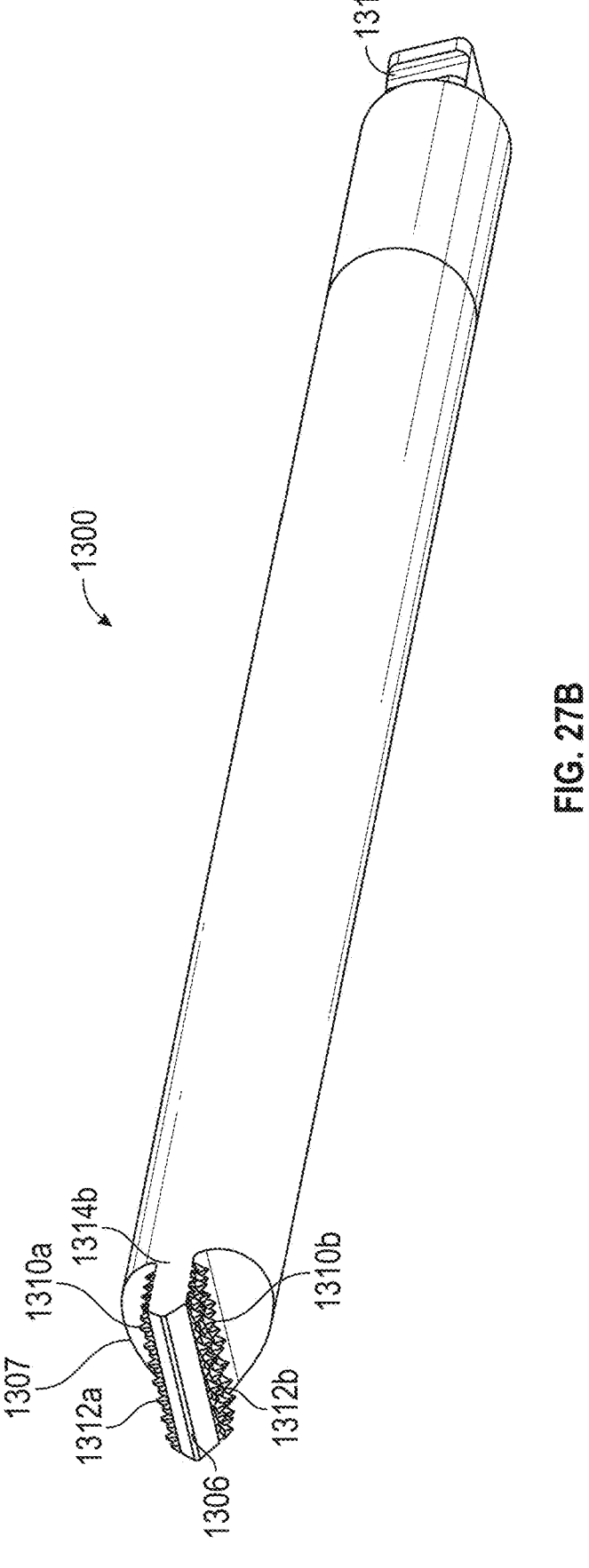
FIG. 27B illustrates a perspective view of the rasp of FIG. 27A.
Figures 27C, 27D, 27E:
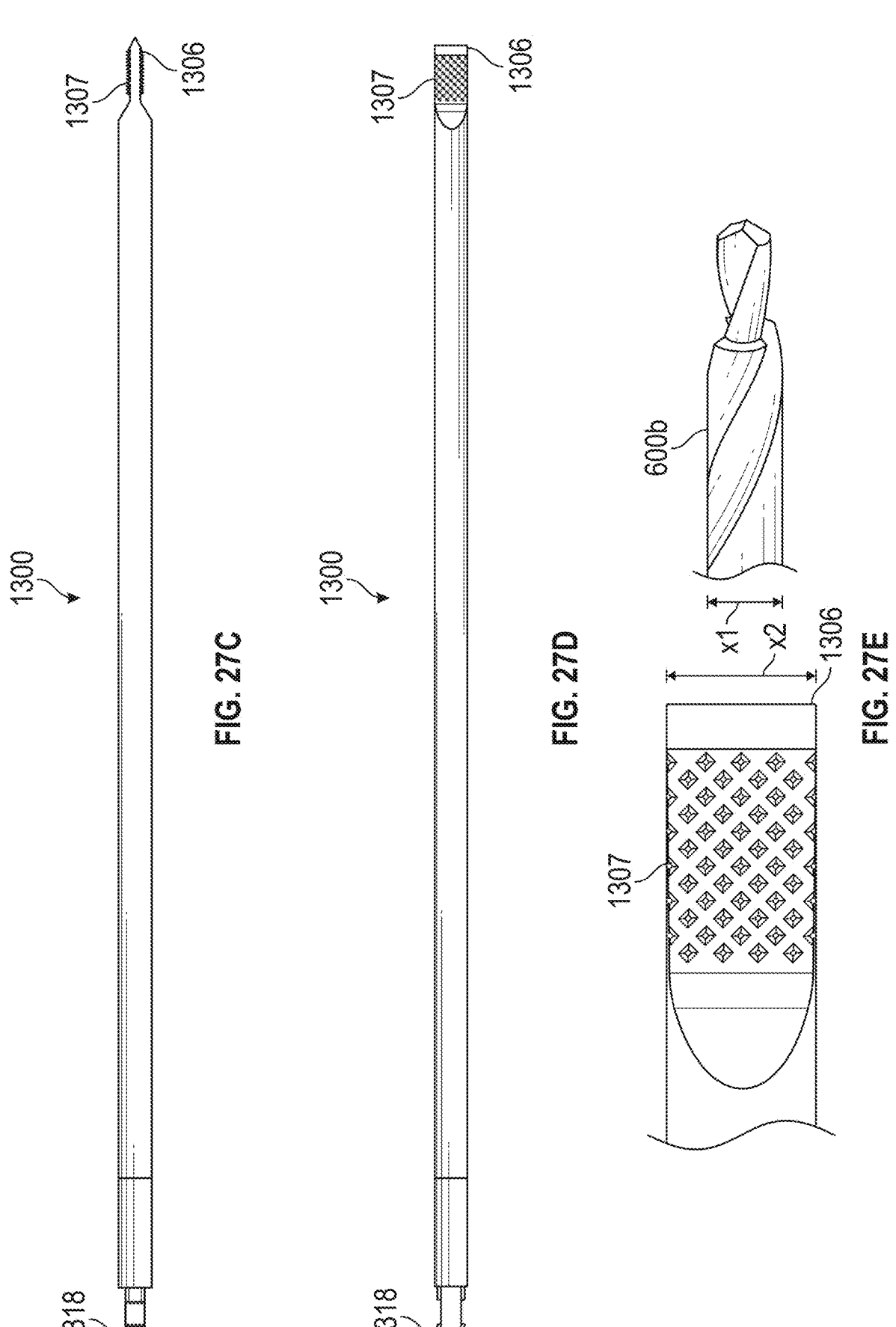
FIG. 27C illustrates a side view of the rasp of FIG. 27A.
FIG. 27D illustrates a top view of the rasp of FIG. 27A.
FIG. 27E illustrates a top view of an embodiment of a rasp and a drill bit.

The distal end 1306 and rasping tip 1307 can be dimensioned, shaped, or otherwise configured to be inserted into a facet joint. In certain embodiments, the rasp 1300 can be used to decorticate bone within a facet joint. In certain embodiments, the rasp 1300 can be used to decorticate bone in the facet joint prior to forming a pilot hole with a drill bit and/or implanting an intrafacet implant. As shown in FIG. 27E, The rasping tip 1307 can be dimensioned to be wider than a drill bit used in a procedure for implanting an intrafacet implant. For example, as shown in FIG. 27E, the rasping surface 1310a and/or the rasping surface 1310b can have a width $X_2$ that is wider than a width $X_1$ of the drill bit 600b or any other drill bit described herein. For example, in certain embodiments, the width $X_2$ can be about 6 mm and the width $X_1$ can be about 4.5 mm. In certain embodiments, the width $X_2$ can be between 5 mm and 7 mm and the width $X_1$ can be between 3.5 mm and 4.5 mm. The rasping surface 1310a and/or the rasping surface 1310b may also be wider than the intrafacet implant. A rasping surface 1310a and/or rasping surface 1310b that is wider than the drill bit and/or implant can create an area of decortication in the facet joint around (e.g., laterally beyond a cross-sectional area of) the implant to promote bone fusion.

In certain embodiments, the rasp 1300 can be advanced to the facet joint using a guide, such as the guide 108, for example, prior to advancing a drill bit to the facet joint using the guide 108 as described herein. In certain embodiments, the rasp 1300 can be used to decorticate within the facet joint prior to implantation of the implant, and a second rasp (e.g., rasp 700a, rasp 700b) can be used to rasp over the facet joint after implantation of the implant, as described herein.

Although use of the devices has been described with respect to an example spinal procedure, the devices described herein can also be used in other spinal procedures and other orthopedic applications to deliver bone graft material to other locations in the body (for example, the femur or tibia).

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Various combinations and subcombinations of the various features described herein are possible. For example, a rasp can include a main body, a handle, and a rasping surface. The main body can be integrally formed with the handle and/or a rasping surface and/or any or all of the components can have a modular configuration such that various handles and/or rasping surfaces can be selected and exchanged as desired by the surgeon or other user. A rasp can have a curved or distal section. A distal tip can have any suitable configuration, including bullet-shaped, flat, conical, or any other configuration. The rasp can be configured to receive a suitable mechanism for advancing bone graft material through the rasp, such as a plunger or pusher rod.

What is claimed is:

1. A method for implanting an intrafacet implant, comprising:
    making an incision;
    advancing an instrument assembly through the incision and to a facet joint using an intrafacet approach, the instrument assembly comprising a guide having a lumen extending therethrough;
    anchoring the guide at the facet joint;
    advancing a cutting tool through the guide to the facet joint through an entry point between a first articular process and a second articular process and forming a pilot hole using the cutting tool, wherein the pilot hole is formed partially within the first articular process and partially within the second articular process, wherein the cutting tool comprises a distal section of the cutting tool configured to form a distal section of the pilot hole partially within the first articular process and partially within the second articular process and a proximal section of the cutting tool configured to form a proximal section of the pilot hole partially within the first articular process and partially within the second articular process such that a cross-sectional area of the proximal section of the pilot hole is larger than a cross-sectional area of the distal section of the pilot hole;
    advancing the intrafacet implant to the facet joint through the guide using an inserter; and
    driving the intrafacet implant into the pilot hole.

2. The method of claim 1, wherein the proximal section of the cutting tool comprises a plurality of saw teeth, and the distal section of the cutting tool comprises a flute drill bit section or twist drill bit section.

3. The method of claim 1, wherein the proximal section of the cutting tool comprises a tapered blade, and the distal section of the cutting tool comprises a flute drill bit section or twist drill bit section.

4. The method of claim 1, wherein the inserter comprises a distal tip configured to couple with the intrafacet implant and a split extending proximally through the distal tip from a distal end of the inserter to a relief.

5. The method of claim 1, wherein the instrument assembly comprises a stylet comprising a distal tip, wherein the stylet is positioned within the guide of the instrument assembly while advancing the instrument assembly through the incision and to the facet joint, the method further comprises penetrating tissue with the distal tip of the stylet.

6. The method of claim 5, further comprising removing the stylet prior to advancing the intrafacet implant to the facet joint.

7. The method of claim 1, wherein anchoring the guide at the facet joint comprises anchoring a plurality of prongs of the guide at the facet joint.

8. The method of claim 1, further comprising rasping the facet joint using a rasp after driving the intrafacet implant into the pilot hole.

9. The method of claim 1, wherein the intrafacet implant comprises a body extending from a proximal end to a distal end of the intrafacet implant and a plurality of threads extending from the body from the proximal end to the distal end.

10. The method of claim 9, wherein the body of the intrafacet implant comprises a uniform cross-sectional area.

11. The method of claim 1, further comprising advancing a rasp to the facet joint and decorticating bone of the facet joint with the rasp, wherein a rasping surface of the rasp is wider than a width of the cutting tool.

12. The method of claim 11, wherein the rasping surface is a first rasping surface, the rasp comprising a second rasping surface positioned on an opposite side of the first rasping surface.

13. The method of claim 1, wherein driving the intrafacet implant into the pilot hole comprises countersinking the intrafacet implant within the facet joint.

14. The method of claim 1, further comprising delivering bone graft material into the facet joint to cover a proximal end of the intrafacet implant.

15. The method of claim 1, further comprising delivering bone graft material into an interior of the intrafacet implant after driving the intrafacet implant into the pilot hole.

16. A method for implanting an intrafacet implant, comprising:
    making an incision;
    advancing an instrument assembly through the incision and to a facet joint, the instrument assembly comprising a guide having a lumen extending therethrough;
    anchoring the guide at the facet joint;
    advancing a rasp to the facet joint and decorticating bone of the facet joint with the rasp;
    advancing a drill bit to the facet joint and forming a pilot hole for the intrafacet implant after decorticating bone of the facet joint with the rasp;
    advancing the intrafacet implant to the facet joint through the guide using an inserter; and
    countersinking the intrafacet implant within the facet joint using the inserter;
    wherein a rasping surface of the rasp is wider than a width of the drill bit.

17. The method of claim 16, wherein the rasping surface is a first rasping surface, the rasp comprising a second rasping surface positioned on an opposite side of the first rasping surface.

18. The method of claim 16, wherein the inserter comprises a distal tip configured to couple with the intrafacet implant and a split extending proximally through the distal tip from a distal end of the inserter to a relief.

19. The method of claim 16, wherein anchoring the guide at the facet joint comprises anchoring a plurality of prongs of the guide at the facet joint.

20. The method of claim 16, wherein the rasp comprises a first rasp, the method further comprising rasping the facet joint using a second rasp after countersinking the intrafacet implant within the facet joint.

* * * * *